United States Patent
Abouabdellah et al.

(10) Patent No.: US 9,000,010 B2
(45) Date of Patent: Apr. 7, 2015

(54) ALKYL-HETEROCYCLE CARBAMATE DERIVATIVES, THEIR PREPARATION AND THEIR THERAPEUTIC APPLICATION

(75) Inventors: Ahmed Abouabdellah, Paris (FR); Antoine Ravet, Paris (FR)

(73) Assignee: Sanofi, Paris (FR)

( * ) Notice: Subject to any disclaimer, the term of this patent is extended or adjusted under 35 U.S.C. 154(b) by 75 days.

(21) Appl. No.: 13/574,188

(22) PCT Filed: Jan. 19, 2011

(86) PCT No.: PCT/IB2011/050229
§ 371 (c)(1),
(2), (4) Date: Jul. 19, 2012

(87) PCT Pub. No.: WO2011/089550
PCT Pub. Date: Jul. 28, 2011

(65) Prior Publication Data
US 2012/0295909 A1   Nov. 22, 2012

(30) Foreign Application Priority Data

Jan. 20, 2010  (FR) .................................... 10 50362
Jan. 28, 2010  (FR) .................................... 10 50583

(51) Int. Cl.
*A61K 31/454*  (2006.01)
*C07D 417/12*  (2006.01)

(52) U.S. Cl.
CPC ............ *C07D 417/12* (2013.01); *A61K 31/454* (2013.01)

(58) Field of Classification Search
USPC ............. 514/307, 314, 319, 326, 236.8, 365; 544/130; 546/147, 175, 206; 548/204
See application file for complete search history.

(56) References Cited

U.S. PATENT DOCUMENTS 7,439,257 B2 * 10/2008 Abouabdellah et al. ...... 514/330
7,674,805 B2 *  3/2010 Abouabdellah et al. ...... 514/330

FOREIGN PATENT DOCUMENTS

| DE | 3303741 | 8/1984 |
| EP | 0671389 A1 | 9/1995 |
| FR | 2866884 A1 | 9/2005 |
| WO | WO2004/033422 A2 | 4/2004 |
| WO | WO2005/070910 A2 | 8/2005 |
| WO | WO2005/090347 A1 | 9/2005 |
| WO | WO2009/051119 A1 | 4/2009 |

OTHER PUBLICATIONS

ChemBank, RN 913493-23-9 (2006).*
Ahn et al. "Fatty acid amide hydrolase . . ." Exp. Opin. Drug Discov. vol. 4(7) 763-784 (2009).*
Chemcats 0094165461 (2014).*
Chemcats 0097895413 (2014).*
Improper Markush Fed. Reg. vp; 76(27) 7162-7175, slides 1, 64-67 (2011).*
Johnson et al. "Benzothiophene piperazine . . ." Bioorg. Med. Chem. Lett. vo. 19 1865-1869 (2009).*
Lima et al. "Bioisosterism: a useful . . . " Curr. Med. Chem. v.12 p. 23-39 (2005).*
Patani et al. "Bioisosterim: a rational . . . " Chem Rev v.96 p. 3147-3176(1996).*
Schlosburg, Joel E. et al., "Targeting Fatty Acid Amide Hydrolase (FAAH) to Treat Pain and Inflammation," The AAPS Journal (2009), vol. 11, No. 1, pp. 39-44.
Database Registry [Online] Chemical Abstracts Service, Columbus, Ohio, US; Nov. 17, 2006, XP002633069, retrieved from STN, Database accession No. 913493-23-9, abstract; compounds 913493-23-9.
International Search Report dated May 25, 2011 issued in PCT/IB2011/050229.
French Search Report dated Jun. 11, 2010 issued in FR1050583.
Japanese Office Action in corresponding JP2012-549449, dated Nov. 11, 2014.

* cited by examiner

*Primary Examiner* — Celia Chang
(74) *Attorney, Agent, or Firm* — Scully, Scott, Murphy & Presser P.C.

(57) ABSTRACT

The invention relates to compounds corresponding to the general formula (I):

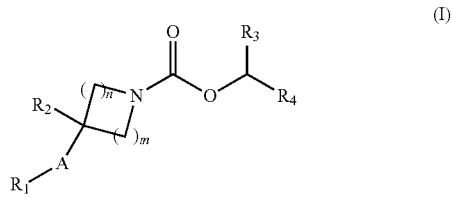

in which $R_2$ represents a hydrogen, fluorine, hydroxyl, cyano, trifluoromethyl, $C_{1-6}$-alkyl, $C_{1-6}$-alkoxy or $-NR_8R_9$; n and m represent, independently of one another, an integer equal to 1, 2 or 3, it being understood that the sum m+n is at most equal to 5; A represents a covalent bond, an oxygen, a $C_{1-6}$-alkylene or $-O-C_{1-6}$-alkylene; $R_1$ represents a phenyl or a heterocycle which is optionally substituted; $R_3$ represents a hydrogen, fluorine, $C_{1-6}$-alkyl or trifluoromethyl; $R_4$ represents an optionally substituted 5-membered heterocycle; in the form of the base or of an addition salt with an acid; with the exclusion of 5-methylisoxazol-3-ylmethyl 4-hydroxy-4-(4-chlorophenyl)piperidine-1-carboxylate.

The invention also relates to a process for the preparation of the compounds of formula (I), to compositions comprising them and to their therapeutic application.

12 Claims, No Drawings

ALKYL-HETEROCYCLE CARBAMATE DERIVATIVES, THEIR PREPARATION AND THEIR THERAPEUTIC APPLICATION

A subject-matter of the invention is alkyl-heterocycle carbamate derivatives, their preparation and their therapeutic application.

There still exists a need to find and develop products which are inhibitors of the enzyme FAAH (Fatty Acid Amide Hydrolase). The compounds of the invention meet this objective.

Furthermore, these compounds have to exhibit metabolic and pharmacokinetic properties and a safety index which allow them to be used as medicaments.

The compounds of the invention correspond to the general formula (I):

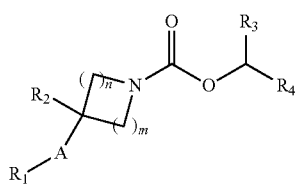

(I)

in which:
- $R_2$ represents a hydrogen or fluorine atom or a hydroxyl, cyano, trifluoromethyl, $C_{1-6}$-alkoxy or —$NR_8R_9$ group;
- n and m represent, independently of one another, an integer equal to 1, 2 or 3, it being understood that the sum m+n is at most equal to 5;
- A represents a covalent bond, an oxygen atom, a $C_{1-6}$-alkylene group or an —O—$C_{1-6}$-alkylene group in which the end represented by an oxygen atom is bonded to the $R_1$ group;
- $R_1$ represents an $R_5$ group optionally substituted by one or more $R_6$ and/or $R_7$ groups;
- $R_5$ representing a group chosen from a phenyl, pyridinyl, pyridazinyl, pyrimidinyl, pyrazinyl, triazinyl, naphthyl, quinolinyl, isoquinolinyl, phthalazinyl, quinazolinyl, quinoxalinyl, cinnolinyl, naphthyridinyl, benzothiazolyl, benzisothiazolyl, benzoxazolyl, benzisoxazolyl, benzimidazolyl, isobenzofuranyl, benzofuranyl, benzothiophenyl, benzothiadiazolyl, benzoxadiazolyl, indazolyl, indolizinyl, indolyl, isoindolyl, imidazopyridinyl, imidazopyrimidinyl, imidazopyrazinyl, imidazopyridazinyl, triazolopyridinyl, pyrrolopyridinyl, pyrrolopyrimidinyl, pyrrolopyrazinyl, pyrrolopyridazinyl, pyrrolotriazinyl, pyrazolopyridinyl, pyrazolopyrimidinyl, pyrazolopyrazinyl, pyrazolopyridazinyl, furopyridinyl, furopyrimidinyl, furopyrazinyl, furopyridazinyl, furotriazinyl, oxazolopyridinyl, oxazolopyrimidinyl, oxazolopyrazinyl, oxazolopyridazinyl, isoxazolopyridinyl, isoxazolopyrimidinyl, isoxazolopyrazinyl, isoxazolopyridazinyl, oxadiazolopyridinyl, thienopyridinyl, thienopyrimidinyl, thienopyrazinyl, thienopyridazinyl, thienotriazinyl, triazolopyridinyl, thiazolopyrimidinyl, thiazolopyrazinyl, thiazolopyridazinyl, isothiazolopyridinyl, isothiazolopyrimidinyl, isothiazolopyrazinyl, isothiazolopyridazinyl or thiadiazolopyridinyl;
- $R_6$ representing a halogen atom or a cyano, —$CH_2CN$, nitro, hydroxyl, $C_{1-8}$-alkyl, $C_{1-6}$-alkoxy, $C_{1-6}$-thioalkyl, $C_{1-6}$-haloalkyl, $C_{1-5}$-haloalkoxy, $C_{1-8}$-halothioalkyl, $C_{3-7}$-cycloalkyl, $C_{3-7}$-cycloalkyl-$C_{1-3}$-alkylene-O—, —$(CH_2)_p$—$NR_8R_9$, —$NR_8COR_9$, —$NR_8CO_2R_9$, —$NR_8SO_2R_9$, —$NR_8SO_2NR_8R_9$, —$COR_8$, —$CO_2R_8$, —$(CH_2)_p$—$CONR_8R_9$, —$SO_2R_8$—$SO_2NR_8R_9$ or —O—($C_{1-3}$-alkylene)-O— group;
- $R_7$ representing a group chosen from a phenyl, phenyl-$C_{1-4}$-alkylene-, phenyl-$(CH_2)_p$—O—, pyridinyl, pyridazinyl, pyrimidinyl, pyrazinyl, triazinyl, furanyl, thienyl, imidazolyl, oxazolyl, isoxazolyl, pyrrolyl, pyrazolyl, tetrazolyl, thiazolyl, isothiazolyl, oxadiazolyl, thiadiazolyl, imidazopyrimidinyl, thienopyrimidinyl, benzofuranyl, benzothienyl, benzimidazolyl, benzoxazolyl, benzisoxazolyl, benzothiazolyl, benzisothiazolyl, indolyl, isoindolyl, indazolyl, pyrrolopyridinyl, furopyridinyl, thienopyridinyl, imidazopyridinyl, pyrazolopyridinyl, oxazolopyridinyl, isoxazolopyridinyl or thiazolopyridinyl; it being possible for the $R_7$ group or groups to be substituted by one or more $R_6$ groups which are identical to or different from one another;
- p representing a number which can have the value 0, 1, 2 or 3;
- $R_3$ represents a hydrogen or fluorine atom, a $C_{1-6}$-alkyl group or a trifluoromethyl group;
- $R_4$ represents a 5-membered heterocycle chosen from a furanyl, pyrrolyl, thienyl, thiazolyl, isothiazolyl, oxazolyl, isoxazolyl, pyrazolyl, oxadiazolyl, thiadiazolyl, imidazolyl, triazolyl or tetrazolyl;

this heterocycle optionally being substituted by one or more substituents chosen from a halogen atom or a $C_{1-6}$-alkyl, $C_{1-6}$-haloalkyl, $C_{3-7}$-cycloalkyl, $C_{3-7}$-cycloalkyl-$C_{1-3}$-alkylene, $C_{1-6}$-haloalkoxy, cyano, —$NR_8R_9$, —$NR_8C(O)R_9$, —$NR_8CO_2R_9$, —$NR_8SO_2R_9$, —$NR_8SO_2NR_8R_9$, —$C(O)R_8$, —$CO_2R_8$, —$C(O)NR_8R_9$, —$C(O)N(R_8)(C_{1-3}$-alkylene-$NR_{10}R_{11}$), —$SO_2R_8$, —$SO_2NR_8R_9$ or —O— ($C_{1-3}$-alkylene)-O— group;

- $R_8$ and $R_9$ representing, independently of one another, a hydrogen atom or a $C_{1-6}$-alkyl group, or forming, with the nitrogen atom or atoms which carry them,
  - in the case of $NR_8R_9$, a ring chosen from the azetidine, pyrrolidine, piperidine, morpholine, thiomorpholine, azepine, oxazepine or piperazine rings, this ring optionally being substituted by a $C_{1-6}$-alkyl or benzyl group;
  - in the case of $NR_8COR_9$, a lactam ring;
  - in the case of $NR_8CO_2R_9$, an oxazolidinone, oxazinone or oxazepinone ring;
  - in the case of $NR_8SO_2R_9$, a sultam ring;
  - in the case of $NR_8SO_2NR_8R_9$, a thiazolidine dioxide or thiadiazinane dioxide ring;
- $R_{10}$ and $R_{11}$ representing, independently of one another, a hydrogen atom or a $C_{1-6}$-alkyl group;

with the exclusion of the following compound:
5-methylisoxazol-3-ylmethyl 4-hydroxy-4-(4-chlorophenyl)-piperidine-1-carboxylate.

Among the compounds of general formula (I), a first subgroup of compounds is composed of the compounds for which $R_2$ represents a hydrogen atom.

Among the compounds of general formula (I), a second subgroup of compounds is composed of the compounds for which m and n represent, independently of one another, the value 1 or 2.

Among the compounds of general formula (I), a third subgroup of compounds is composed of the compounds for which m and n each represent the value 2.

Among the compounds of general formula (I), a fourth subgroup of compounds is composed of the compounds for which A represents an —O—$C_{1-6}$-alkylene group in which the end represented by an oxygen atom is bonded to the $R_1$ group, in particular an —O—$(CH_2)_2$— group, also known as an ethyleneoxy group.

Among the compounds of general formula (I), a fifth subgroup of compounds is composed of the compounds for which A represents an —O—$C_{1-6}$-alkylene group in which the end represented by an oxygen atom is bonded to the $R_1$ group, in particular an —O—$CH_2$— group, also known as a methyleneoxy group.

Among the compounds of general formula (I), a sixth subgroup of compounds is composed of the compounds for which $R_1$ represents an $R_5$ group optionally substituted by one or more $R_6$ and/or $R_7$ groups;

$R_5$ representing a group chosen from a phenyl, pyridinyl, pyridazinyl, pyrimidinyl, pyrazinyl, triazinyl, naphthyl, quinolinyl, isoquinolinyl, phthalazinyl, quinoxalinyl, quinazolinyl, cinnolinyl, naphthyridinyl, benzothiazolyl, benzisothiazolyl, benzoxazolyl, benzisoxazolyl, benzimidazolyl, isobenzofuranyl, benzofuranyl, benzothiophenyl, indazolyl, indolizinyl, indolyl, isoindolyl, pyrrolopyridinyl, furopyridinyl or thienopyridinyl;

$R_6$ representing a halogen atom or a cyano, —$CH_2CN$, nitro, hydroxyl, $C_{1-8}$-alkyl, $C_{1-6}$-alkoxy, $C_{1-6}$-thioalkyl, $C_{1-6}$-haloalkyl, $C_{1-6}$-haloalkoxy, $C_{1-6}$-halothioalkyl, $C_{3-7}$-cycloalkyl, $C_{3-7}$-cycloalkyl-$C_{1-3}$-alkylene, $C_{3-7}$-cycloalkyl-$C_{1-3}$-alkylene-O—, —$(CH_2)_p$—$NR_8R_9$, —$NR_8COR_9$, —$NR_8CO_2R_9$, —$NR_8SO_2R_9$, —$NR_8SO_2NR_8R_9$, —$COR_8$, —$CO_2R_8$, —$(CH_2)_p$—$CONR_8R_9$, —$SO_2R_8$, —$SO_2NR_8R_9$ or —O—($C_{1-3}$-alkylene)-O— group;

$R_7$ representing a group chosen from a phenyl, phenyl-$C_{1-4}$-alkylene-, phenyl-$(CH_2)_p$—O—, pyridinyl, pyridazinyl, isoxazolyl, benzothiazolyl, pyrrolyl, pyrazolyl, tetrazolyl, pyrimidinyl, thiazolyl, pyrazinyl, triazinyl or benzoxazolyl; it being possible for the $R_7$ group or groups to be substituted by one or more $R_6$ groups, which are identical to or different from one another, as defined above;

p representing a number which can have the value 0, 2 or 3;

$R_8$ and $R_9$ representing, independently of one another, a hydrogen atom or a $C_{1-6}$-alkyl group;

or forming, with the nitrogen atom(s) which carry them, in the case of $NR_8R_9$, a ring chosen from the azetidine, pyrrolidine, piperidine, morpholine, thiomorpholine, azepine, oxazepine or piperazine rings, this ring optionally being substituted by a $C_{1-5}$-alkyl or benzyl group;

in the case of $NR_8COR_9$, a lactam ring;

in the case of $NR_8CO_2R_9$, an oxazolidinone, oxazinone or oxazepinone ring;

in the case of $NR_8SO_2R_9$, a sultam ring;

in the case of $NR_8SO_2NR_8R_9$, a thiazolidine dioxide or thiadiazinane dioxide ring.

Among the compounds of general formula (I), a seventh subgroup of compounds is composed of the compounds for which $R_1$ represents an $R_5$ group optionally substituted by one or more $R_6$ and/or $R_7$ groups;

$R_5$ representing a group chosen from a phenyl, benzothiazolyl, pyridinyl, pyridazinyl, pyrimidinyl, pyrazinyl, triazinyl, naphthyl, quinolinyl, isoquinolinyl, phthalazinyl, quinoxalinyl, cinnolinyl, naphthyridinyl or indolyl;

$R_6$ representing a halogen atom or a cyano, —$CH_2CN$, nitro, hydroxyl, $C_{1-8}$-alkyl, $C_{1-5}$-alkoxy, $C_{1-5}$-thioalkyl, $C_{1-6}$-haloalkyl, $C_{1-6}$-haloalkoxy, $C_{1-6}$-halothioalkyl, $C_{3-7}$-cycloalkyl, $C_{3-7}$-cycloalkyl-$C_{1-3}$-alkylene, $C_{3-7}$-cycloalkyl-$C_{1-3}$-alkylene-O—, —$(CH_2)_p$—$NR_8R_9$, —$NR_8COR_9$, —$NR_8CO_2R_9$, —$NR_8SO_2R_9$, —$NR_8SO_2NR_8R_9$, —$COR_8$, —$CO_2R_8$, —$(CH_2)_p$—$CONR_8R_9$, —$SO_2R_8$, —$SO_2NR_8R_9$ or —O—($C_{1-3}$-alkylene)-O— group;

$R_7$ representing a group chosen from a phenyl, phenyl-$C_{1-4}$-alkylene-, phenyl-$(CH_2)_p$—O—, pyridinyl, pyridazinyl, isoxazolyl, benzothiazolyl, pyrrolyl, pyrazolyl, tetrazolyl, pyrimidinyl, thiazolyl, pyrazinyl, triazinyl or benzoxazolyl; it being possible for the $R_7$ group or groups to be substituted by one or more $R_6$ groups which are identical to or different from one another;

p representing a number which can have the value 0, 1, 2 or 3;

$R_8$ and $R_9$ representing, independently of one another, a hydrogen atom or a $C_{1-6}$-alkyl group, or forming, with the nitrogen atom which carries them, in the case of $NR_8R_9$, a ring chosen from azetidine, pyrrolidine, piperidine, morpholine, thiomorpholine, azepine, oxazepine or piperazine rings, this ring optionally being substituted by a $C_{1-6}$-alkyl or benzyl group;

in the case of $NR_8COR_9$, a lactam ring;

in the case of $NR_8CO_2R_9$, an oxazolidinone, oxazinone or oxazepinone ring;

in the case of $NR_8SO_2R_9$, a sultam ring;

in the case of $NR_8SO_2NR_8R_9$, a thiazolidine dioxide or thiadiazinane dioxide ring.

Among the compounds of general formula (I), an eighth subgroup of compounds is composed of the compounds for which $R_1$ represents a group chosen from a phenyl, benzothiazolyl, naphthyl, quinolinyl, isoquinolinyl or indolyl, optionally substituted by one or more $R_6$ and/or $R_7$ groups;

$R_6$ representing a halogen atom or a cyano, $C_{1-6}$-alkoxy, $C_{1-6}$-haloalkyl, $C_{1-6}$-haloalkoxy, $C_{3-7}$-cycloalkyl, —$(CH_2)_p$—$NR_8R_9$, —$NR_8COR_9$, —$CO_2R_8$, —$(CH_2)_p$—$CONR_8R_9$, —$SO_2R_8$ or —$SO_2NR_8R_9$ group;

$R_7$ representing a group chosen from a phenyl, phenyl-$C_{1-4}$-alkylene-, phenyl-$(CH_2)_p$—O—, isoxazolyl, benzothiazolyl, pyrrolyl, pyrazolyl, tetrazolyl, thiazolyl or benzoxazolyl; it being possible for the $R_7$ group or groups to be substituted by one or more $R_6$ groups, which are identical to or different from one another, as defined above;

p representing a number which can have the value 0 or 1;

$R_8$ and $R_9$ representing, independently of one another, a hydrogen atom or a group; or else $R_8$ and $R_9$ forming, with the nitrogen atom which carries them, in the case of —$NR_8R_9$, a morpholine ring;

in the case of —$NR_8COR_9$, a lactam ring.

Among the compounds of general formula (I), a ninth subgroup of compounds is composed of the compounds for which $R_3$ represents a hydrogen atom.

Among the compounds of general formula (I), a tenth subgroup of compounds is composed of the compounds for which $R_4$ represents a 5-membered heterocycle chosen from a pyrazolyl, imidazolyl, thiazolyl, isothiazolyl, oxazolyl or isoxazolyl;

this heterocycle optionally being substituted by one or more —$C(O)NR_8R_9$ substituents in which $R_8$ and $R_9$ each represent a hydrogen atom.

Among the compounds of general formula (I), an eleventh subgroup of compounds is composed of the compounds for which $R_4$ represents a 5-membered heterocycle chosen from a thiazolyl or isoxazolyl;

this heterocycle optionally being substituted by one or more —$C(O)NR_8R_9$ substituents in which $R_8$ and $R_9$ each represent a hydrogen atom.

Among the compounds of general formula (I), mention may be made of a twelfth subgroup represented by the compounds of formula (Ii):

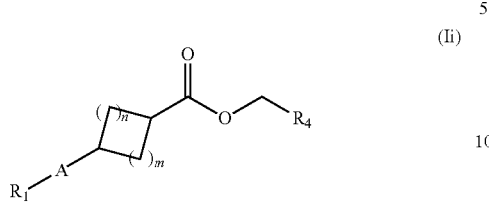

in which $R_1$, A, $R_4$, n and m are as defined above.

Other subgroups composed of the compounds of formula (II) also come within the present invention.

Thus, among the compounds of abovementioned general formula (II), a subgroup of compounds is composed of the compounds for which A represents an —O—$(CH_2)_2$— group.

Among the compounds of abovementioned general formula (II), a subgroup of compounds is composed of the compounds for which A represents an —O—$CH_2$— group.

Among the compounds of general formula (I), mention may be made of a thirteenth subgroup represented by the compounds of formula (Iii):

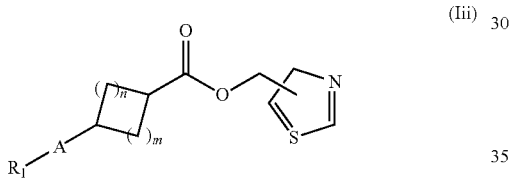

in which $R_1$, A, n and m are as defined above.

Other subgroups composed of the compounds of formula (Iii) also come within the present invention.

Thus, among the compounds of abovementioned general formula (Iii), a subgroup of compounds is composed of the compounds for which A represents an —O—$(CH_2)_2$— group.

Thus, among the compounds of abovementioned general formula (Iii), a subgroup of compounds is composed of the compounds for which A represents an —O—$CH_2$— group.

Among the compounds of general formula (I), a fourteenth subgroup is composed of the compounds of general formula (I) in which:
- $R_2$ represents a hydrogen atom;
- m and n represent, independently of one another, the value 1 or 2;
- A represents an —O—$C_{1-6}$-alkylene group in which the end represented by an oxygen atom is bonded to the $R_1$ group, in particular an ethyleneoxy ou methyleneoxy group;
- $R_1$ represents a group chosen from a phenyl, benzothiazolyl, naphthyl, quinolinyl, isoquinolinyl or indolyl, optionally substituted by one or more $R_6$ and/or $R_7$ groups;
- $R_6$ representing:
  - a halogen atom, in particular a chlorine, fluorine or bromine;
  - a cyano group;
  - a $C_{1-8}$-alkyl group, in particular a methyl, isopropyl, 1,1,3,3-tetramethylbutyl or tert-butyl;
  - a $C_{1-6}$-alkoxy group, in particular a methoxy, hexyloxy, butoxy, ethoxy;
  - a $C_{1-6}$-haloalkyl group, in particular a trifluoromethyl, pentafluoroethyl;
  - a $C_{1-6}$-haloalkoxy group, in particular a trifluoromethoxy or difluoromethoxy;
  - a $C_{3-7}$-cycloalkyl group, in particular a cyclopentyl;
  - a —$(CH_2)_p$—$NR_8R_9$ group, in which p has the value 0 or 1; $R_8$ and $R_9$ each represent a hydrogen atom or $R_8$ and $R_9$ each represent a methyl, or else $R_8$ and $R_9$ form, with the nitrogen atom which carries them, a morpholine ring;
  - an —$NR_8COR_9$ group, in which $R_8$ represents a hydrogen atom and $R_9$ represents a methyl, or else $R_8$ and $R_9$ form, with the nitrogen atom which carries them, a lactam ring, in particular a β-lactam ring;
  - a —$CO_2R_8$ group, in which $R_8$ represents a methyl;
  - a —$(CH_2)_p$—$CONR_8R_9$ group, in which p has the value 0 or 1 and $R_8$ and $R_9$ each represent a hydrogen atom;
  - an —$SO_2R_8$ group, in which $R_8$ represents a methyl;
  - an —$SO_2NR_8R_9$ group, in which $R_8$ and $R_9$ each represent a hydrogen atom;
- $R_7$ representing a group chosen from a phenyl group; a phenyl-$C_{1-4}$-alkylene- group, in particular a 1,1-dimethyl-1-phenylmethylene or a benzyl; a phenyl-$(CH_2)_p$—O— group in which p has a value of 0 or 1; or an isoxazolyl, benzothiazolyl, pyrrolyl, pyrazolyl, tetrazolyl, thiazolyl or benzoxazolyl group; it being possible for the $R_7$ group or groups to be substituted by one or more $R_6$ groups, which are identical to or different from one another, as defined above, such as a halogen atom or a cyano group;
- $R_3$ represents a hydrogen atom;
- $R_4$ represents a 5-membered heterocycle chosen from a thiazolyl or isoxazolyl; this heterocycle optionally being substituted by one or more —$C(O)NR_8R_9$ substituents in which $R_8$ and $R_9$ each represent a hydrogen atom.

Among the compounds of general formula (I), a fifteenth subgroup of compounds is composed of the compounds of general formula (I) in which, simultaneously, $R_1$ and/or $R_2$ and/or $R_3$ and/or $R_4$ and/or n and/or m and/or A are as defined in the above subgroups.

Among the compounds of general formula (I), the following compounds may be cited (IUPAC nomenclature generated by the AutoNom software):

1. Thiazol-2-ylmethyl 4-[2-(4-chloronaphth-1-yloxy)ethyl]-piperidine-1-carboxylate
2. Thiazol-2-ylmethyl 4-[2-(4-fluorophenoxy)ethyl]-piperidine-1-carboxylate
3. Thiazol-4-ylmethyl 4-[2-(4-fluorophenoxy)ethyl]-piperidine-1-carboxylate
4. Thiazol-4-ylmethyl 4-[2-(4-{trifluoromethyl}phenoxy)-ethyl]piperidine-1-carboxylate
5. Thiazol-4-ylmethyl 4-[2-(4-chlorophenoxy)ethyl]-piperidine-1-carboxylate
6. Thiazol-5-ylmethyl 4-[2-(4-fluorophenoxy)ethyl]-piperidine-1-carboxylate
7. Thiazol-5-ylmethyl 4-[2-(4-chlorophenoxy)ethyl]-piperidine-1-carboxylate
8. Thiazol-5-ylmethyl 4-[2-(4-{trifluoromethyl}phenoxy)-ethyl]piperidine-1-carboxylate
9. Thiazol-4-ylmethyl 4-[2-(7-methoxynaphth-2-yloxy)ethyl]-piperidine-1-carboxylate
10. Thiazol-4-ylmethyl 4-[2-(4-cyanophenoxy)ethyl]-piperidine-1-carboxylate
11. Thiazol-4-ylmethyl (+/−)-3-(6-methoxynaphth-2-yloxymethyl)pyrrolidine-1-carboxylate 12. Thiazol-4-ylmethyl (+/−)-3-(7-methoxynaphth-2-yloxymethyl)pyrrolidine-1-carboxylate
13. Thiazol-4-ylmethyl (+/−)-3-(3,4-dichlorophenoxymethyl)pyrrolidine-1-carboxylate
14. Thiazol-4-ylmethyl 4-[2-(6-methoxynaphth-2-yloxy)-ethyl]piperidine-1-carboxylate
15. Thiazol-4-ylmethyl 4-[2-(naphth-2-yloxy)ethyl]-piperidine-1-carboxylate
16. Thiazol-4-ylmethyl (+/−)-3-(4-chloronaphth-1-yloxymethyl)pyrrolidine-1-carboxylate
17. Thiazol-4-ylmethyl (+/−)-3-(naphth-2-yloxymethyl)-pyrrolidine-1-carboxylate
18. Thiazol-4-ylmethyl 4-[2-(4'-fluorobiphenyl-4-yloxy)-ethyl]piperidine-1-carboxylate
19. Thiazol-4-ylmethyl 4-[2-(quinolin-6-yloxy)ethyl]-piperidine-1-carboxylate and its hydrochloride
20. Thiazol-4-ylmethyl 4-[2-(isoquinolin-6-yloxy)ethyl]-piperidine-1-carboxylate and its hydrochloride
21. Thiazol-4-ylmethyl (+/−)-3-(3'-cyanobiphenyl-3-yloxymethyl)pyrrolidine-1-carboxylate
22. Thiazol-4-ylmethyl (+/−)-3-(4'-fluorobiphenyl-4-yloxymethyl)pyrrolidine-1-carboxylate
23. Thiazol-4-ylmethyl (+/−)-3-(5-chloronaphth-2-yloxymethyl)pyrrolidine-1-carboxylate
24. Thiazol-4-ylmethyl (+/−)-3-(3-{trifluoromethoxy}-phenoxymethyl)pyrrolidine-1-carboxylate
25. Thiazol-4-ylmethyl (+/−)-3-[4-(1-methyl-1-phenyl-ethyl)phenoxymethyl]pyrrolidine-1-carboxylate
26. Thiazol-4-ylmethyl (+/−)-3-(quinolin-3-yloxymethyl)-pyrrolidine-1-carboxylate
27. Thiazol-4-ylmethyl (+/−)-3-(isoquinolin-6-yloxymethyl)pyrrolidine-1-carboxylate
28. Thiazol-4-ylmethyl (+/−)-3-(quinolin-7-yloxymethyl)-pyrrolidine-1-carboxylate
29. Thiazol-4-ylmethyl (+/−)-3-(isoquinolin-7-yloxymethyl)pyrrolidine-1-carboxylate
30. Thiazol-4-ylmethyl (+/−)-3-(4-chloro-3-{trifluoromethyl}phenoxymethyl)pyrrolidine-1-carboxylate
31. Thiazol-4-ylmethyl (+/−)-3-(5-fluoronaphth-2-yloxymethyl)pyrrolidine-1-carboxylate
32. Thiazol-2-ylmethyl 4-[2-(2,4-dimethylphenoxy)ethyl]-piperidine-1-carboxylate
33. Thiazol-2-ylmethyl 4-[2-(2,3-dichlorophenoxy)ethyl]-piperidine-1-carboxylate
34. Thiazol-2-ylmethyl 4-[2-(2,4-dichlorophenoxy)ethyl]-piperidine-1-carboxylate
35. Thiazol-2-ylmethyl 4-[2-(2,5-dichlorophenoxy)ethyl]-piperidine-1-carboxylate
36. Thiazol-2-ylmethyl 4-[2-(3,4-dichlorophenoxy)ethyl]-piperidine-1-carboxylate
37. Thiazol-2-ylmethyl 4-[2-(3,5-dichlorophenoxy)ethyl]-piperidine-1-carboxylate
38. Thiazol-2-ylmethyl 4-[2-(4-cyclopentylphenoxy)-ethyl]piperidine-1-carboxylate
39. Thiazol-2-ylmethyl 4-[2-(2-{benzoxazol-2-yl}-phenoxy)ethyl]piperidine-1-carboxylate
40. Thiazol-2-ylmethyl 4-[2-(4-{benzyloxy}phenoxy)ethyl]piperidine-1-carboxylate
41. Thiazol-2-ylmethyl 4-[2-(4-{carbamoylmethyl}-phenoxy)ethyl]piperidine-1-carboxylate
42. Thiazol-2-ylmethyl 4-[2-(quinolin-7-yloxy)ethyl]-piperidine-1-carboxylate and its trifluoroacetate
43. Thiazol-2-ylmethyl 4-[2-(quinolin-6-yloxy)ethyl]-piperidine-1-carboxylate and its trifluoroacetate
44. Thiazol-2-ylmethyl 4-[2-(4-cyano-3-fluorophenoxy)-ethyl]piperidine-1-carboxylate
45. Thiazol-2-ylmethyl 4-[2-(biphenyl-2-yloxy)ethyl]-piperidine-1-carboxylate
46. Thiazol-2-ylmethyl 4-[2-(2-isopropyl-5-methyl-phenoxy)ethyl]piperidine-1-carboxylate
47. Thiazol-2-ylmethyl 4-[2-(3-{trifluoromethyl}-phenoxy)ethyl]piperidine-1-carboxylate
48. Thiazol-2-ylmethyl 4-{2-[4-(1,1,3,3-tetramethyl-butyl)phenoxy]ethyl}piperidine-1-carboxylate
49. Thiazol-2-ylmethyl 4-[2-(4-benzylphenoxy)ethyl]-piperidine-1-carboxylate
50. Thiazol-2-ylmethyl 4-[2-(4-{pyrrol-1-yl}phenoxy)-ethyl]piperidine-1-carboxylate and its trifluoroacetate
51. Thiazol-2-ylmethyl 4-[2-(4-carbamoylphenoxy)ethyl]-piperidine-1-carboxylate
52. Thiazol-2-ylmethyl 4-[2-(3-cyanophenoxy)ethyl]-piperidine-1-carboxylate
53. Thiazol-2-ylmethyl 4-[2-(3,5-di{tert-butyl}phenoxy)-ethyl]piperidine-1-carboxylate
54. Thiazol-2-ylmethyl 4-[2-(2-benzylphenoxy)ethyl]-piperidine-1-carboxylate
55. Thiazol-2-ylmethyl 4-[2-(8-{acetylamino}naphth-2-yloxy)ethyl]piperidine-1-carboxylate
56. Thiazol-2-ylmethyl 4-[2-(3-{methoxycarbonyl}naphth-2-yloxy)ethyl]piperidine-1-carboxylate
57. Thiazol-2-ylmethyl 4-[2-(3-phenoxyphenoxy)ethyl]-piperidine-1-carboxylate
58. Thiazol-2-ylmethyl 4-[2-(isoquinolin-7-yloxy)ethyl]-piperidine-1-carboxylate and its trifluoroacetate
59. Thiazol-2-ylmethyl 4-[2-(4-hexyloxyphenoxy)ethyl]-piperidine-1-carboxylate
60. Thiazol-2-ylmethyl 4-[2-(3-butoxyphenoxy)ethyl]-piperidine-1-carboxylate
61. Thiazol-2-ylmethyl 4-[2-(quinolin-5-yloxy)ethyl]-piperidine-1-carboxylate and its trifluoroacetate
62. Thiazol-2-ylmethyl 4-[2-(3-{pentafluoroethyl}-phenoxy)ethyl]piperidine-1-carboxylate
63. Thiazol-2-ylmethyl 4-[2-(5-{acetylamino}naphth-2-yloxy)ethyl]piperidine-1-carboxylate
64. Thiazol-2-ylmethyl 4-[2-(5-bromo-2-chlorophenoxy)-ethyl]piperidine-1-carboxylate
65. Thiazol-2-ylmethyl 4-[2-(2-methylquinolin-6-yloxy)-ethyl]piperidine-1-carboxylate and its trifluoroacetate
66. Thiazol-2-ylmethyl 4-[2-(4'-cyanobiphenyl-3-yloxy)-ethyl]piperidine-1-carboxylate
67. Thiazol-2-ylmethyl 4-[2-(6-cyanonaphth-2-yloxy)-ethyl]piperidine-1-carboxylate
68. Thiazol-2-ylmethyl 4-[2-(4-{thiazol-2-yl}phenoxy)-ethyl]piperidine-1-carboxylate
69. Thiazol-2-ylmethyl 4-[2-(biphenyl-3-yloxy)ethyl]-piperidine-1-carboxylate
70. Thiazol-2-ylmethyl 4-[2-(biphenyl-4-yloxy)ethyl]-piperidine-1-carboxylate
71. Thiazol-2-ylmethyl 4-[2-(2-cyanoquinolin-8-yloxy)-ethyl]piperidine-1-carboxylate and its trifluoroacetate
72. Thiazol-2-ylmethyl 4-[2-(4-chloro-2-cyanophenoxy)-ethyl]piperidine-1-carboxylate and its trifluoroacetate
73. Thiazol-2-ylmethyl 4-[2-(2-methylbenzothiazol-5-yloxy)ethyl]piperidine-1-carboxylate
74. Thiazol-2-ylmethyl 4-[2-(4'-cyanobiphenyl-4-yloxy)-ethyl]piperidine-1-carboxylate
75. Thiazol-2-ylmethyl 4-[2-(2-{morpholin-4-yl}phenoxy)-ethyl]piperidine-1-carboxylate
76. Thiazol-2-ylmethyl 4-[2-(4-chloro-2-{isoxazol-5-yl}-phenoxy)ethyl]piperidine-1-carboxylate
77. Thiazol-4-ylmethyl 4-[2-(2,4-dimethylphenoxy)ethyl]-piperidine-1-carboxylate 78. Thiazol-4-ylmethyl 4-[2-(2,3-dichlorophenoxy)ethyl]-piperidine-1-carboxylate
79. Thiazol-4-ylmethyl 4-[2-(naphth-1-yloxy)ethyl]-piperidine-1-carboxylate
80. Thiazol-4-ylmethyl 4-[2-(3-{dimethylamino}phenoxy)-ethyl]piperidine-1-carboxylate and its trifluoroacetate
81. Thiazol-4-ylmethyl 4-[2-(3-{trifluoromethyl}-phenoxy)ethyl]piperidine-1-carboxylate
82. Thiazol-4-ylmethyl 4-[2-(4-benzylphenoxy)ethyl]-piperidine-1-carboxylate
83. Thiazol-4-ylmethyl 4-[2-(2-ethoxyphenoxy)ethyl]-piperidine-1-carboxylate
84. Thiazol-4-ylmethyl 4-{2-[4-(1-methyl-1-phenylethyl)-phenoxy]ethyl}piperidine-1-carboxylate
85. Thiazol-4-ylmethyl 4-[2-(4-phenoxyphenoxy)ethyl]-piperidine-1-carboxylate
86. Thiazol-4-ylmethyl 4-[2-(2-bromo-4-fluorophenoxy)-ethyl]piperidine-1-carboxylate
87. Thiazol-4-ylmethyl 4-[2-(2-benzylphenoxy)ethyl]-piperidine-1-carboxylate
88. Thiazol-4-ylmethyl 4-[2-(3-phenoxyphenoxy)ethyl]-piperidine-1-carboxylate
89. Thiazol-4-ylmethyl 4-[2-(4-{hexyloxy}phenoxy)ethyl]-piperidine-1-carboxylate
90. Thiazol-4-ylmethyl 4-[2-(3-butoxyphenoxy)ethyl]-piperidine-1-carboxylate
91. Thiazol-4-ylmethyl 4-[2-(4-chloro-5-isopropyl-2-methylphenoxy)ethyl]piperidine-1-carboxylate
92. Thiazol-4-ylmethyl 4-[2-(3-{pentafluoroethyl}-phenoxy)ethyl]piperidine-1-carboxylate
93. Thiazol-4-ylmethyl 4-[2-(5-{acetylamino}naphth-2-yloxy)ethyl]piperidine-1-carboxylate
94. Thiazol-4-ylmethyl 4-[2-(5-bromo-2-chlorophenoxy)-ethyl]piperidine-1-carboxylate
95. Thiazol-4-ylmethyl 4-[2-(4'-cyanobiphenyl-3-yloxy)-ethyl]piperidine-1-carboxylate
96. Thiazol-4-ylmethyl 4-[2-(6-cyanonaphth-2-yloxy)-ethyl]piperidine-1-carboxylate
97. Thiazol-4-ylmethyl 4-[2-(4-{thiazol-2-yl}phenoxy)-ethyl]piperidine-1-carboxylate
98. Thiazol-4-ylmethyl 4-[2-(biphenyl-3-yloxy)ethyl]-piperidine-1-carboxylate
99. Thiazol-4-ylmethyl 4-[2-(biphenyl-4-yloxy)ethyl]-piperidine-1-carboxylate
100. Thiazol-4-ylmethyl 4-[2-(4-chloro-2-cyanophenoxy)-ethyl]piperidine-1-carboxylate
101. Thiazol-4-ylmethyl 4-[2-(2-methylbenzothiazol-5-yloxy)ethyl]piperidine-1-carboxylate
102. Thiazol-4-ylmethyl 4-[2-(4'-cyanobiphenyl-4-yloxy)-ethyl]piperidine-1-carboxylate
103. Thiazol-4-ylmethyl 4-[2-(2-{morpholin-4-yl}phenoxy)-ethyl]piperidine-1-carboxylate and its trifluoroacetate
104. Thiazol-4-ylmethyl 4-[2-(4-chloro-2-{isoxazol-5-yl}-phenoxy)ethyl]piperidine-1-carboxylate
105. Thiazol-2-ylmethyl 4-[2-(4-{dimethylaminomethyl}-phenoxy)ethyl]piperidine-1-carboxylate and its trifluoroacetate
106. Thiazol-2-ylmethyl 4-[2-(naphth-2-yloxy)ethyl]-piperidine-1-carboxylate
107. Thiazol-2-ylmethyl 4-[2-(naphth-1-yloxy)ethyl]-piperidine-1-carboxylate
108. Thiazol-2-ylmethyl 4-[2-(7-methoxynaphth-2-yloxy)-ethyl]piperidine-1-carboxylate
109. Thiazol-4-ylmethyl 4-[2-(2-cyclopentylphenoxy)-ethyl]piperidine-1-carboxylate
110. Thiazol-4-ylmethyl 4-[2-(2-benzyloxyphenoxy)ethyl]-piperidine-1-carboxylate
111. Thiazol-4-ylmethyl 4-[2-(isoquinolin-7-yloxy)ethyl]-piperidine-1-carboxylate and its trifluoroacetate
112. Thiazol-4-ylmethyl 4-[2-(quinolin-5-yloxy)ethyl]-piperidine-1-carboxylate and its trifluoroacetate
113. Thiazol-4-ylmethyl 4-[2-(2-methylquinolin-6-yloxy)-ethyl]piperidine-1-carboxylate and its trifluoroacetate
114. Thiazol-4-ylmethyl 4-[2-(2-cyanoquinolin-8-yloxy)-ethyl]piperidine-1-carboxylate and its trifluoroacetate
115. Thiazol-4-ylmethyl 4-[2-(2,4-dichlorophenoxy)ethyl]-piperidine-1-carboxylate
116. Thiazol-4-ylmethyl 4-[2-(4-cyclopentylphenoxy)-ethyl]piperidine-1-carboxylate
117. Thiazol-4-ylmethyl 4-[2-(2-{benzoxazol-2-yl}-phenoxy)ethyl]piperidine-1-carboxylate
118. Thiazol-4-ylmethyl 4-[2-(4-cyano-3-fluorophenoxy)-ethyl]piperidine-1-carboxylate
119. Thiazol-4-ylmethyl 4-{2-[4-(1,1,3,3-tetramethyl-butyl)phenoxy]ethyl}piperidine-1-carboxylate
120. Thiazol-4-ylmethyl 4-[2-(4-{pyrrol-1-yl}phenoxy)-ethyl]piperidine-1-carboxylate and its trifluoroacetate
121. Thiazol-4-ylmethyl 4-[2-(3,5-di{tert-butyl}phenoxy)-ethyl]piperidine-1-carboxylate
122. Thiazol-4-ylmethyl 4-[2-(4-{dimethylaminomethyl}-phenoxy)ethyl]piperidine-1-carboxylate and its trifluoroacetate
123. Thiazol-4-ylmethyl 4-[2-(2-methylquinolin-8-yloxy)-ethyl]piperidine-1-carboxylate and its trifluoroacetate
124. Thiazol-4-ylmethyl 4-[2-(3-cyanophenoxy)ethyl]-piperidine-1-carboxylate
125. Thiazol-5-ylmethyl 4-(2-phenoxyethyl)piperidine-1-carboxylate
126. Thiazol-5-ylmethyl 4-[2-(biphenyl-4-yloxy)ethyl]-piperidine-1-carboxylate
127. Thiazol-5-ylmethyl 4-[2-(4-carbamoylphenoxy)ethyl]-piperidine-1-carboxylate
128. Thiazol-5-ylmethyl 4-[2-(4-fluorophenoxy)ethyl]-piperidine-1-carboxylate
129. Thiazol-5-ylmethyl 4-[2-(2,4-dimethylphenoxy)ethyl]-piperidine-1-carboxylate
130. Thiazol-5-ylmethyl 4-[2-(4-{dimethylaminomethyl}-phenoxy)ethyl]piperidine-1-carboxylate and its trifluoroacetate
131. Thiazol-5-ylmethyl 4-[2-(2,3-dichlorophenoxy)ethyl]-piperidine-1-carboxylate
132. Thiazol-5-ylmethyl 4-[2-(2,4-dichlorophenoxy)ethyl]-piperidine-1-carboxylate
133. Thiazol-5-ylmethyl 4-[2-(2,5-dichlorophenoxy)ethyl]-piperidine-1-carboxylate
134. Thiazol-5-ylmethyl 4-[2-(3,5-dichlorophenoxy)ethyl]-piperidine-1-carboxylate
135. Thiazol-5-ylmethyl 4-[2-(4-cyclopentylphenoxy)-ethyl]piperidine-1-carboxylate
136. Thiazol-5-ylmethyl 4-[2-(naphth-2-yloxy)ethyl]-piperidine-1-carboxylate
137. Thiazol-5-ylmethyl 4-[2-(naphth-1-yloxy)ethyl]-piperidine-1-carboxylate
138. Thiazol-5-ylmethyl 4-[2-(2-methylquinolin-8-yloxy)-ethyl]piperidine-1-carboxylate
139. Thiazol-5-ylmethyl 4-[2-(2-{benzoxazol-2-yl}-phenoxy)ethyl]piperidine-1-carboxylate
140. Thiazol-5-ylmethyl 4-[2-(4-{benzyloxy}phenoxy)-ethyl]piperidine-1-carboxylate
141. Thiazol-5-ylmethyl 4-[2-(4-sulphamoylphenoxy)ethyl]-piperidine-1-carboxylate 142. Thiazol-5-ylmethyl 4-[2-(isoquinolin-5-yloxy)ethyl]-piperidine-1-carboxylate
143. Thiazol-5-ylmethyl 4-[2-(4-{carbamoylmethyl}-phenoxy)ethyl]piperidine-1-carboxylate
144. Thiazol-5-ylmethyl 4-[2-(quinolin-7-yloxy)ethyl]-piperidine-1-carboxylate
145. Thiazol-5-ylmethyl 4-[2-(quinolin-6-yloxy)ethyl]-piperidine-1-carboxylate
146. Thiazol-5-ylmethyl 4-[2-(quinolin-8-yloxy)ethyl]-piperidine-1-carboxylate
147. Thiazol-5-ylmethyl 4-[2-(3-{dimethylamino}phenoxy)-ethyl]piperidine-1-carboxylate and its trifluoroacetate
148. Thiazol-5-ylmethyl 4-[2-(4-cyano-3-fluorophenoxy)-ethyl]piperidine-1-carboxylate
149. Thiazol-5-ylmethyl 4-[2-(biphenyl-2-yloxy)ethyl]-piperidine-1-carboxylate
150. Thiazol-5-ylmethyl 4-[2-(biphenyl-3-yloxy)ethyl]-piperidine-1-carboxylate
151. Thiazol-5-ylmethyl 4-[2-(3-{trifluoromethyl}-phenoxy)ethyl]piperidine-1-carboxylate
152. Thiazol-5-ylmethyl 4-[2-(4-benzylphenoxy)ethyl]-piperidine-1-carboxylate
153. Thiazol-5-ylmethyl 4-[2-(2-ethoxyphenoxy)ethyl]-piperidine-1-carboxylate
154. Thiazol-5-ylmethyl 4-[2-(2-cyclopentylphenoxy)-ethyl]piperidine-1-carboxylate
155. Thiazol-5-ylmethyl 4-{2-[4-(1-methyl-1-phenylethyl)-phenoxy]ethyl}piperidine-1-carboxylate
156. Thiazol-5-ylmethyl 4-[2-(4-phenoxyphenoxy)ethyl]-piperidine-1-carboxylate
157. Thiazol-5-ylmethyl 4-[2-(2-bromo-4-fluorophenoxy)-ethyl]piperidine-1-carboxylate
158. Thiazol-5-ylmethyl 4-[2-(4-{pyrrol-1-yl}phenoxy)-ethyl]piperidine-1-carboxylate
159. Thiazol-5-ylmethyl 4-[2-(3-cyanophenoxy)ethyl]-piperidine-1-carboxylate
160. Thiazol-5-ylmethyl 4-[2-(3,5-di{tert-butyl}phenoxy)-ethyl]piperidine-1-carboxylate
161. Thiazol-5-ylmethyl 4-[2-(2-benzylphenoxy)ethyl]-piperidine-1-carboxylate
162. Thiazol-5-ylmethyl 4-[2-(2-{benzyloxy}phenoxy)-ethyl]piperidine-1-carboxylate
163. Thiazol-5-ylmethyl 4-[2-(2-cyanoquinolin-8-yloxy)-ethyl]piperidine-1-carboxylate
164. Thiazol-5-ylmethyl 4-[2-(3-{methoxycarbonyl}naphth-2-yloxy)ethyl]piperidine-1-carboxylate
165. Thiazol-5-ylmethyl 4-[2-(3-phenoxyphenoxy)ethyl]-piperidine-1-carboxylate
166. Thiazol-5-ylmethyl 4-[2-(4-chloro-2-cyanophenoxy)-ethyl]piperidine-1-carboxylate
167. Thiazol-5-ylmethyl 4-[2-(isoquinolin-7-yloxy)ethyl]-piperidine-1-carboxylate
168. Thiazol-5-ylmethyl 4-[2-(4-{hexyloxy}phenoxy)ethyl]-piperidine-1-carboxylate
169. Thiazol-5-ylmethyl 4-[2-(3-butoxyphenoxy)ethyl]-piperidine-1-carboxylate
170. Thiazol-5-ylmethyl 4-[2-(4-chloro-5-isopropyl-2-methylphenoxy)ethyl]piperidine-1-carboxylate
171. Thiazol-5-ylmethyl 4-[2-(2-methylbenzothiazol-5-yloxy)ethyl]piperidine-1-carboxylate
172. Thiazol-5-ylmethyl 4-[2-(quinolin-5-yloxy)ethyl]-piperidine-1-carboxylate
173. Thiazol-5-ylmethyl 4-[2-(3-{pentafluoroethyl}-phenoxy)ethyl]piperidine-1-carboxylate
174. Thiazol-5-ylmethyl 4-[2-(5-bromo-2-chlorophenoxy)-ethyl]piperidine-1-carboxylate
175. Thiazol-5-ylmethyl 4-[2-(4-{difluoromethoxy}-phenoxy)ethyl]piperidine-1-carboxylate
176. Thiazol-5-ylmethyl 4-[2-(4'-cyanobiphenyl-3-yloxy)-ethyl]piperidine-1-carboxylate
177. Thiazol-5-ylmethyl 4-[2-(6-cyanonaphth-2-yloxy)-ethyl]piperidine-1-carboxylate
178. Thiazol-5-ylmethyl 4-[2-(4-{thiazol-2-yl}phenoxy)-ethyl]piperidine-1-carboxylate
179. Thiazol-5-ylmethyl 4-[2-(7-methoxynaphth-2-yloxy)-ethyl]piperidine-1-carboxylate
180. Thiazol-5-ylmethyl 4-[2-(4-chloro-2-{isoxazol-5-yl}-phenoxy)ethyl]piperidine-1-carboxylate
181. Thiazol-5-ylmethyl 4-[2-(2-carbamoyl-4-chloro-phenoxy)ethyl]piperidine-1-carboxylate
182. Thiazol-5-ylmethyl 4-[2-(5-{acetylamino}naphth-2-yloxy)ethyl]piperidine-1-carboxylate
183. Thiazol-5-ylmethyl 4-[2-(4'-cyanobiphenyl-4-yloxy)-ethyl]piperidine-1-carboxylate
184. Thiazol-5-ylmethyl 4-[2-(4-{methanesulphonyl}-phenoxy)ethyl]piperidine-1-carboxylate
185. Thiazol-5-ylmethyl 4-[2-(5-acetylamino-2-propyl-phenoxy)ethyl]piperidine-1-carboxylate
186. Thiazol-5-ylmethyl 4-[2-(1H-indol-6-yloxy)ethyl]-piperidine-1-carboxylate
187. Thiazol-5-ylmethyl 4-{2-[4-fluoro-2-(1H-pyrazol-3-yl)phenoxy]ethyl}piperidine-1-carboxylate
188. Thiazol-5-ylmethyl 4-[2-(4-cyano-2-fluorophenoxy)-ethyl]piperidine-1-carboxylate
189. Thiazol-5-ylmethyl 4-[2-(2-isopropyl-5-methyl-phenoxy)ethyl]piperidine-1-carboxylate
190. Thiazol-5-ylmethyl 4-[2-(2-{morpholin-4-yl}phenoxy)-ethyl]piperidine-1-carboxylate and its trifluoroacetate
191. Thiazol-5-ylmethyl 4-[2-(2-methylquinolin-6-yloxy)-ethyl]piperidine-1-carboxylate
192. Thiazol-5-ylmethyl 4-{2-[4-(2-oxopyrrolidin-1-yl)-phenoxy]ethyl}piperidine-1-carboxylate
193. Thiazol-5-ylmethyl 4-[2-(3-{tetrazol-1-yl}phenoxy)-ethyl]piperidine-1-carboxylate
194. Thiazol-2-ylmethyl (R)-3-(naphth-2-yloxymethyl)-pyrrolidine-1-carboxylate (enantiomer I)
195. Thiazol-2-ylmethyl (S)-3-(naphth-2-yloxymethyl)-pyrrolidine-1-carboxylate (enantiomer II)
196. Thiazol-2-ylmethyl (+/−)-3-(5-chloronaphth-2-yloxymethyl)pyrrolidine-1-carboxylate
197. Thiazol-2-ylmethyl (+/−)-3-(4'-fluorobiphenyl-4-yloxymethyl)pyrrolidine-1-carboxylate
198. 3-Carbamoylisoxazol-5-ylmethyl 4-[2-(4-fluorophenoxy)ethyl]piperidine-1-carboxylate
199. 3-Carbamoylisoxazol-5-ylmethyl 4-[2-(4-{trifluoromethoxy}phenoxy)ethyl]piperidine-1-carboxylate
200. 3-Carbamoylisoxazol-5-ylmethyl (−)-(R)-3-(naphth-2-yloxymethyl)pyrrolidine-1-carboxylate (enantiomer I)
201. 3-Carbamoylisoxazol-5-ylmethyl (+/−)-3-(6-methoxynaphth-2-yloxymethyl)pyrrolidine-1-carboxylate
202. 3-Carbamoylisoxazol-5-ylmethyl (+)-(S)-3-(naphth-2-yloxymethyl)pyrrolidine-1-carboxylate (enantiomer II).

The compounds of general formulae (I), (Ii) and (Iii) can comprise one or more asymmetric carbon atoms. They can exist in the form of enantiomers or diastereoisomers. These enantiomers and diastereoisomers and their mixtures, including the racemic mixtures, come within the invention.

The compounds of formulae (I), (Ii) and (Iii) can exist in the form of bases or of addition salts with acids. Such addition salts come within the invention.

These salts are advantageously prepared with pharmaceutically acceptable acids but the salts of other acids, for example of use in the purification or the isolation of the compounds of formulae (I), (Ii) and (Iii), also come within the invention.

The compounds of formulae (I), (Ii) and (Iii) and/or salts thereof may form solvates or hydrates and the invention includes all such solvates and hydrates.

The term <<hydrates>> and <<solvates>> mean that the compounds of formulae (I), (Ii) and (Iii) according to the invention can be combined or associated with one or more water or solvent molecules. This is only a chemical characteristic of such compounds, which can be applied for all organic compounds of this type.

In the context of the invention:
$C_{t-z}$, where t and z can take the values from 1 to 8, is understood to mean a carbon-comprising chain which can have from t to z carbon atoms, for example $C_{1-3}$ is understood to mean a carbon-comprising chain which can have from 1 to 3 carbon atoms;

alkyl is understood to mean a saturated and linear or branched aliphatic group; for example, a $C_{1-6}$-alkyl group represents a linear or branched carbon-comprising chain of 1 to 6 carbon atoms, more particularly a methyl, ethyl, propyl, isopropyl, butyl, isobutyl, tert-butyl, pentyl or hexyl;

alkylene is understood to mean a saturated and linear or branched divalent alkyl group; for example, a $C_{1-3}$-alkylene group represents a linear or branched divalent carbon-comprising chain of 1 to 3 carbon atoms, more particularly a methylene, ethylene, 1-methylethylene or propylene;

cycloalkyl is understood to mean a cyclic alkyl group; for example, a $C_{3-7}$-cycloalkyl group represents a cyclic carbon-comprising group of 3 to 7 carbon atoms, more particularly a cyclopropyl, cyclobutyl, cyclopentyl, cyclohexyl or cycloheptyl;

alkoxy is understood to mean an —O-alkyl group comprising a saturated and linear or branched aliphatic chain;

thioalkyl is understood to mean an —S-alkyl group comprising a saturated and linear or branched aliphatic chain;

haloalkyl is understood to mean an alkyl group, one or more hydrogen atoms of which have been replaced by a halogen atom;

haloalkoxy is understood to mean an alkoxy group, one or more hydrogen atoms of which have been replaced by a halogen atom;

halothioalkyl is understood to mean a thioalkyl group, one or more hydrogen atoms of which have been replaced by a halogen atom;

halogen atom is understood to mean a fluorine, a chlorine, a bromine or an iodine;

TFA is understood to mean trifluoroacetic acid;
ACN is understood to mean acetonitrile.

Within the meaning of the present invention, it should be noted that the terms "ranging from . . . to . . . " and "between . . . and . . . " mean that the limits are also considered.

The term <<preventing>>, as used herein, means reducing the risk of onset or slowing the occurrence of a given phenomenom, namely in the present invention, a pathology in which endogenous cannabinoids and/or other substrates metabolized by the enzyme FAAH are involved such as the pathologies as defined below.

Another subject-matter of the invention is targeted at a process for the preparation of the compounds of formula (I) according to the invention, comprising the stage consisting in reacting an amine derivative, a compound of following general formula (II):

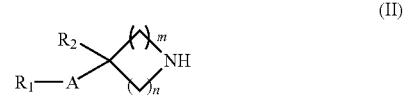

(II)

in which $R_1$, $R_2$, A, n and m are as defined in the formula (I) defined above, with a carbonate of following general formula (III):

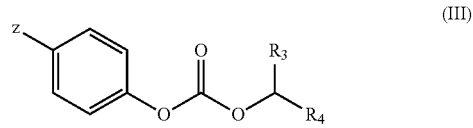

(III)

in which Z represents a hydrogen atom or a nitro group and $R_3$ and $R_4$ are as defined in the general formula (I) defined above, in the presence of a base, such as triethylamine, pyridine, N,N-dimethylaminopyridine or N,N-diisopropylethylamine, in an organic solvent, such as toluene, acetonitrile or dichloroethane, at a temperature between ambient temperature and the reflux temperature of the solvent.

In addition, the compounds of the invention can be prepared according to different methods illustrated by the following schemes. These methods and the intermediate compounds used are also a subject-matter of the present invention.

If appropriate, a compound of formula (II) can be protected, in particular at its amine functional group, according to methods well known to a person skilled in the art.

Mention may be made, as examples of protective groups and also of protecting and deprotecting methods, of the work "*Protective Groups in Organic Synthesis*", Green et al., $2^{nd}$ Edition (John Wiley & Sons, Inc., New York).

A preparation process employing a protected compound of formula (II) is, for example, described in the following Scheme 1.

As regards more particularly the compounds of general formula (I) in which A more particularly represents an oxygen atom or an —O—$C_{1-6}$-alkylene group, they can also be prepared according to the procedure described in the following Scheme 1.

Scheme 1

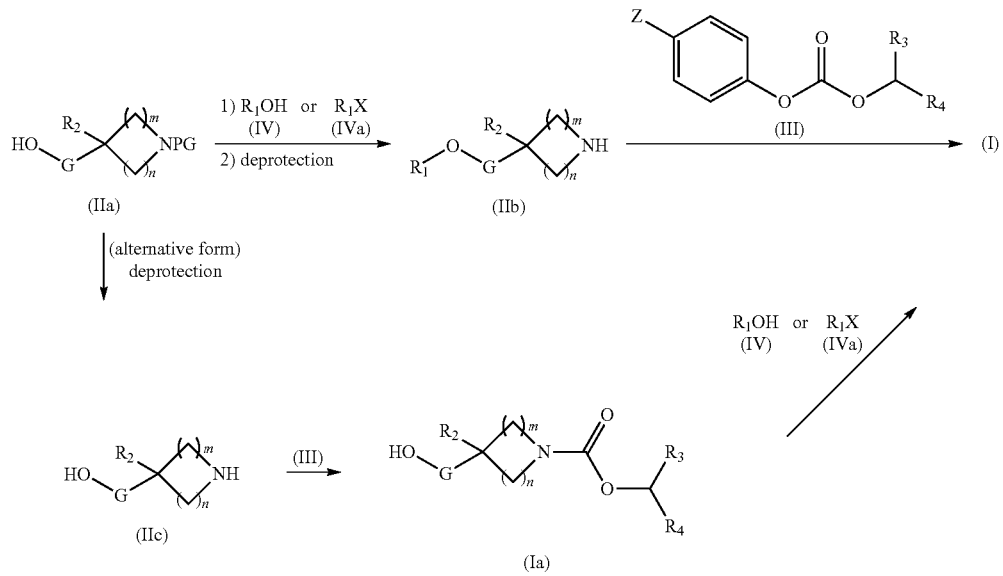

This preparation method (Scheme 1) consists in reacting, in a first step, an alcohol of general formula (IIa), in which $R_2$, m and n are as defined in the general formula (I) as defined above, G represents a portion of the group A as defined in the general formula (I), namely either a covalent bond or the $C_{1-6}$-alkylene portion of the —O—$C_{1-6}$-alkylene group, and PG represents a protective group, such as a Boc (tert-butyloxycarbonyl), a Cbz (benzyloxycarbonyl), a benzyl or a benzhydryl;

- either with an alcohol derivative of general formula (IV), in which $R_1$ is as defined above, using the Mitsunobu reaction conditions (*Synthesis*, 1981, 1-28),
- or with a halogenated derivative of general formula (IVa), in which $R_1$ is as defined above and X represents a fluorine, chlorine, bromine or iodine atom, using aromatic or heteroaromatic nucleophilic substitution reactions or Buchwald O-arylation or O-heteroarylation reactions, for example using a palladium or copper catalyst;

followed by a deprotection reaction, for example in the presence of trifluoroacetic acid or of a solution of hydrochloric acid in isopropanol or dioxane, to result in the amine of general formula (IIb) in which G, $R_2$, m and n are as defined in the amine of formula (IIa) above and $R_1$ is as defined in the general formula (I) as defined above. An alternative to the Mitsunobu reaction consists in reacting an alcohol derivative of general formula (IV) with a compound said to be of general formula (IIe) and deriving from the activation by a tosylate group of the alcohol functional group of a compound of general formula (IIa). The derivative of general formula (IIb) thus obtained is subsequently converted to the compound of general formula (I) according to a condensation reaction with a carbonate of general formula (III) as defined above, under the conditions described above.

An alternative form of producing the compounds of general formula (I) (Scheme 1) in which A more particularly represents an oxygen atom or an —O—$C_{1-6}$-alkylene group consists in deprotecting an alcohol of general formula (IIa) as defined above, according to a deprotection reaction as defined above, in order to obtain an aminoalcohol of general formula (IIc), and in then reacting this aminoalcohol of general formula (IIc) in which $R_2$, m and n are as defined in the general formula (I) defined above and G represents a portion of the group A as defined in the general formula (I), namely either a covalent bond or the $C_{1-6}$-alkylene portion of the —O—$C_{1-6}$-alkylene group, with a carbonate of general formula (III) as defined above under the conditions described above, to result in the carbamate derivative of general formula (Ia) in which $R_2$, $R_3$, $R_4$, m and n are as defined in the general formula (I) defined above and G represents a portion of the group A as defined in the general formula (I), namely either a covalent bond or the $C_{1-6}$-alkylene portion of the —O—$C_{1-6}$-alkylene group. The carbamate derivative (Ia) thus obtained is subsequently converted to the compound of general formula (I) by the action of an alcohol of general formula $R_1OH$ (IV) as defined above by using the Mitsunobu reaction conditions or by the action of a halogenated derivative of general formula $R_1X$ (IVa) as defined above by using aromatic or heteroaromatic nucleophilic substitution reactions or Buchwald O-arylation or O-heteroarylation reactions, for example using a palladium or copper catalyst.

As regards more particularly the compounds of general formula (I) in which $R_1$ represents an $R_5$ group substituted in particular by an $R_6$ group of $C_{1-6}$-alkyl, $C_{3-7}$-cycloalkyl or $C_{3-7}$-cycloalkyl-$C_{1-3}$-alkylene type or by an $R_7$ group as defined in the general formula (I) defined above, they can also be prepared according to the procedure described in the following Scheme 2.

Scheme 2

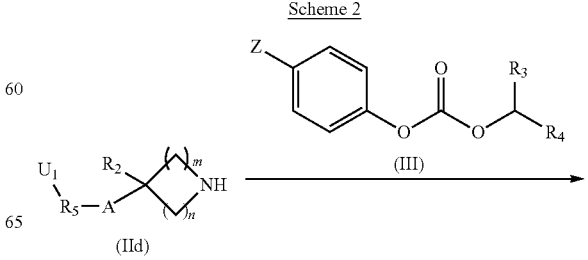

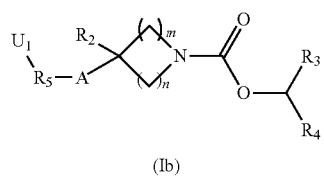

(Ib)

↓ Suzuki or Stille or Negishi (I)

Thus, the first stage consists in reacting an amine of general formula (IId), in which A, $R_2$, $R_5$, m and n are as defined in the general formula (I) defined above and $U_1$ represents a chlorine, bromine or iodine atom or a triflate group, with a carbonate of general formula (III) as defined above under the conditions described above, to result in the carbamate derivative of general formula (Ib) in which A, $R_2$, $R_3$, $R_4$, $R_5$, m and n are as defined in the general formula (I) defined above and $U_1$ is as defined above. The coupling reaction catalysed by means of a transition metal, such as palladium(0), is subsequently carried out on the key intermediate of general formula (Ib) as defined above, $U_1$ being in the position where it is desired to introduce the $R_6$ or $R_7$ group (Scheme 2):

- either by a reaction of Suzuki type, for example using an alkyl-, cycloalkyl-, aryl- or heteroarylboronic acid,
- or according to a reaction of Stille type, for example using a trialkylaryltin or trialkylheteroaryltin derivative,
- or by a reaction of Negishi type, for example using an alkyl-, cycloalkyl-, aryl- or heteroarylzinc halide derivative.

Alternatively, the other compounds of general formulae (II), (IIa), (IIb), (IIc), (IId), (III), (IV) and (IVa) and the other reactants are commercially available or are described in the literature or else can be prepared according to methods which are described therein or which are known to a person skilled in the art.

Another subject-matter of the present invention is the compounds of general formula (Ia):

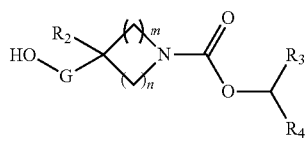

(Ia)

in which $R_2$, $R_3$, $R_4$, m and n are as defined in the general formula (I) and G represents a portion of the group A as defined in the general formula (I), namely either a covalent bond or the $C_{1-6}$-alkylene portion of the —O—$C_{1-6}$-alkylene group.

Mention may be made, among these compounds, of:
thiazol-2-ylmethyl 4-(2-hydroxyethyl)piperidine-1-carboxylate
thiazol-4-ylmethyl 3-(hydroxymethyl)pyrrolidine-1-carboxylate.

Another subject-matter of the present invention is the compounds of general formula (II):

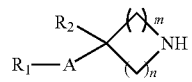

(II)

in which A, $R_1$, $R_2$, m and n are as defined in the general formula (I).

Mention may be made, among these compounds, of:
4-[2-(4-chloronaphth-1-yloxy)ethyl]piperidine
3-(6-methoxynaphth-2-yloxymethyl)pyrrolidine
3'-(pyrrolidin-3-ylmethoxy)biphenyl-3-carbonitrile
3-(5-chloronaphth-2-yloxymethyl)pyrrolidine
3-(3-{trifluoromethoxy}phenoxymethyl)pyrrolidine
3-[4-(1-methyl-1-phenylethyl)phenoxymethyl]pyrrolidine
7-(pyrrolidin-3-ylmethoxy)quinoline
3-(pyrrolidin-3-ylmethoxy)quinoline
3-(4-chloro-3-{trifluoromethyl}phenoxymethyl)-pyrrolidine
7-(pyrrolidin-3-ylmethoxy)isoquinoline
3-(5-fluoronaphth-2-yloxymethyl)pyrrolidine
3-(4'-fluorobiphenyl-4-yloxymethyl)pyrrolidine The following examples illustrate the preparation of some compounds of the invention. These examples are not limiting and serve only to illustrate the invention. The NMR spectra and/or the LC-MS (Liquid Chromatography-Mass Spectroscopy) confirm the structures and the purities of the compounds obtained.

M.p. (° C.) represents the melting point in degrees Celsius.

$R_f$ indicates the retention time obtained by TLC (Thin Layer Chromatography) analysis.

The numbers shown in brackets in the titles of the examples correspond to those in the 1st column of the tables below.

The IUPAC (International Union of Pure and Applied Chemistry) nomenclature was used in the naming of the compounds in the examples below.

EXAMPLE 1

Compound No. 17

Thiazol-4-ylmethyl 3-(naphth-2-yloxymethyl)pyrrolidine-1-carboxylate

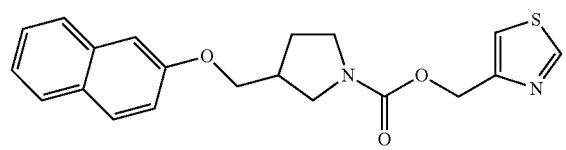 [SMILES: O=C(OCc1cscn1)N1CCC(COc2ccc3ccccc3c2)C1]

1.1 Thiazol-4-ylmethyl 3-(hydroxymethyl)pyrrolidine-1-carboxylate

A solution of 3.00 g (10.70 mmol) of thiazol-4-ylmethyl 4-nitrophenyl carbonate in 20 ml of dichloromethane is added at ambient temperature, via a dropping funnel, to a solution of 1.13 g (11.24 mmol) of pyrrolidin-3-ylmethanol (commercial) in 20 ml of methanol. The solution is stirred for 15 hours. Water is subsequently added to the reaction medium. After extraction of the aqueous phase with dichloromethane, the organic phases are successively washed with a 1M aqueous sodium hydroxide solution and then with a saturated aqueous sodium chloride solution. After having dried the organic phases over sodium sulphate, the mixture is filtered and the filtrate is evaporated to dryness. 0.56 g of the desired product is thus obtained in the form of an oil after purification on a column of silica gel, elution being carried out with a dichloromethane/methanol (97/3 to 95/5) mixture.

1.2 Thiazol-4-ylmethyl 3-(naphth-2-yloxymethyl)pyrrolidine-1-carboxylate 0.25 g (1.03 mmol) of thiazol-4-ylmethyl 3-(hydroxymethyl)pyrrolidine-1-carboxylate is dissolved in 8 ml of toluene. 0.35 g (1.34 mmol) of triphenylphosphine and 0.16 g (1.13 mmol) of naphth-2-ol are added and then the medium is cooled to 0° C. for slow addition of a solution of 0.27 g (1.34 mmol) of diisopropyl azodicarboxylate in 2 ml of toluene. The medium is stirred at ambient temperature for 14 hours. The residue obtained is taken up in water and extracted twice with dichloromethane. The combined organic phases are washed with a saturated aqueous sodium chloride solution, dried over sodium sulphate, filtered and concentrated under vacuum. The residue is purified by chromatography on silica gel, elution being carried out with a 99/1 to 98/2 mixture of dichloromethane and methanol. 0.15 g of the expected product is obtained in the form of a powder.

M.p. (° C.): 90-92
LC-MS: M+H=369
$^1$H NMR (d$_6$-DMSO) δ (ppm): 9.10 (s, 1H); 7.85 (m, 3H); 7.70 (m, 1H); 7.50 (m, 1H); 7.35 (m, 2H); 7.20 (m, 1H); 5.20 (s, 2H); 4.10 (m, 2H); 3.60 (m, 1H); 3.50 (m, 1H); 3.40 (m, 1H); 3.30 (m, 1H); 2.70 (m, 1H); 2.10 (m, 1H); 1.80 (m, 1H)

EXAMPLE 2

Compound No. 22

Thiazol-4-ylmethyl 3-(4'-fluorobiphenyl-4-yloxymethyl)-pyrrolidine-1-carboxylate

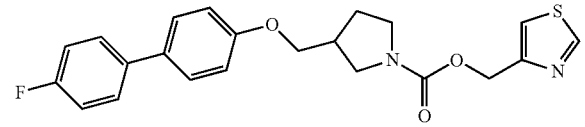 [SMILES: O=C(OCc1cscn1)N1CCC(COc2ccc(-c3ccc(F)cc3)cc2)C1]

2.1 tert-Butyl 3-(4'-fluorobiphenyl-4-yloxymethyl)-pyrrolidine-1-carboxylate

The procedure is the same as for Example 1 (Stage 1.2) starting from 1.50 g (7.45 mmol) of tert-butyl 3-(hydroxymethyl)pyrrolidine-1-carboxylate (commercial), 2.15 g (11.18 mmol) of 4'-fluorobiphenyl-4-ol, 2.93 g (11.18 mmol) of triphenylphosphine and 2.26 g (11.18 mmol) of diisopropyl azodicarboxylate. After purification by chromatography on a column of silica gel, elution being carried out with dichloromethane, 1.55 g of the expected product are obtained in the form of an oil.

2.2 3-(4'-Fluorobiphenyl-4-yloxymethyl)pyrrolidine 1.55 g (4.17 mmol) of tert-butyl 3-(4'-fluorobiphenyl-4-yloxymethyl)pyrrolidine-1-carboxylate are dissolved in 40 ml of dichloromethane and then, at 0° C., 6.00 ml (80.77 mmol) of trifluoroacetic acid are subsequently added. After stirring at ambient temperature for two hours, the mixture is concentrated to dryness and then the residue is taken up in water and dichloromethane. A saturated sodium hydrogencarbonate solution is added and then the aqueous phase is extracted with dichloromethane. The combined organic phases are washed with a saturated aqueous sodium chloride solution, dried over sodium sulphate, filtered and concentrated under vacuum. 0.98 g of product is obtained in the form of an oil, used as is in the following stage.

2.3 Thiazol-4-ylmethyl 3-(4'-fluorobiphenyl-4-yloxymethyl)-pyrrolidine-1-carboxylate 0.30 g (1.07 mmol) of thiazol-4-ylmethyl 4-nitrophenyl carbonate, 0.34 g (1.28 mmol) of 3-(4'-fluorobiphenyl-4-yloxymethyl)pyrrolidine, 0.20 g (1.61 mmol) of N,N-diisopropylethylamine and 0.01 g (0.11 mmol) of dimethylaminopyridine are dissolved in 10 ml of 1,2-dichloroethane. The mixture is stirred at 70° C. for 4 hours. After returning to ambient temperature, water is added to the reaction medium. After extraction of the aqueous phase with dichloromethane, the organic phases are successively washed three times with a 1M aqueous sodium hydroxide solution and then twice with a saturated aqueous ammonium chloride solution. After having dried the organic phases over sodium sulphate, they are filtered and the filtrate is evaporated to dryness. After purification by chromatography on a column of silica gel, elution being carried out with dichloromethane and methanol (98/2), 0.16 g of the expected product is obtained in the form of a powder.

M.p. (° C.): 115-117
LC-MS: M+H=413
$^1$H NMR (d$_6$-DMSO) δ (ppm): 9.10 (s, 1H); 7.70 (m, 3H); 7.60 (d, 2H); 7.30 (m, 2H); 7.05 (m, 2H); 5.20 (s, 2H); 4.05 (m, 2H); 3.60 (m, 1H); 3.50 (m, 1H); 3.35 (m, 1H); 3.20 (m, 1H); 2.70 (m, 1H); 2.10 (m, 1H); 1.80 (m, 1H)

EXAMPLE 3

Compound No. 200

3-Carbamoylisoxazol-5-ylmethyl (−)-(R)-3-(naphth-2-yloxymethyl)pyrrolidine-1-carboxylate

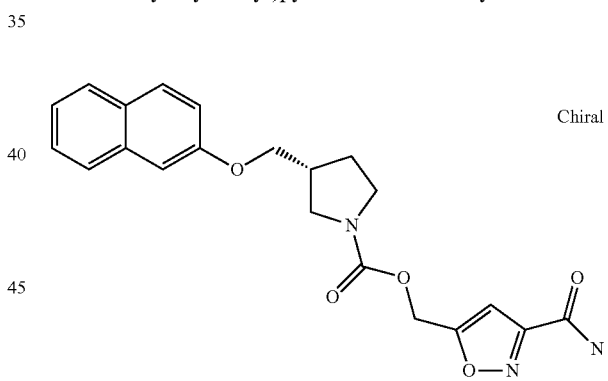

3.1 tert-Butyl (R)-3-(naphth-2-yloxymethyl)pyrrolidine-1-carboxylate

The procedure is the same as for Example 1 (Stage 1.2) starting from 2.00 g (9.94 mmol) of tert-butyl (R)-3-(hydroxymethyl)pyrrolidine-1-carboxylate (commercial), 2.00 g (13.91 mmol) of naphth-2-ol, 3.90 g (14.91 mmol) of triphenylphosphine and 3.01 g (14.91 mmol) of diisopropyl azodicarboxylate. 1.75 g of product are obtained in the form of an oil after purification on a column of silica gel, elution being carried out with dichloromethane.

3.2 (R)-3-(naphth-2-yloxymethyl)pyrrolidine

The procedure is the same as for Example 2 (Stage 2.2) starting from 1.75 g (5.34 mmol) of tert-butyl (R)-3-(naphth-2-yloxymethyl)pyrrolidine-1-carboxylate and 5.00 ml (67.31 mmol) of trifluoroacetic acid. 1.20 g of product are obtained in the form of an oil.

3.3 3-Carbamoylisoxazol-5-ylmethyl 4-nitrophenyl carbonate 2.84 g (14.07 mmol) of 4-nitrophenyl chloroformate are added in small portions to a solution, cooled to approximately 0° C., of 2.00 g (14.07 mmol) of 3-carbamoylisoxazol-5-ylmethanol, 1.71 ml (21.11 mmol) of pyridine and 0.17 g (1.41 mmol) of N,N-dimethylaminopyridine in 15 ml of dichloromethane. The medium is kept stirred at 0° C. for 1 hour and then at ambient temperature for 1 hour. The precipitate formed is filtered off and then copiously rinsed with diisopropyl ether. After drying under vacuum at approximately 60° C., 3.12 g (72%) of the expected product are obtained in the form of a white solid used as is in the following stage.

M.p. (° C.): 143-145

$^1$H NMR (d$_6$-DMSO, 400 MHz) δ (ppm): 8.40 (d, 2H); 8.25 (broad s, 1H); 7.90 (broad s, 1H); 7.65 (d, 2H); 7.0 (s, 1H); 5.50 (s, 2H).

3.4 3-Carbamoylisoxazol-5-ylmethyl (−)-(R)-3-(naphth-2-yloxymethyl)pyrrolidine-1-carboxylate 0.21 g (0.92 mmol) of (R)-3-(naphth-2-yloxymethyl)-pyrrolidine is dissolved in 3.80 ml of dichloromethane and then 0.31 g (1.01 mmol) of 3-carbamoylisoxazol-5-ylmethyl 4-nitrophenyl carbonate and 0.15 ml (1.38 mmol) of N-methylmorpholine are added. The mixture is stirred at ambient temperature for 20 hours and then water is added to the reaction medium. After extraction of the aqueous phase with dichloromethane, the organic phases are successively washed three times with a 1M aqueous sodium hydroxide solution and then twice with a saturated aqueous ammonium chloride solution. After having dried the organic phases over sodium sulphate, they are filtered and the filtrate is evaporated to dryness. 0.14 g of the desired product is thus obtained in the form of a white solid after purification on a column of silica gel, elution being carried out with a dichloromethane/methanol mixture, and then taken up in isopropyl ether.

M.p. (° C.): 138-140

LC-MS: M+H=396

$^1$H NMR (d$_6$-DMSO) δ (ppm): 8.15 (broad s, 1H); 7.80 (m, 4H); 7.50 (m, 1H); 7.35 (m, 2H); 7.20 (m, 1H); 6.80 (s, 1H); 5.30 (s, 2H); 4.10 (m, 2H); 3.65 (m, 1H); 3.50 (m, 1H); 3.40 (m, 1H); 3.30 (m, 1H); 2.80 (m, 1H); 2.10 (m, 1H); 1.85 (m, 1H) [α]$^{20° C.}$ −7.917° (c=0.312; DMSO, 589 nm)

EXAMPLE 4

Compound No. 202

3-Carbamoylisoxazol-5-ylmethyl (+)-(S)-3-(naphth-2-yloxymethyl)pyrrolidine-1-carboxylate

4.1 tert-Butyl (S)-3-(naphth-2-yloxymethyl)pyrrolidine-1-carboxylate

The procedure is the same as for Example 1 (Stage 1.2) starting from 2.00 g (9.94 mmol) of tert-butyl (S)-3-(hydroxymethyl)pyrrolidine-1-carboxylate (commercial), 2.00 g (13.91 mmol) of naphth-2-ol, 3.90 g (14.91 mmol) of triphenylphosphine and 3.01 g (14.91 mmol) of diisopropyl azodicarboxylate. 2.80 g of product are obtained in the form of an oil after purification on a column of silica gel, elution being carried out with dichloromethane.

4.2 (S)-3-(Naphth-2-yloxymethyl)pyrrolidine

The procedure is the same as for Example 2 (Stage 2.2) starting from 1.75 g (5.34 mmol) of tert-butyl (S)-3-(naphth-2-yloxymethyl)pyrrolidine-1-carboxylate and 5.00 ml (67.31 mmol) of trifluoroacetic acid. The product is obtained in the form of an oil after purification on a column of silica gel, elution being carried out with a dichloromethane/methanol/aqueous ammonia (90/9/1) mixture.

4.3 3-Carbamoylisoxazol-5-ylmethyl (+)-(S)-3-(naphth-2-yloxymethyl)pyrrolidine-1-carboxylate The procedure is the same as for Example 3 (Stage 3.4) starting from 0.21 g (0.95 mmol) of (S)-3-(naphth-2-yloxymethyl)pyrrolidine, 0.32 g (1.04 mmol) of 3-carbamoylisoxazol-5-ylmethyl 4-nitrophenyl carbonate (Stage 4.3) and 0.16 ml (1.42 mmol) of N-methylmorpholine. 0.21 g of a powder is obtained after purification on a column of silica gel, elution being carried out with a dichloromethane/methanol mixture, and trituration from isopropyl ether.

M.p. (° C.): 139-141

LC-MS: M+H=396

$^1$H NMR (d$_6$-DMSO) δ (ppm): 8.15 (broad s, 1H); 7.80 (m, 4H); 7.50 (m, 1H); 7.35 (m, 2H); 7.20 (m, 1H); 6.80 (s, 1H); 5.30 (s, 2H); 4.10 (m, 2H); 3.65 (m, 1H); 3.50 (m, 1H); 3.40 (m, 1H); 3.30 (m, 1H); 2.80 (m, 1H); 2.10 (m, 1H); 1.85 (m, 1H) [α]$^{20° C.}$ +9.944° (c=0.036; DMSO, 589 nm)

The chemical structures and the physical properties of some compounds according to the invention are illustrated in the following Table 1. In this table, the compounds are in the free base or salt form.

*A represents an —O—C$_{1-6}$-alkylene group in which the end represented by an oxygen atom is bonded to the R$_1$ group.

TABLE 1

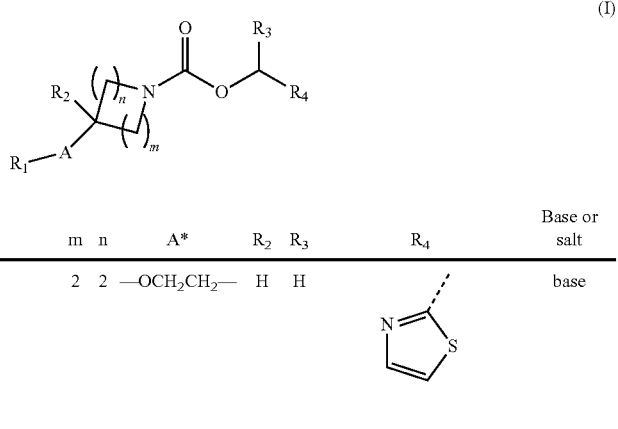

(I)

| N° | R$_1$ | m | n | A* | R$_2$ | R$_3$ | R$_4$ | Base or salt |
|---|---|---|---|---|---|---|---|---|
| 1. | ![Cl-naphthyl] | 2 | 2 | —OCH$_2$CH$_2$— | H | H | ![thiazolyl] | base |

TABLE 1-continued (I)

| N° | R₁ | m | n | A* | R₂ | R₃ | R₄ | Base or salt |
|---|---|---|---|---|---|---|---|---|
| 2. | 4-F-phenyl | 2 | 2 | —OCH₂CH₂— | H | H | thiazol-2-yl | base |
| 3. | 4-F-phenyl | 2 | 2 | —OCH₂CH₂— | H | H | thiazol-4-yl | base |
| 4. | 4-CF₃-phenyl | 2 | 2 | —OCH₂CH₂— | H | H | thiazol-4-yl | base |
| 5. | 4-Cl-phenyl | 2 | 2 | —OCH₂CH₂— | H | H | thiazol-4-yl | base |
| 6. | 4-F-phenyl | 2 | 2 | —OCH₂CH₂— | H | H | thiazol-5-yl | base |
| 7. | 4-Cl-phenyl | 2 | 2 | —OCH₂CH₂— | H | H | thiazol-5-yl | base |
| 8. | 4-CF₃-phenyl | 2 | 2 | —OCH₂CH₂— | H | H | thiazol-5-yl | base |
| 9. | 6-OMe-naphth-2-yl | 2 | 2 | —OCH₂CH₂— | H | H | thiazol-4-yl | base |
| 10. | 4-CN-phenyl | 2 | 2 | —OCH₂CH₂— | H | H | thiazol-4-yl | base |

TABLE 1-continued
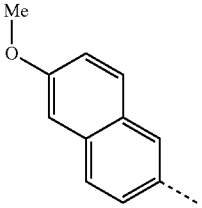
(I)
| N° | R₁ | m | n | A* | R₂ | R₃ | R₄ | Base or salt |
|---|---|---|---|---|---|---|---|---|
| 11. | 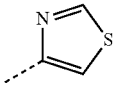 | 2 | 1 | —OCH₂— | H | H | 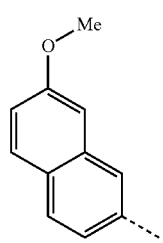 (+/−) | base |
| 12. | 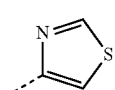 | 2 | 1 | —OCH₂— | H | H | 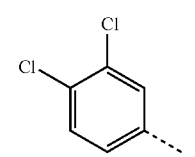 (+/−) | base |
| 13. | 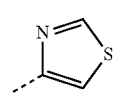 | 2 | 1 | —OCH₂— | H | H | 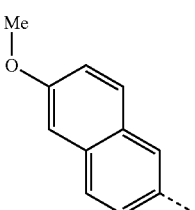 (+/−) | base |
| 14. | 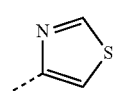 | 2 | 2 | —OCH₂CH₂— | H | H | 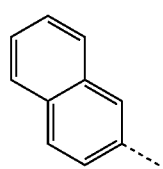 | base |
| 15. | 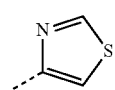 | 2 | 2 | —OCH₂CH₂— | H | H | 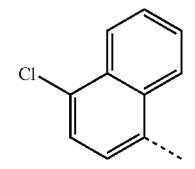 | base |
| 16. | 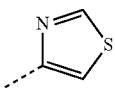 | 1 | 2 | —OCH₂— | H | H | 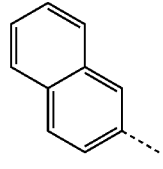 (+/−) | base |
| 17. | 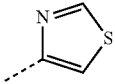 | 1 | 2 | —OCH₂— | H | H | 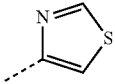 (+/−) | base |

TABLE 1-continued
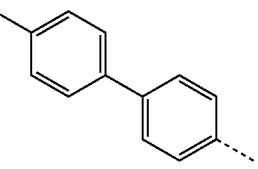
(I)
| N° | R₁ | m | n | A* | R₂ | R₃ | R₄ | Base or salt |
|---|---|---|---|---|---|---|---|---|
| 18. | 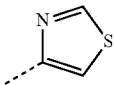 | 2 | 2 | —OCH₂CH₂— | H | H | 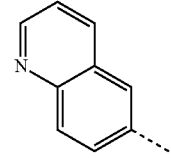 | base |
| 19. | 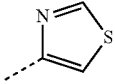 | 2 | 2 | —OCH₂CH₂— | H | H | 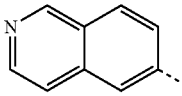 | HCl |
| 20. | 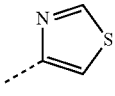 | 2 | 2 | —OCH₂CH₂— | H | H | 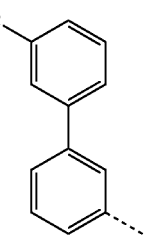 | HCl |
| 21. | 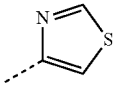 | 1 | 2 | —OCH₂— | H | H | 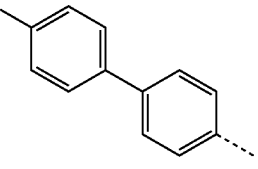<br>(+/−) | base |
| 22. | 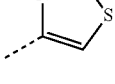 | 1 | 2 | —OCH₂— | H | H | 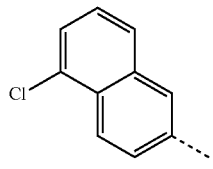<br>(+/−) | base |
| 23. | 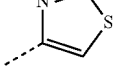 | 1 | 2 | —OCH₂— | H | H | 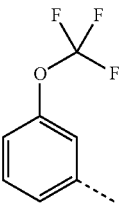<br>(+/−) | base |
| 24. | 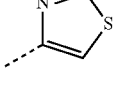 | 1 | 2 | —OCH₂— | H | H | <br>(+/−) | base |

TABLE 1-continued
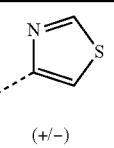
(I)
| N° | R₁ | m | n | A* | R₂ | R₃ | R₄ | Base or salt |
|---|---|---|---|---|---|---|---|---|
| 25. | 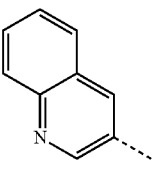 | 1 | 2 | —OCH₂— | H | H | 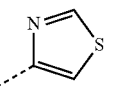<br>(+/−) | base |
| 26. | 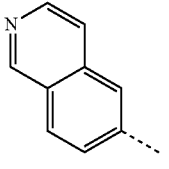 | 1 | 2 | —OCH₂— | H | H | 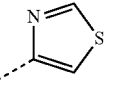<br>(+/−) | base |
| 27. | 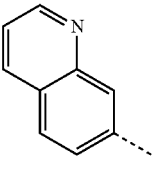 | 1 | 2 | —OCH₂— | H | H | 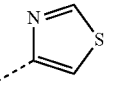<br>(+/−) | base |
| 28. | 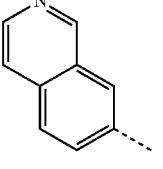 | 1 | 2 | —OCH₂— | H | H | 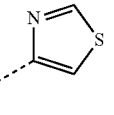<br>(+/−) | base |
| 29. | 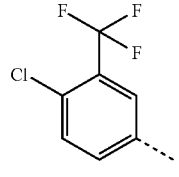 | 1 | 2 | —OCH₂— | H | H | 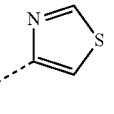<br>(+/−) | base |
| 30. | 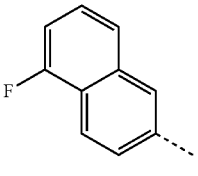 | 1 | 2 | —OCH₂— | H | H | 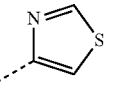<br>(+/−) | base |
| 31. | 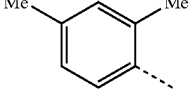 | 1 | 2 | —OCH₂— | H | H | 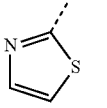<br>(+/−) | base |
| 32. | Me⟋⟍Me | 2 | 2 | —OCH₂CH₂— | H | H | | base |

TABLE 1-continued
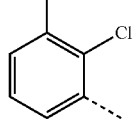
(I)
| N° | R₁ | m | n | A* | R₂ | R₃ | R₄ | Base or salt |
|---|---|---|---|---|---|---|---|---|
| 33. | 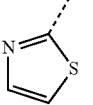 | 2 | 2 | —OCH₂CH₂— | H | H | 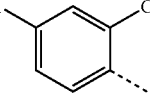 | base |
| 34. |  | 2 | 2 | —OCH₂CH₂— | H | H | 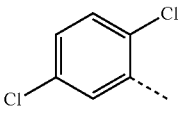 | base |
| 35. | 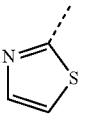 | 2 | 2 | —OCH₂CH₂— | H | H | 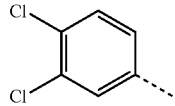 | base |
| 36. |  | 2 | 2 | —OCH₂CH₂— | H | H | 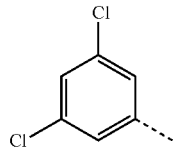 | base |
| 37. | 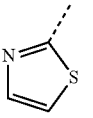 | 2 | 2 | —OCH₂CH₂— | H | H | 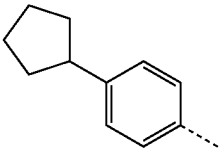 | base |
| 38. |  | 2 | 2 | —OCH₂CH₂— | H | H | 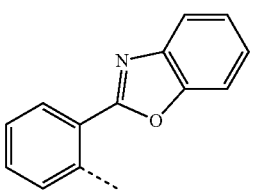 | base |
| 39. | 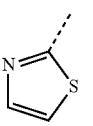 | 2 | 2 | —OCH₂CH₂— | H | H | 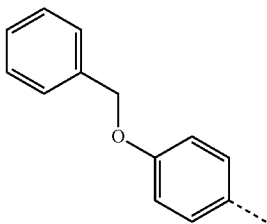 | base |
| 40. | 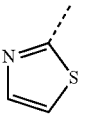 | 2 | 2 | —OCH₂CH₂— | H | H |  | base |

TABLE 1-continued

Formula (I): carbamate structure with R1-A-, R2, (CH2)n, (CH2)m, N-C(=O)-O-CH(R3)(R4)

| N° | R1 | m | n | A* | R2 | R3 | R4 | Base or salt |
|---|---|---|---|---|---|---|---|---|
| 41. | 4-(H2N-C(=O)-CH2)-phenyl | 2 | 2 | —OCH2CH2— | H | H | thiazol-2-yl | base |
| 42. | quinolin-7-yl | 2 | 2 | —OCH2CH2— | H | H | thiazol-2-yl | CF3CO2H |
| 43. | quinolin-6-yl | 2 | 2 | —OCH2CH2— | H | H | thiazol-2-yl | CF3CO2H |
| 44. | 4-cyano-3-fluorophenyl | 2 | 2 | —OCH2CH2— | H | H | thiazol-2-yl | base |
| 45. | biphenyl-2-yl | 2 | 2 | —OCH2CH2— | H | H | thiazol-2-yl | base |
| 46. | 4-methyl-2-(1-methylethyl)phenyl (2,4-dimethyl... ) | 2 | 2 | —OCH2CH2— | H | H | thiazol-2-yl | base |
| 47. | 3-(trifluoromethyl)phenyl | 2 | 2 | —OCH2CH2— | H | H | thiazol-2-yl | base |

TABLE 1-continued (I)

| N° | R₁ | m | n | A* | R₂ | R₃ | R₄ | Base or salt |
|---|---|---|---|---|---|---|---|---|
| 48. | 4-(2,4,4-trimethylpentan-2-yl)phenyl | 2 | 2 | —OCH₂CH₂— | H | H | thiazol-2-yl | base |
| 49. | 4-benzylphenyl | 2 | 2 | —OCH₂CH₂— | H | H | thiazol-2-yl | base |
| 50. | 4-(1H-pyrrol-1-yl)phenyl | 2 | 2 | —OCH₂CH₂— | H | H | thiazol-2-yl | CF₃CO₂H |
| 51. | 4-carbamoylphenyl | 2 | 2 | —OCH₂CH₂— | H | H | thiazol-2-yl | base |
| 52. | 3-cyanophenyl | 2 | 2 | —OCH₂CH₂— | H | H | thiazol-2-yl | base |
| 53. | 3,5-di-tert-butylphenyl | 2 | 2 | —OCH₂CH₂— | H | H | thiazol-2-yl | base |
| 54. | 2-benzylphenyl | 2 | 2 | —OCH₂CH₂— | H | H | thiazol-2-yl | base |

TABLE 1-continued
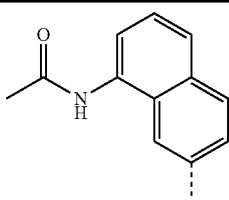
(I)
| N° | R₁ | m | n | A* | R₂ | R₃ | R₄ | Base or salt |
|---|---|---|---|---|---|---|---|---|
| 55. | 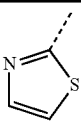 | 2 | 2 | —OCH₂CH₂— | H | H | 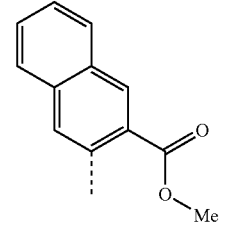 | base |
| 56. | 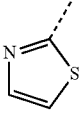 | 2 | 2 | —OCH₂CH₂— | H | H | 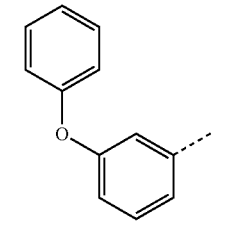 | base |
| 57. | 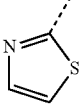 | 2 | 2 | —OCH₂CH₂— | H | H | 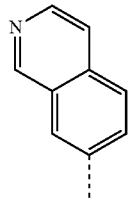 | base |
| 58. | 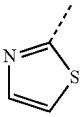 | 2 | 2 | —OCH₂CH₂— | H | H | 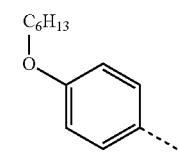 | CF₃CO₂H |
| 59. | 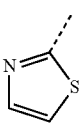 | 2 | 2 | —OCH₂CH₂— | H | H | 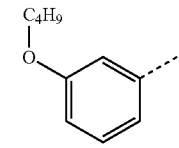 | base |
| 60. | 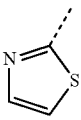 | 2 | 2 | —OCH₂CH₂— | H | H | 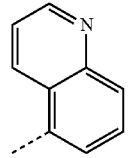 | base |
| 61. | 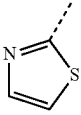 | 2 | 2 | —OCH₂CH₂— | H | H | | CF₃CO₂H |

TABLE 1-continued (I)

| N° | R₁ | m | n | A* | R₂ | R₃ | R₄ | Base or salt |
|---|---|---|---|---|---|---|---|---|
| 62. | 3-(pentafluoroethyl)phenyl | 2 | 2 | —OCH₂CH₂— | H | H | thiazol-2-yl | base |
| 63. | 6-(acetamido)naphthalen-2-yl (1-acetamidonaphthalen-6-yl) | 2 | 2 | —OCH₂CH₂— | H | H | thiazol-2-yl | base |
| 64. | 4-bromo-2-chlorophenyl | 2 | 2 | —OCH₂CH₂— | H | H | thiazol-2-yl | base |
| 65. | 2-methylquinolin-6-yl | 2 | 2 | —OCH₂CH₂— | H | H | thiazol-2-yl | CF₃CO₂H |
| 66. | 4'-cyanobiphenyl-3-yl | 2 | 2 | —OCH₂CH₂— | H | H | thiazol-2-yl | base |
| 67. | 6-cyanonaphthalen-2-yl | 2 | 2 | —OCH₂CH₂— | H | H | thiazol-2-yl | base |
| 68. | 4-(thiazol-2-yl)phenyl | 2 | 2 | —OCH₂CH₂— | H | H | thiazol-2-yl | base |

TABLE 1-continued

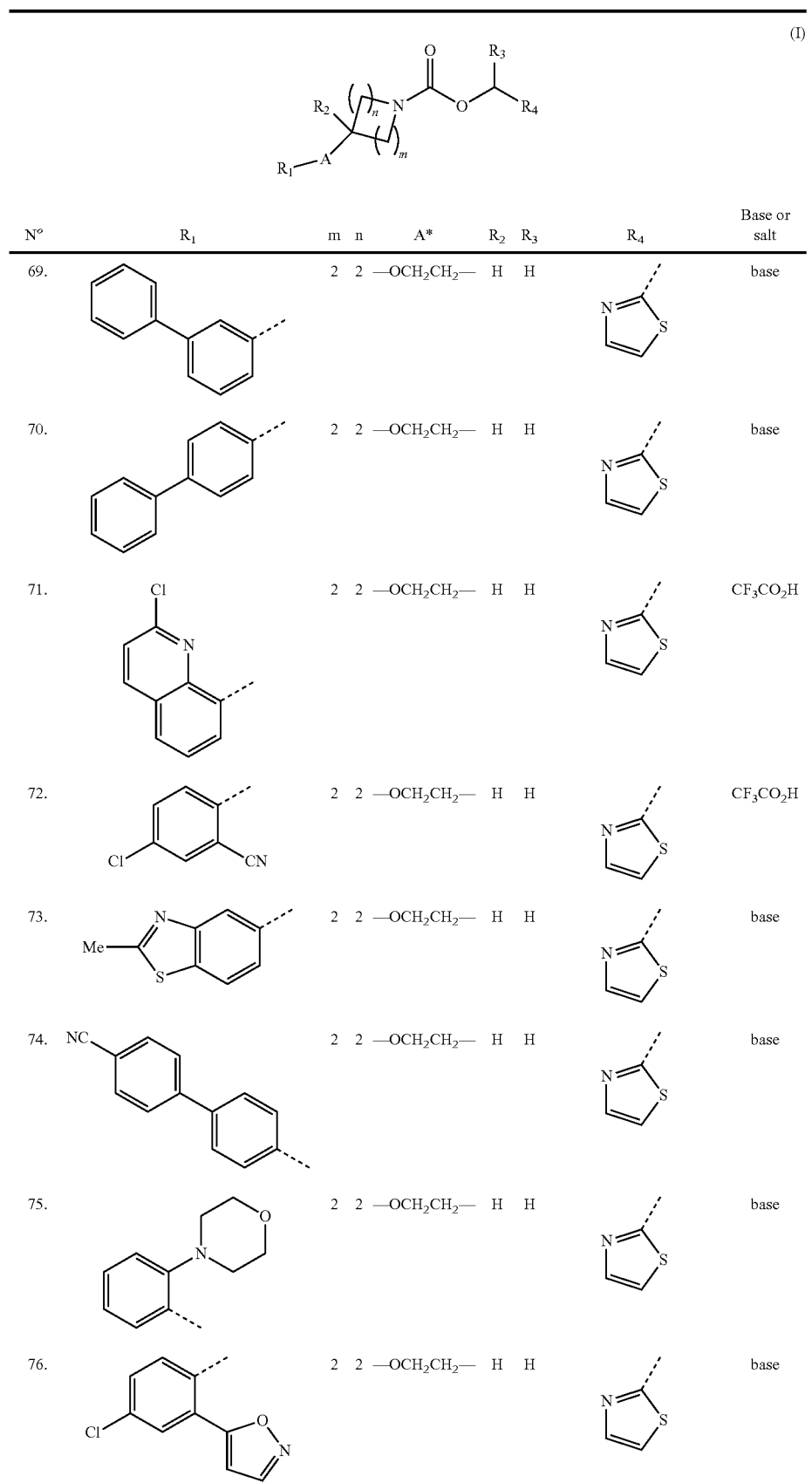

| N° | R₁ | m | n | A* | R₂ | R₃ | R₄ | Base or salt |
|---|---|---|---|---|---|---|---|---|
| 69. | 3-biphenyl | 2 | 2 | —OCH₂CH₂— | H | H | thiazol-2-yl | base |
| 70. | 4-biphenyl | 2 | 2 | —OCH₂CH₂— | H | H | thiazol-2-yl | base |
| 71. | 2-chloroquinolin-8-yl | 2 | 2 | —OCH₂CH₂— | H | H | thiazol-2-yl | CF₃CO₂H |
| 72. | 4-chloro-2-cyanophenyl | 2 | 2 | —OCH₂CH₂— | H | H | thiazol-2-yl | CF₃CO₂H |
| 73. | 2-methylbenzothiazol-5-yl | 2 | 2 | —OCH₂CH₂— | H | H | thiazol-2-yl | base |
| 74. | 4′-cyano-biphenyl-4-yl | 2 | 2 | —OCH₂CH₂— | H | H | thiazol-2-yl | base |
| 75. | 2-morpholinophenyl | 2 | 2 | —OCH₂CH₂— | H | H | thiazol-2-yl | base |
| 76. | 4-chloro-2-(isoxazol-5-yl)phenyl | 2 | 2 | —OCH₂CH₂— | H | H | thiazol-2-yl | base |

TABLE 1-continued (I)

| N° | R₁ | m | n | A* | R₂ | R₃ | R₄ | Base or salt |
|---|---|---|---|---|---|---|---|---|
| 77. | 2,4-dimethylphenyl | 2 | 2 | —OCH₂CH₂— | H | H | thiazol-4-yl | base |
| 78. | 2,3-dichlorophenyl | 2 | 2 | —OCH₂CH₂— | H | H | thiazol-4-yl | base |
| 79. | naphth-1-yl | 2 | 2 | —OCH₂CH₂— | H | H | thiazol-4-yl | base |
| 80. | 3-(dimethylamino)phenyl | 2 | 2 | —OCH₂CH₂— | H | H | thiazol-4-yl | CF₃CO₂H |
| 81. | 3-(trifluoromethyl)phenyl | 2 | 2 | —OCH₂CH₂— | H | H | thiazol-4-yl | base |
| 82. | 4-benzylphenyl | 2 | 2 | —OCH₂CH₂— | H | H | thiazol-4-yl | base |
| 83. | 2-ethoxyphenyl | 2 | 2 | —OCH₂CH₂— | H | H | thiazol-4-yl | base |
| 84. | 4-(2-phenylpropan-2-yl)phenyl | 2 | 2 | —OCH₂CH₂— | H | H | thiazol-4-yl | base |
| 85. | 4-phenoxyphenyl | 2 | 2 | —OCH₂CH₂— | H | H | thiazol-4-yl | base |

TABLE 1-continued (I)

| N° | R₁ | m | n | A* | R₂ | R₃ | R₄ | Base or salt |
|----|-----|---|---|------|----|----|-----|--------------|
| 86. | 4-F, 2-Br phenyl | 2 | 2 | —OCH₂CH₂— | H | H | thiazol-4-yl | base |
| 87. | 2-benzylphenyl | 2 | 2 | —OCH₂CH₂— | H | H | thiazol-4-yl | base |
| 88. | 3-phenoxyphenyl | 2 | 2 | —OCH₂CH₂— | H | H | thiazol-4-yl | base |
| 89. | 4-(C₆H₁₃O)phenyl | 2 | 2 | —OCH₂CH₂— | H | H | thiazol-4-yl | base |
| 90. | 3-(C₄H₉O)phenyl | 2 | 2 | —OCH₂CH₂— | H | H | thiazol-4-yl | base |
| 91. | 4-chloro-2-methyl-5-(isopropyl)phenyl | 2 | 2 | —OCH₂CH₂— | H | H | thiazol-4-yl | base |
| 92. | 3-(pentafluoroethyl)phenyl | 2 | 2 | —OCH₂CH₂— | H | H | thiazol-4-yl | base |
| 93. | 5-(1-acetamido)naphthyl | 2 | 2 | —OCH₂CH₂— | H | H | thiazol-4-yl | base |

TABLE 1-continued
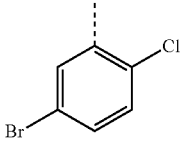
(I)
| N° | R$_1$ | m | n | A* | R$_2$ | R$_3$ | R$_4$ | Base or salt |
|----|-------|---|---|-----|-------|-------|-------|--------------|
| 94. | 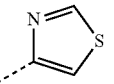 | 2 | 2 | —OCH$_2$CH$_2$— | H | H | 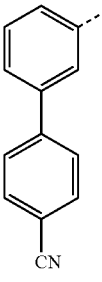 | base |
| 95. | 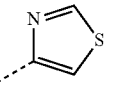 | 2 | 2 | —OCH$_2$CH$_2$— | H | H | 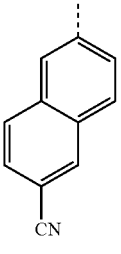 | base |
| 96. | 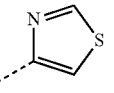 | 2 | 2 | —OCH$_2$CH$_2$— | H | H |  | base |
| 97. | 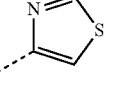 | 2 | 2 | —OCH$_2$CH$_2$— | H | H | 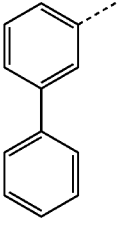 | base |
| 98. | 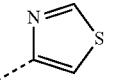 | 2 | 2 | —OCH$_2$CH$_2$— | H | H | | base |

TABLE 1-continued (I)

| N° | R₁ | m | n | A* | R₂ | R₃ | R₄ | Base or salt |
|---|---|---|---|---|---|---|---|---|
| 99. | 4-biphenyl | 2 | 2 | —OCH₂CH₂— | H | H | thiazol-4-yl | base |
| 100. | 5-chloro-2-cyanophenyl | 2 | 2 | —OCH₂CH₂— | H | H | thiazol-4-yl | base |
| 101. | 2-methylbenzothiazol-6-yl | 2 | 2 | —OCH₂CH₂— | H | H | thiazol-4-yl | base |
| 102. | 4'-cyano-4-biphenyl | 2 | 2 | —OCH₂CH₂— | H | H | thiazol-4-yl | base |
| 103. | 2-(morpholin-4-yl)phenyl | 2 | 2 | —OCH₂CH₂— | H | H | thiazol-4-yl | CF₃CO₂H |
| 104. | 3-chloro-2-(isoxazol-5-yl)phenyl | 2 | 2 | —OCH₂CH₂— | H | H | thiazol-4-yl | base |

TABLE 1-continued (I)

| N° | R₁ | m | n | A* | R₂ | R₃ | R₄ | Base or salt |
|---|---|---|---|---|---|---|---|---|
| 105. | 4-((CH₃)₂NCH₂)-phenyl | 2 | 2 | —OCH₂CH₂— | H | H | thiazol-2-yl | CF₃CO₂H |
| 106. | naphthalen-2-yl | 2 | 2 | —OCH₂CH₂— | H | H | thiazol-2-yl | base |
| 107. | naphthalen-1-yl | 2 | 2 | —OCH₂CH₂— | H | H | thiazol-2-yl | base |
| 108. | 6-methoxy-naphthalen-2-yl | 2 | 2 | —OCH₂CH₂— | H | H | thiazol-2-yl | base |
| 109. | 2-cyclopentyl-phenyl | 2 | 2 | —OCH₂CH₂— | H | H | thiazol-4-yl | base |
| 110. | 2-benzyloxy-phenyl | 2 | 2 | —OCH₂CH₂— | H | H | thiazol-4-yl | base |

TABLE 1-continued (I)

| N° | R₁ | m | n | A* | R₂ | R₃ | R₄ | Base or salt |
|---|---|---|---|---|---|---|---|---|
| 111. | isoquinolin-7-yl | 2 | 2 | —OCH₂CH₂— | H | H | thiazol-4-yl | CF₃CO₂H |
| 112. | quinolin-5-yl | 2 | 2 | —OCH₂CH₂— | H | H | thiazol-4-yl | CF₃CO₂H |
| 113. | 2-methylquinolin-6-yl | 2 | 2 | —OCH₂CH₂— | H | H | thiazol-4-yl | CF₃CO₂H |
| 114. | 2-cyanoquinolin-8-yl | 2 | 2 | —OCH₂CH₂— | H | H | thiazol-4-yl | CF₃CO₂H |
| 115. | 2,4-dichlorophenyl | 2 | 2 | —OCH₂CH₂— | H | H | thiazol-4-yl | base |
| 116. | 4-cyclopentylphenyl | 2 | 2 | —OCH₂CH₂— | H | H | thiazol-4-yl | base |
| 117. | 2-(benzoxazol-2-yl)phenyl | 2 | 2 | —OCH₂CH₂— | H | H | thiazol-4-yl | base |

TABLE 1-continued
(I)
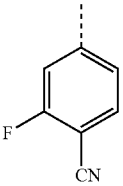
| N° | R₁ | m | n | A* | R₂ | R₃ | R₄ | Base or salt |
|---|---|---|---|---|---|---|---|---|
| 118. | 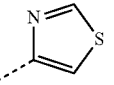 | 2 | 2 | —OCH₂CH₂— | H | H | 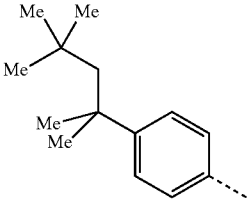 | base |
| 119. | 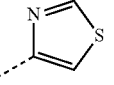 | 2 | 2 | —OCH₂CH₂— | H | H | 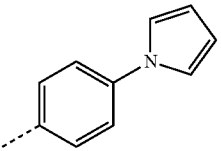 | base |
| 120. | 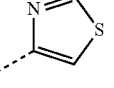 | 2 | 2 | —OCH₂CH₂— | H | H | 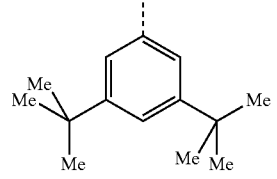 | CF₃CO₂H |
| 121. | 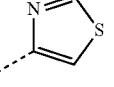 | 2 | 2 | —OCH₂CH₂— | H | H | 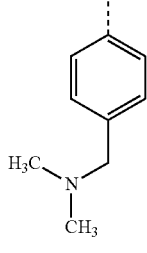 | base |
| 122. | 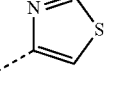 | 2 | 2 | —OCH₂CH₂— | H | H | 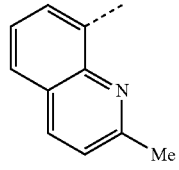 | CF₃CO₂H |
| 123. | 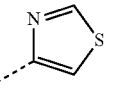 | 2 | 2 | —OCH₂CH₂— | H | H | 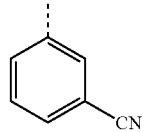 | CF₃CO₂H |
| 124. | 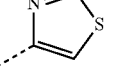 | 2 | 2 | —OCH₂CH₂— | H | H | | base |

TABLE 1-continued
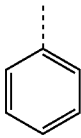
(I)
| N° | R₁ | m | n | A* | R₂ | R₃ | R₄ | Base or salt |
|---|---|---|---|---|---|---|---|---|
| 125. | 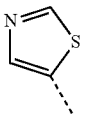 | 2 | 2 | —OCH₂CH₂— | H | H | 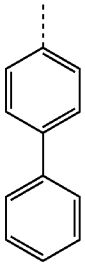 | base |
| 126. | 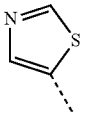 | 2 | 2 | —OCH₂CH₂— | H | H | 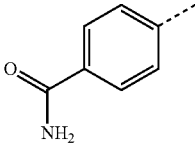 | base |
| 127. | 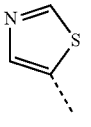 | 2 | 2 | —OCH₂CH₂— | H | H | 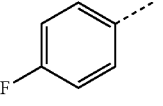 | base |
| 128. | 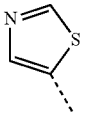 | 2 | 2 | —OCH₂CH₂— | H | H | 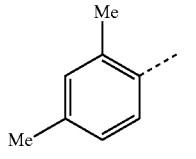 | base |
| 129. | 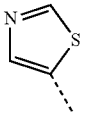 | 2 | 2 | —OCH₂CH₂— | H | H | 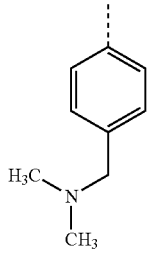 | base |
| 130. | 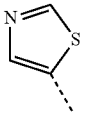 | 2 | 2 | —OCH₂CH₂— | H | H | 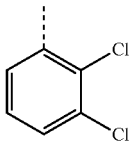 | CF₃CO₂H |
| 131. | 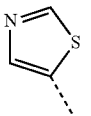 | 2 | 2 | —OCH₂CH₂— | H | H | 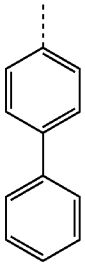 | base |

TABLE 1-continued
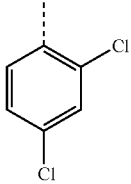
(I)
| N° | R₁ | m | n | A* | R₂ | R₃ | R₄ | Base or salt |
|---|---|---|---|---|---|---|---|---|
| 132. | 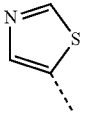 | 2 | 2 | —OCH₂CH₂— | H | H | 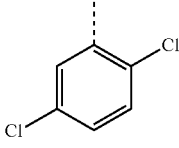 | base |
| 133. | 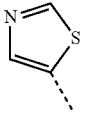 | 2 | 2 | —OCH₂CH₂— | H | H | 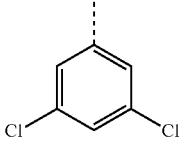 | base |
| 134. | 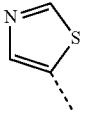 | 2 | 2 | —OCH₂CH₂— | H | H | 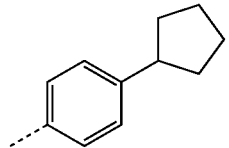 | base |
| 135. | 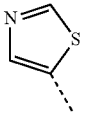 | 2 | 2 | —OCH₂CH₂— | H | H | 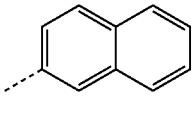 | base |
| 136. | 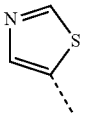 | 2 | 2 | —OCH₂CH₂— | H | H | 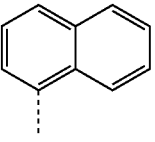 | base |
| 137. | 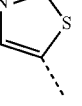 | 2 | 2 | —OCH₂CH₂— | H | H | 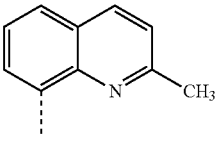 | base |
| 138. | 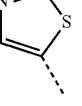 | 2 | 2 | —OCH₂CH₂— | H | H | 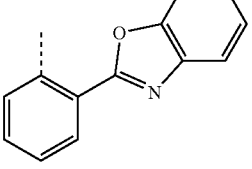 | base |
| 139. | 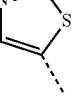 | 2 | 2 | —OCH₂CH₂— | H | H | | base |

TABLE 1-continued
(I)
| N° | R₁ | m | n | A* | R₂ | R₃ | R₄ | Base or salt |
|---|---|---|---|---|---|---|---|---|
| 140. | 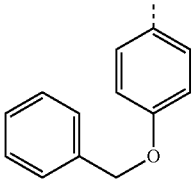 | 2 | 2 | —OCH₂CH₂— | H | H | 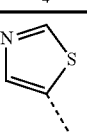 | base |
| 141. | 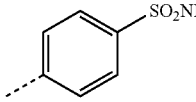 | 2 | 2 | —OCH₂CH₂— | H | H |  | base |
| 142. | 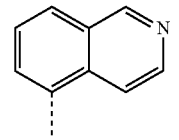 | 2 | 2 | —OCH₂CH₂— | H | H | 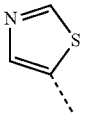 | base |
| 143. | 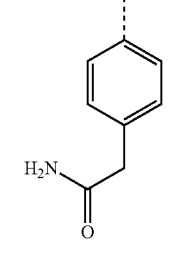 | 2 | 2 | —OCH₂CH₂— | H | H | 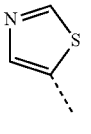 | base |
| 144. | 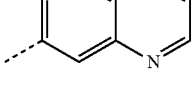 | 2 | 2 | —OCH₂CH₂— | H | H |  | base |
| 145. | 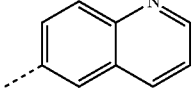 | 2 | 2 | —OCH₂CH₂— | H | H |  | base |
| 146. | 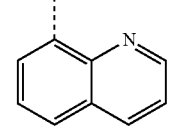 | 2 | 2 | —OCH₂CH₂— | H | H | 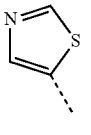 | base |
| 147. | 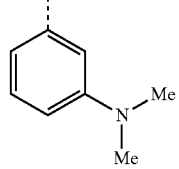 | 2 | 2 | —OCH₂CH₂— | H | H |  | CF₃CO₂H |

TABLE 1-continued (I)

| N° | R₁ | m | n | A* | R₂ | R₃ | R₄ | Base or salt |
|---|---|---|---|---|---|---|---|---|
| 148. | 4-CN-3-F-phenyl | 2 | 2 | —OCH₂CH₂— | H | H | thiazol-5-yl | base |
| 149. | biphenyl-2-yl | 2 | 2 | —OCH₂CH₂— | H | H | thiazol-5-yl | base |
| 150. | biphenyl-3-yl | 2 | 2 | —OCH₂CH₂— | H | H | thiazol-5-yl | base |
| 151. | 3-CF₃-phenyl | 2 | 2 | —OCH₂CH₂— | H | H | thiazol-5-yl | base |
| 152. | 4-benzylphenyl | 2 | 2 | —OCH₂CH₂— | H | H | thiazol-5-yl | base |
| 153. | 2-OC₂H₅-phenyl | 2 | 2 | —OCH₂CH₂— | H | H | thiazol-5-yl | base |
| 154. | 2-cyclopentylphenyl | 2 | 2 | —OCH₂CH₂— | H | H | thiazol-5-yl | base |
| 155. | 4-(2-phenylpropan-2-yl)phenyl | 2 | 2 | —OCH₂CH₂— | H | H | thiazol-5-yl | base |

TABLE 1-continued (I)

| N° | R₁ | m | n | A* | R₂ | R₃ | R₄ | Base or salt |
|---|---|---|---|---|---|---|---|---|
| 156. | (4-phenoxyphenyl) | 2 | 2 | —OCH₂CH₂— | H | H | thiazol-5-yl | base |
| 157. | (2-bromo-4-fluorophenyl) | 2 | 2 | —OCH₂CH₂— | H | H | thiazol-5-yl | base |
| 158. | (4-(1H-pyrrol-1-yl)phenyl) | 2 | 2 | —OCH₂CH₂— | H | H | thiazol-5-yl | base |
| 159. | (3-cyanophenyl) | 2 | 2 | —OCH₂CH₂— | H | H | thiazol-5-yl | base |
| 160. | (3,5-di-tert-butylphenyl) | 2 | 2 | —OCH₂CH₂— | H | H | thiazol-5-yl | base |
| 161. | (2-benzylphenyl) | 2 | 2 | —OCH₂CH₂— | H | H | thiazol-5-yl | base |
| 162. | (2-(benzyloxy)phenyl) | 2 | 2 | —OCH₂CH₂— | H | H | thiazol-5-yl | base |

TABLE 1-continued (I)

| N° | R₁ | m | n | A* | R₂ | R₃ | R₄ | Base or salt |
|---|---|---|---|---|---|---|---|---|
| 163. | 2-cyanoquinolin-8-yl | 2 | 2 | —OCH₂CH₂— | H | H | thiazol-5-yl | base |
| 164. | 3-(methoxycarbonyl)naphthalen-2-yl | 2 | 2 | —OCH₂CH₂— | H | H | thiazol-5-yl | base |
| 165. | 3-phenoxyphenyl | 2 | 2 | —OCH₂CH₂— | H | H | thiazol-5-yl | base |
| 166. | 2-cyano-4-chlorophenyl | 2 | 2 | —OCH₂CH₂— | H | H | thiazol-5-yl | base |
| 167. | isoquinolin-7-yl | 2 | 2 | —OCH₂CH₂— | H | H | thiazol-5-yl | base |
| 168. | 4-(hexyloxy)phenyl | 2 | 2 | —OCH₂CH₂— | H | H | thiazol-5-yl | base |
| 169. | 3-(butyloxy)phenyl | 2 | 2 | —OCH₂CH₂— | H | H | thiazol-5-yl | base |

TABLE 1-continued
| N° | R₁ | m | n | A* | R₂ | R₃ | R₄ | Base or salt |
|---|---|---|---|---|---|---|---|---|
| 170. | 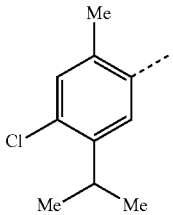 | 2 | 2 | —OCH₂CH₂— | H | H | 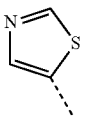 | base |
| 171. | 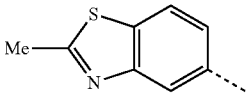 | 2 | 2 | —OCH₂CH₂— | H | H |  | base |
| 172. | 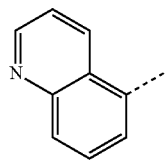 | 2 | 2 | —OCH₂CH₂— | H | H | 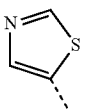 | base |
| 173. | 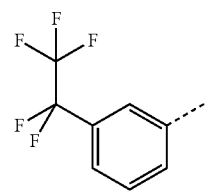 | 2 | 2 | —OCH₂CH₂— | H | H | 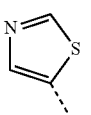 | base |
| 174. | 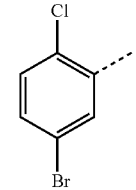 | 2 | 2 | —OCH₂CH₂— | H | H | 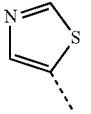 | base |
| 175. | 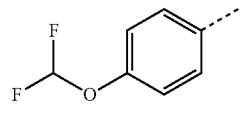 | 2 | 2 | —OCH₂CH₂— | H | H | 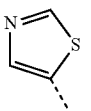 | base |
| 176. | 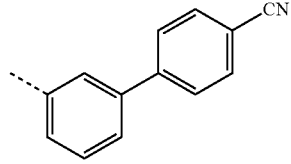 | 2 | 2 | —OCH₂CH₂— | H | H | 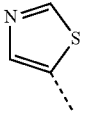 | base |

TABLE 1-continued
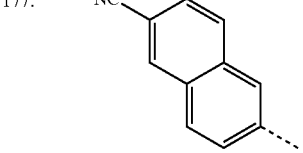
(I)
| N° | R₁ | m | n | A* | R₂ | R₃ | R₄ | Base or salt |
|---|---|---|---|---|---|---|---|---|
| 177. | 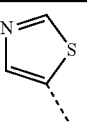 | 2 | 2 | —OCH₂CH₂— | H | H | 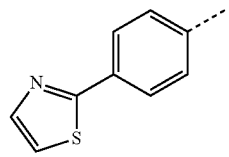 | base |
| 178. | 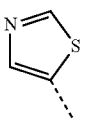 | 2 | 2 | —OCH₂CH₂— | H | H | 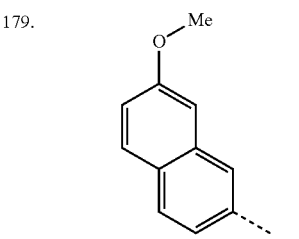 | base |
| 179. | 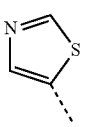 | 2 | 2 | —OCH₂CH₂— | H | H | 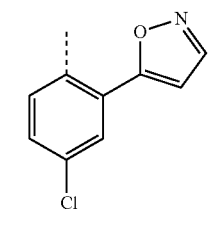 | base |
| 180. | 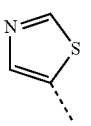 | 2 | 2 | —OCH₂CH₂— | H | H | 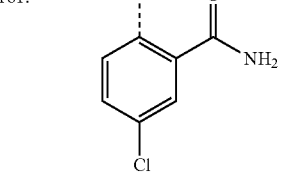 | base |
| 181. |  | 2 | 2 | —OCH₂CH₂— | H | H | 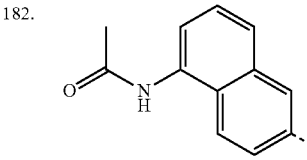 | base |
| 182. | 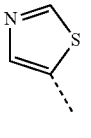 | 2 | 2 | —OCH₂CH₂— | H | H | 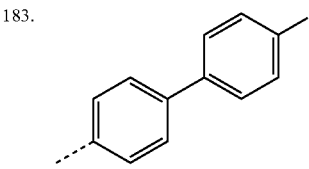 | base |
| 183. | 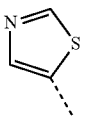 | 2 | 2 | —OCH₂CH₂— | H | H | | base |

TABLE 1-continued

| N° | R₁ | m | n | A* | R₂ | R₃ | R₄ | Base or salt |
|---|---|---|---|---|---|---|---|---|
| 184. | 4-(SO₂Me)phenyl | 2 | 2 | —OCH₂CH₂— | H | H | thiazol-5-yl | base |
| 185. | 3-acetamido-4-propylphenyl | 2 | 2 | —OCH₂CH₂— | H | H | thiazol-5-yl | base |
| 186. | indol-6-yl | 2 | 2 | —OCH₂CH₂— | H | H | thiazol-5-yl | base |
| 187. | 5-fluoro-2-(pyrazol-3-yl)phenyl | 2 | 2 | —OCH₂CH₂— | H | H | thiazol-5-yl | base |
| 188. | 4-cyano-2-fluorophenyl | 2 | 2 | —OCH₂CH₂— | H | H | thiazol-5-yl | base |
| 189. | 2-(propan-2-yl)-4-methyl-(methyl)phenyl | 2 | 2 | —OCH₂CH₂— | H | H | thiazol-5-yl | base |
| 190. | 2-(morpholin-4-yl)phenyl | 2 | 2 | —OCH₂CH₂— | H | H | thiazol-5-yl | CF₃CO₂H |
| 191. | 2-methylquinolin-6-yl | 2 | 2 | —OCH₂CH₂— | H | H | thiazol-5-yl | base |

TABLE 1-continued
(I)
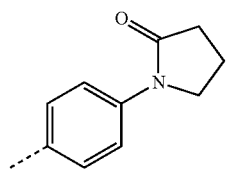
| N° | R₁ | m | n | A* | R₂ | R₃ | R₄ | Base or salt |
|---|---|---|---|---|---|---|---|---|
| 192. | 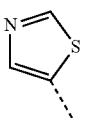 | 2 | 2 | —OCH₂CH₂— | H | H | 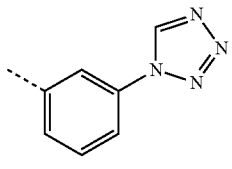 | base |
| 193. | 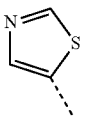 | 2 | 2 | —OCH₂CH₂— | H | H | 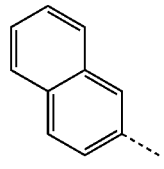 | base |
| 194. | 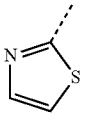 | 1 | 2 | —OCH₂— | H | H | 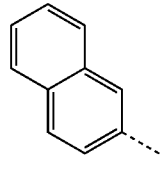<br>(R)<br>Enantiomer I | base |
| 195. | 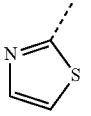 | 1 | 2 | —OCH₂— | H | H | 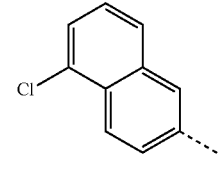<br>(S)<br>Enantiomer II | base |
| 196. | 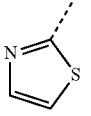 | 1 | 2 | —OCH₂— | H | H | 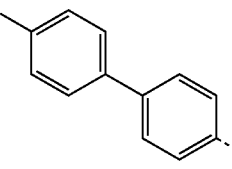<br>(+/−) | base |
| 197. | 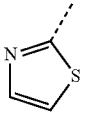 | 1 | 2 | —OCH₂— | H | H | 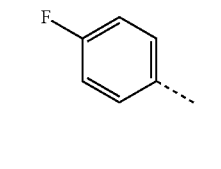<br>(+/−) | base |
| 198. | 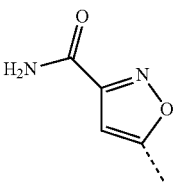 | 2 | 2 | —OCH₂CH₂— | H | H |  | base |

TABLE 1-continued (I)

| N° | R₁ | m | n | A* | R₂ | R₃ | R₄ | Base or salt |
|---|---|---|---|---|---|---|---|---|
| 199. | 4-(OCF₃)-phenyl | 2 | 2 | —OCH₂CH₂— | H | H | 5-methyl-isoxazole-3-carboxamide | base |
| 200. | naphth-2-yl | 2 | 1 | —OCH₂— | H | H | 5-methyl-isoxazole-3-carboxamide (R) (−) Enantiomer I | base |
| 201. | 6-methoxy-naphth-2-yl | 2 | 1 | —OCH₂— | H | H | 5-methyl-isoxazole-3-carboxamide (+/−) | base |
| 202. | naphth-2-yl | 2 | 1 | —OCH₂— | H | H | 5-methyl-isoxazole-3-carboxamide (S) (+) Enantiomer II | base |

The results of the $^1$H NMR analyses and the melting points (M.p.) for the compounds in Table 1 are given in the following Table 2.

TABLE 2

| N° | $^1$H NMR 400 MHz d$_6$-DMSO/CDCl$_3$ | M.p. (° C.) |
|---|---|---|
| 1 | 8.25 (m, 2H); 7.80 (d, 1H); 7.60 (m, 2H); 7.50 (d, 1H); 7.40 (d, 1H); 6.70 (d, 1H); 5.45 (s, 2H); 4.20 (m, 4H); 2.90 (m, 2H); 1.80 (m; 5H); 1.30 (m, 2H) | oil |
| 2 | 7.80 (d, 1H); 7.70 (d, 1H); 7.10 (m, 2H); 6.90 (m, 2H); 5.35 (s, 2H); 4.00 (m, 2H); 2.85 (m, 2H); 1.70 (m, 5H); 1.10 (m, 2H) | oil |
| 3 | 8.80 (s, 1H); 7.40 (s, 1H); 7.00 (m, 2H); 6.85 (m, 2H); 5.30 (s, 2H); 4.20 (m, 2H); 4.00 (m, 2H); 2.80 (m, 2H); 1.70 (m, 5H); 1.25 (m, 2H) | 76-78 |
| 4 | 9.10 (s, 1H), 7.65 (s, 1H); 7.60 (d, 2H); 7.10 (d, 2H); 5.20 (s, 2H); 4.10 (m, 2H); 4.00 (m, 2H); 2.80 (m, 2H); 1.70 (m, 5H); 1.15 (m, 2H) | oil |

TABLE 2-continued

| N° | ¹H NMR 400 MHz d₆-DMSO/CDCl₃ | M.p. (° C.) |
|---|---|---|
| 5 | 9.10 (s, 1H); 7.65 (s, 1H); 7.30 (d, 2H); 6.90 (d, 2H); 5.10 (s, 2H); 3.90 (m, 4H); 2.80 (m, 2H); 1.70 (m, 4H); 1.10 (m, 2H) | 53-55 |
| 6 | 8.80 (s, 1H); 7.90 (s, 1H); 7.00 (m, 2H); 6.80 (m, 2H); 5.30 (s, 2H); 4.20 (m, 2H); 4.00 (m, 2H); 2.80 (m, 2H); 1.75 (m, 6H); 1.20 (m, 2H) | 96-98 |
| 7 | 9.10 (s, 1H); 7.90 (s, 1H); 7.30 (d, 2H); 6.95 (d, 2H); 5.30 (s, 2H); 3.90 (m, 4H); 2.80 (m, 2H); 1.60 (m, 6H); 1.10 (m, 2H) | 93-97 |
| 8 | 9.10 (s, 1H); 7.95 (s, 1H); 7.60 (d, 2H); 7.10 (d, 2H); 5.30 (s, 2H); 4.10 (m, 2H); 3.95 (m, 2H); 2.80 (m, 2H); 1.65 (m, 6H); 1.10 (m, 2H) | 47-49 |
| 9 | 9.10 (s, 1H); 7.75 (s, 1H); 7.70 (m, 2H); 7.20 (m, 2H); 6.95 (m, 2H); 5.15 (s, 2H); 4.10 (m, 2H); 4.00 (m, 2H); 3.80 (s, 3H); 2.80 (m, 2H); 1.70 (m, 5H); 1.15 (m, 2H) | 95-97 |
| 10 | 8.80 (s, 1H); 7.60 (d, 2H); 7.40 (s, 1H); 6.95 (d, 2H); 5.30 (s, 2H); 4.20 (m, 2H); 4.05 (m, 2H); 2.80 (m, 2H); 1.75 (m, 5H); 1.20 (m, 2H) | 108-110 |
| 11 | 8.80 (s, 1H); 7.65 (m, 2H); 7.40 (s, 1H); 7.10 (m, 4H), 5.30 (s, 2H); 4.05 (m, 2H); 3.90 (s, 3H); 3.80-3.35 (m, 4H); 2.80 (m, 1H); 2.20 (m, 1H); 1.90 (m, 1H) | 128-130 |
| 12 | 8.80 (s, 1H); 7.70 (m, 2H); 7.40 (s, 1H); 7.05 (m, 4H), 5.35 (s, 2H); 4.10 (m, 2H); 3.90 (s, 3H); 3.80 (m, 1H); 3.65 (m, 1H); 3.55 (m, 1H); 3.40 (m, 1H); 2.80 (m, 1H); 2.20 (m, 1H); 1.90 (m, 1H) | 112-114 |
| 13 | 8.80 (s, 1H); 7.40 (s, 1H); 7.35 (d, 1H); 7.00 (s, 1H); 6.75 (d, 1H); 5.30 (s, 2H); 3.90 (m, 2H); 3.70 (m, 1H); 3.60 (m, 1H); 3.50 (m, 1H); 3.30 (m, 1H); 2.70 (m, 1H); 2.10 (m, 1H); 1.80 (m, 1H) | 78-80 |
| 14 | 8.80 (s, 1H); 7.65 (m, 2H); 7.40 (s, 1H); 7.10 (m, 4H); 5.30 (s, 2H); 4.20 (m, 2H); 4.10 (m, 2H); 3.90 (s, 3H); 2.80 (m, 2H); 1.80 (m, 5H); 1.25 (m, 2H) | 100-102 |
| 15 | 8.80 (s, 1H); 7.80 (m, 3H); 7.45 (m, 1H); 7.40 (m, 2H); 7.15 (m, 2H); 5.30 (s, 2H); 4.25 (m, 2H); 4.20 (m, 2H); 2.90 (m, 2H); 1.85 (m, 5H); 1.25 (m, 2H) | 88-90 |
| 16 | 9.10 (m, 1H); 8.50 (m, 2H); 7.95 (m, 1H); 7.85 (m, 1H); 7.75 (d, 1H); 7.70 (m, 1H); 7.00 (d, 1H); 5.60 (s, 2H); 4.40 (m, 2H); 4.10 (m, 1H); 4.00 (m, 1H); 3.85 (m, 1H); 3.70 (m, 1H); 3.20 (m, 1H); 2.50 (m, 1H); 2.30 (m, 1H) | 84-86 |
| 17 | 9.10 (s, 1H); 7.85 (m, 3H); 7.70 (m, 1H); 7.50 (m, 1H); 7.35 (m, 2H); 7.20 (m, 1H); 5.20 (s, 2H); 4.10 (m, 2H); 3.60 (m, 1H); 3.50 (m, 1H); 3.40 (m, 1H); 3.30 (m, 1H); 2.70 (m, 1H); 2.10 (m, 1H); 1.80 (m, 1H) | 90-92 |
| 18 | 8.80 (s, 1H); 7.50 (m, 4H); 7.40 (s, 1H); 7.10 (m, 2H); 6.95 (d, 2H); 5.30 (s, 2H); 4.20 (m, 2H); 4.10 (m, 2H); 2.85 (m, 2H); 1.80 (m, 5H); 1.25 (m, 2H) | 62-64 |
| 19 | 9.10 (s, 1H); 9.05 (m, 1H); 8.80 (d, 1H); 8.20 (d, 1H); 7.90 (m, 1H); 7.70 (m, 3H); 5.20 (s, 2H); 4.25 (m, 2H); 4.00 (m, 2H); 2.85 (m, 2H); 1.80 (m, 5H); 1.15 (m, 2H) | 140-150 |
| 20 | 9.70 (s, 1H); 9.10 (s, 1H); 8.60 (d, 1H); 8.45 (d, 1H); 8.30 (d, 1H); 7.80 (s, 1H); 7.70 (m, 2H); 5.20 (s, 2H); 4.35 (m, 2H); 4.00 (m, 2H); 2.85 (m, 2H); 1.80 (m, 5H); 1.20 (m, 2H) | 150-160 |
| 21 | 9.10 (s, 1H); 8.20 (s, 1H); 8.10 (d, 1H); 7.85 (d, 1H); 7.70 (m, 2H); 7.40 (m, 1H); 7.30 (m, 2H); 7.00 (m, 1H); 5.20 (s, 2H); 4.10 (m, 2H); 3.60 (m, 1H); 3.50 (m, 1H); 3.40 (m, 1H); 3.20 (m, 1H); 2.70 (m, 1H); 2.10 (m, 1H); 1.80 (m, 1H) | oil |
| 22 | 9.10 (s, 1H); 7.70 (m, 3H); 7.60 (d, 2H); 7.30 (m, 2H); 7.05 (m, 2H); 5.20 (s, 2H); 4.05 (m, 2H); 3.60 (m, 1H); 3.50 (m, 1H); 3.35 (m, 1H); 3.20 (m, 1H); 2.70 (m, 1H); 2.10 (m, 1H); 1.80 (m, 1H) | 115-117 |
| 23 | 9.10 (s, 1H); 8.10 (d, 1H); 7.80 (d, 1H); 7.70 (m, 1H); 7.50 (m, 3H); 7.30 (d, 1H); 5.20 (s, 2H); 4.15 (m, 2H); 3.60 (m, 1H); 3.50 (m, 1H); 3.40 (m, 1H); 3.25 (m, 1H); 2.80 (m, 1H); 2.10 (m, 1H); 1.80 (m, 1H) | 89-91 |
| 24 | 9.10 (s, 1H); 7.70 (s, 1H); 7.40 (m, 1H); 7.05 (m, 1H); 6.95 (m, 2H); 5.20 (s, 2H); 4.05 (m, 2H); 3.60 (m, 1H); 3.50 (m, 1H); 3.35 (m, 1H); 3.20 (m, 1H); 2.70 (m, 1H); 2.10 (m, 1H); 1.80 (m, 1H) | 54-56 |
| 25 | 9.10 (s, 1H); 7.70 (s, 1H); 7.30-7.10 (m, 7H); 6.90 (m, 2H); 5.20 (s, 2H); 4.00 (m, 2H); 3.60 (m, 1H); 3.50 (m, 1H); 3.35 (m, 1H); 3.20 (m, 1H); 2.70 (m, 1H); 2.05 (m, 1H); 1.75 (m, 1H); 1.60 (s, 6H) | 76-78 |
| 26 | 9.10 (s, 1H); 8.70 (s, 1H); 8.00 (d, 1H); 7.90 (m, 1H); 7.80 (m, 1H); 7.70 (m, 1H); 7.60 (m, 2H); 5.20 (s, 2H); 4.20 (m, 2H); 3.65 (m, 1H); 3.55 (m, 1H); 3.40 (m, 1H); 3.30 (m, 1H); 2.80 (m, 1H); 2.10 (m, 1H); 1.85 (m, 1H) | 83-85 |
| 27 | 9.20 (s, 1H); 9.10 (m, 1H); 8.40 (d, 1H); 8.05 (d, 1H); 7.70 (m, 2H); 7.40 (m, 1H); 7.30 (d, 1H); 5.20 (s, 2H); 4.20 (m, 2H); 3.60 (m, 1H); 3.50 (m, 1H); 3.40 (m, 1H); 3.30 (m, 1H); 2.75 (m, 1H); 2.10 (m, 1H); 1.80 (m, 1H) | 122-124 |
| 28 | 9.10 (s, 1H); 8.80 (s, 1H); 8.30 (d, 1H); 7.90 (d, 1H); 7.70 (m, 1H); 7.40 (m, 2H); 7.30 (d, 1H); 5.20 (s, 2H); 4.20 (m, 2H); 3.60 (m, 1H); 3.50 (m, 1H); 3.40 (m, 1H); 3.30 (m, 1H); 2.80 (m, 1H); 2.10 (m, 1H); 1.80 (m, 1H) | 94-96 |
| 29 | 9.20 (s, 1H); 9.10 (s, 1H); 8.40 (d, 1H); 7.90 (d, 1H); 7.80 (d, 1H); 7.70 (m, 1H); 7.55 (s, 1H); 7.45 (d, 1H); 5.20 (s, 2H); 4.20 (m, 2H); 3.60 (m, 1H); 3.50 (m, 1H); 3.40 (m, 1H); 3.30 (m, 1H); 2.80 (m, 1H); 2.10 (m, 1H); 1.80 (m, 1H) | 121-123 |
| 30 | 9.10 (s, 1H); 7.65 (m, 2H); 7.40 (s, 1H); 7.30 (d, 1H); 5.20 (s, 2H); 4.10 (m, 2H); 3.60 (m, 1H); 3.50 (m, 1H); 3.40 (m, 1H); 3.20 (m, 1H); 2.70 (m, 1H); 2.10 (m, 1H); 1.80 (m, 1H) | 60-62 |
| 31 | 9.10 (s, 1H); 8.00 (d, 1H); 7.70 (m, 2H); 7.50 (m, 2H); 7.30 (d, 1H); 7.15 (m, 1H); 5.20 (s, 2H); 4.15 (m, 2H); 3.60 (m, 1H); 3.50 (m, 1H); 3.40 (m, 1H); 3.30 (m, 1H); 2.80 (m, 1H); 2.10 (m, 1H); 1.85 (m, 1H) | 76-78 |

TABLE 2-continued

| N° | $^1$H NMR 400 MHz d$_6$-DMSO/CDCl$_3$ | M.p. (° C.) |
|---|---|---|
| 194 | 7.90 (m, 4H); 7.75 (d, 1H); 7.50 (m, 1H); 7.35 (m, 2H); 7.20 (d, 1H); 5.35 (s, 2H); 4.15 (m, 2H); 3.65 (m, 1H); 3.55 (m, 1H); 3.45 (m, 1H); 3.30 (m, 1H); 2.80 (m, 1H); 2.15 (m, 1H); 1.85 (m, 1H) | 100-112 |
| 195 | 7.90 (m, 4H); 7.75 (d, 1H); 7.50 (m, 1H); 7.35 (m, 2H); 7.20 (d, 1H); 5.35 (s, 2H); 4.15 (m, 2H); 3.65 (m, 1H); 3.55 (m, 1H); 3.45 (m, 1H); 3.30 (m, 1H); 2.80 (m, 1H); 2.15 (m, 1H); 1.85 (m, 1H) | 112-114 |
| 196 | 8.10 (d, 1H); 7.85 (m, 2H); 7.75 (d, 1H); 7.50 (m, 3H); 7.40 (d, 1H); 5.35 (s, 2H); 4.20 (m, 2H); 3.65 (m, 1H); 3.55 (m, 1H); 3.45 (m, 1H); 3.30 (m, 1H); 2.80 (m, 1H); 2.15 (m, 1H); 1.85 (m, 1H) | 100-102 |
| 197 | 7.85 (m, 1H); 7.75 (m, 1H); 7.65 (m, 2H); 7.60 (d, 2H); 7.30 (m, 2H); 7.05 (d, 2H); 5.40 (s, 2H); 4.10 (m, 2H); 3.60 (m, 1H); 3.50 (m, 1H); 3.40 (m, 1H); 3.30 (m, 1H); 2.70 (m, 1H); 2.10 (m, 1H); 1.80 (m, 1H) | 81-83 |
| 198 | 8.15 (bs, 1H); 7.85 (bs, 1H); 7.15 (m, 2H); 7.00 (m, 2H); 6.80 (s, 1H); 5.25 (s, 2H); 4.00 (m, 4H); 2.90 (m, 2H); 1.70 (m, 5H); 1.10 (m, 2H) | 106-108 |
| 199 | 8.15 (bs, 1H); 7.85 (bs, 1H); 7.30 (d, 2H); 7.05 (d, 2H); 6.80 (s, 1H); 5.25 (s, 2H); 4.05 (m, 4H); 2.85 (m, 2H); 1.70 (m, 5H); 1.10 (m, 2H) | 112-115 |
| 200 | 8.15 (bs, 1H); 7.80 (m, 4H); 7.50 (m, 1H); 7.35 (m, 2H); 7.20 (m, 1H); 6.80 (s, 1H); 5.30 (s, 2H); 4.10 (m, 2H); 3.65 (m, 1H); 3.50 (m, 1H); 3.40 (m, 1H); 3.30 (m, 1H); 2.80 (m, 1H); 2.10 (m, 1H); 1.85 (m, 1H) | 138-140 |
| 201 | 8.15 (bs, 1H); 8.85 (bs, 1H); 8.75 (m, 2H); 7.30 (m, 2H); 7.20 (m, 2H); 6.80 (s, 1H); 5.30 (s, 2H); 4.10 (m, 2H); 3.90 (s, 3H); 3.60 (m, 1H); 3.50 (m, 1H); 3.40 (m, 1H); 3.30 (m, 1H); 2.80 (m, 1H); 2.10 (m, 1H); 1.85 (m, 1H) | 193-195 |
| 202 | 8.15 (bs, 1H); 7.80 (m, 4H); 7.50 (m, 1H); 7.35 (m, 2H); 7.20 (m, 1H); 6.80 (s, 1H); 5.30 (s, 2H); 4.10 (m, 2H); 3.65 (m, 1H); 3.50 (m, 1H); 3.40 (m, 1H); 3.30 (m, 1H); 2.80 (m, 1H); 2.10 (m, 1H); 1.85 (m, 1H) | 139-141 |

The results for the masses M+H measured by LC-MS and the retention times for the compounds in Table 1 are given in the following Table 3.

LC-MS Conditions:

Method A:

HPLC/ZQ - Gradient 10 min
Mobile phases: Phase A: CH$_3$COONH$_4$ + 3% ACN
Phase B: ACN
Stationary phase/column: Kromasil C18 column
Dimensions: 50*2.1 mm; 3.5 μm
Flow rate: D = 0.8 ml/min
Temperature of the column: T = 40° C.
Injection volume: V = 5 μl
Gradient: T = 0 min: 100% of A, from T = 5.5 min to T = 7 min: 100% of B, from T = 7.1 min to T = 10 min: 100% of A.

Method B:

UPLC/TOF - Gradient 3 min
Mobile phases: Phase A: H$_2$O + 0.05% of TFA
Phase B: ACN + 0.035% of TFA
Stationary phase/column: Acquity BEH C18 column
Dimensions: 50*2.1 mm; 1.7 μm
Flow rate: D =1.0 ml/min
Temperature of the column: T = 40° C.
Injection volume: V = 2 μl
Gradient: T = 0 min: 98% of A and 2% of B, from T = 1.6 min to T = 2.1 min: 100% of B, from T = 2.5 min to T = 3 min: 98% of A and 2% of B.

Method C:

LC/TRAP - Gradient 20 min
Mobile phases: H$_2$O/CH$_3$COONH$_4$/ACN
Stationary phase/column: Kromasil C18 column Method D:

LC/ZQ - Gradient 20 min
Mobile phases: TFA/ACN
Stationary phase/column: Kromasil C18 column Method E:

LC/TOF - Gradient 20 min
Mobile phases: H$_2$O/CH$_3$COONH$_4$/ACN
Stationary phase/column: Kromasil C18 column Method F:

Stationary phase/column: Jsphere
Dimensions: 33*2 mm; 4 μm
Gradient: H$_2$O + 0.05% TFA:ACN + 0.05% TFA;
2:98 (1 min) to 95:5 (5.0 min) to 95:5 (6.25 min).

Method G:

Stationary phase/column: Waters XBridge C18
Dimensions: 4.6*50 mm; 2.5 μm
Gradient: H$_2$O + 0.05% TFA:ACN + 0.05% TFA; 95:5
(0 min) to 95:5 (0.3 min) to 5:95 (3.5 min) to 5:95 (4 min).

Method H:

YMC

Stationary phase/column: Jsphere
Dimensions: 33*2 mm; 4 μm
Gradient: H$_2$O + 0.1% TFA:ACN + 0.08% TFA;
95:5 (0 min) to 5:95 (2.5 min) to 5:95 (3 min).

TABLE 3

| N° | Method | M + H | Retention time |
|---|---|---|---|
| 1. | D | 431 | 10.40 |
| 2. | A | 365 | 9.70 |
| 3. | D | 365 | 8.80 |
| 4. | D | 415 | 10.00 |
| 5. | D | 381 | 9.80 |
| 6. | D | 365 | 9.00 |
| 7. | D | 381 | 9.70 |
| 8. | C | 415 | 10.50 |
| 9. | D | 427 | 10.00 |
| 10. | D | 372 | 8.30 |
| 11. | E | 399 | 8.50 |
| 12. | D | 387 | 10.50 |
| 13. | D | 387.01 | 10.00 |
| 14. | D | 427 | 11.10 |
| 15. | D | 397 | 11.50 |
| 16. | D | 403 | 10.00 |
| 17. | D | 369 | 8.90 |
| 18. | D | 441 | 10.70 |
| 19. | D | 398 | 5.70 |
| 20. | D | 398 | 5.80 |
| 21. | D | 420 | 9.40 |
| 22. | D | 413 | 10.00 |
| 23. | D | 403 | 10.40 |
| 24. | D | 403 | 9.60 |
| 25. | D | 437 | 11.00 |
| 26. | D | 370 | 6.00 |
| 27. | D | 370 | 5.30 |
| 28. | D | 370 | 5.20 |
| 29. | D | 370 | 5.30 |
| 30. | D | 421 | 10.10 |
| 31. | D | 387 | 9.90 |
| 32. | F | 375.12 | 4.20 |
| 33. | F | 414.98 | 4.10 |
| 34. | F | 414.98 | 4.19 |
| 35. | F | 414.97 | 4.11 |
| 36. | F | 414.99 | 4.17 |
| 37. | F | 415.03 | 4.30 |
| 38. | F | 415.16 | 4.60 |
| 39. | F | 464.05 | 3.95 |
| 40. | F | 453.10 | 4.17 |
| 41. | F | 404.09 | 2.81 |
| 42. | F | 398.09 | 2.52 |
| 43. | F | 398.07 | 2.50 |
| 44. | F | 390.04 | 3.55 |
| 45. | F | 423.09 | 4.14 |
| 46. | F | 403.15 | 4.44 |
| 47. | F | 415.06 | 4.07 |
| 48. | F | 459.19 | 4.90 |
| 49. | F | 437.16 | 4.29 |
| 50. | F | 412.09 | 3.93 |
| 51. | F | 390.10 | 2.86 |
| 52. | F | 372.07 | 3.72 |
| 53. | F | 459.21 | 5.15 |
| 54. | F | 437.15 | 4.27 |
| 55. | H | 454.41 | 2.01 |
| 56. | F | 455.09 | 3.89 |
| 57. | F | 439.09 | 4.19 |
| 58. | F | 398.08 | 2.51 |
| 59. | F | 447.16 | 4.73 |
| 60. | F | 419.15 | 4.29 |
| 61. | F | 398.07 | 2.55 |
| 62. | F | 465.04 | 4.27 |
| 63. | F | 454.08 | 3.17 |
| 64. | F | 460.92 | 4.14 |
| 65. | F | 412.08 | 2.51 |
| 66. | F | 448.07 | 4.04 |
| 67. | F | 422.06 | 3.78 |
| 68. | F | 430.01 | 3.65 |
| 69. | F | 423.12 | 4.24 |
| 70. | F | 423.11 | 4.22 |
| 71. | F | 423.05 | 3.39 |
| 72. | F | 406.01 | 3.66 |
| 73. | F | 418.03 | 3.56 |
| 74. | F | 448.07 | 3.94 |
| 75. | F | 432.10 | 2.82 |
| 76. | F | 448.00 | 3.92 |
| 77. | F | 375.12 | 4.04 |
| 78. | F | 415.00 | 3.91 |
| 79. | F | 397.11 | 4.08 |
| 80. | F | 390.13 | 2.59 |
| 81. | F | 415.06 | 3.97 |
| 82. | F | 437.11 | 4.19 |
| 83. | F | 391.12 | 3.55 |
| 84. | F | 465.20 | 4.44 |
| 85. | F | 439.09 | 4.17 |
| 86. | F | 442.97 | 3.80 |
| 87. | G | 437.11 | 3.87 |
| 88. | G | 439.10 | 3.77 |
| 89. | G | 447.11 | 4.16 |
| 90. | G | 419.12 | 3.85 |
| 91. | G | 437.03 | 4.26 |
| 92. | G | 465.01 | 3.79 |
| 93. | G | 454.11 | 2.85 |
| 94. | G | 460.94 | 3.76 |
| 95. | F | 448.11 | 3.56 |
| 96. | G | 422.09 | 4.31 |
| 97. | G | 430.04 | 3.23 |
| 98. | G | 423.10 | 3.79 |
| 99. | G | 423.10 | 3.78 |
| 100. | G | 406.03 | 3.33 |
| 101. | G | 418.05 | 3.15 |
| 102. | G | 448.09 | 3.51 |
| 103. | G | 432.12 | 2.57 |
| 104. | G | 448.03 | 3.53 |
| 105. | F | 404.13 | 2.55 |
| 106. | F | 397.07 | 3.99 |
| 107. | F | 397.08 | 4.13 |
| 108. | F | 427.08 | 4.03 |
| 109. | G | 415.11 | 4.08 |
| 110. | G | 453.13 | 3.63 |
| 111. | G | 398.11 | 2.39 |
| 112. | G | 398.11 | 2.37 |
| 113. | G | 412.14 | 2.38 |
| 114. | G | 423.08 | 3.08 |
| 115. | H | 415.27 | 2.49 |
| 116. | H | 415.27 | 2.49 |
| 117. | H | 464.38 | 2.34 |
| 118. | H | 390.33 | 2.12 |
| 119. | H | 459.45 | 3.04 |
| 120. | H | 412.36 | 2.37 |
| 121. | H | 459.45 | 2.92 |
| 122. | H | 404.39 | 1.35 |
| 123. | H | 412.36 | 1.36 |
| 124. | H | 372.32 | 2.10 |
| 125. | F | 347.16 | 3.55 |
| 126. | F | 423.20 | 4.12 |
| 127. | F | 390.2 | 2.71 |
| 128. | F | 365.15 | 3.60 |
| 129. | F | 375.20 | 4.06 |
| 130. | F | 404.24 | 2.49 |
| 131. | G | 415.04 | 3.95 |
| 132. | F | 415.10 | 4.01 |
| 133. | F | 415.09 | 3.99 |
| 134. | F | 415.12 | 4.15 |
| 135. | H | 415.11 | 4.38 |
| 136. | F | 397.20 | 3.94 |
| 137. | F | 397.19 | 3.97 |
| 138. | F | 412.20 | 2.43 |
| 139. | F | 464.19 | 3.85 |
| 140. | F | 453.21 | 4.09 |
| 141. | F | 426.16 | 2.82 |
| 142. | F | 398.18 | 2.48 |
| 143. | F | 404.20 | 2.81 |
| 144. | F | 398.19 | 2.47 |
| 145. | F | 398.19 | 2.50 |
| 146. | F | 398.17 | 2.40 |
| 147. | F | 390.22 | 2.57 |
| 148. | F | 390.16 | 3.46 |
| 149. | F | 423.18 | 4.06 |
| 150. | F | 423.20 | 4.09 |
| 151. | F | 415.12 | 3.88 |
| 152. | F | 437.22 | 4.13 |
| 153. | F | 391.20 | 3.53 |
| 154. | F | 415.27 | 4.41 |
| 155. | F | 465.29 | 4.42 |
| 156. | F | 439.20 | 4.08 |

TABLE 3-continued

| N° | Method | M + H | Retention time |
| --- | --- | --- | --- |
| 157. | F | 443.06 | 3.87 |
| 158. | F | 412.21 | 3.85 |
| 159. | F | 372.17 | 3.43 |
| 160. | F | 459.33 | 4.84 |
| 161. | F | 437.23 | 4.15 |
| 162. | F | 453.21 | 3.89 |
| 163. | F | 423.18 | 3.37 |
| 164. | F | 455.2 | 3.70 |
| 165. | F | 439.20 | 4.05 |
| 166. | F | 406.13 | 3.55 |
| 167. | F | 398.18 | 2.49 |
| 168. | F | 447.29 | 4.55 |
| 169. | F | 419.27 | 4.25 |
| 170. | F | 437.23 | 4.56 |
| 171. | F | 418.15 | 3.37 |
| 172. | F | 398.18 | 2.52 |
| 173. | F | 465.15 | 4.07 |
| 174. | F | 461.03 | 4.08 |
| 175. | F | 413.15 | 3.69 |
| 176. | F | 448.20 | 3.86 |
| 177. | F | 422.07 | 3.76 |
| 178. | F | 430.14 | 3.53 |
| 179. | F | 427.21 | 3.88 |
| 180. | F | 448.15 | 3.81 |
| 181. | F | 424.15 | 3.04 |
| 182. | F | 454.23 | 3.11 |
| 183. | F | 448.20 | 3.99 |
| 184. | F | 425.16 | 3.00 |
| 185. | F | 446.13 | 3.44 |
| 186. | F | 386.2 | 3.36 |
| 187. | F | 431.19 | 3.19 |
| 188. | F | 390.15 | 3.36 |
| 189. | F | 403.28 | 4.34 |
| 190. | F | 432.22 | 2.72 |
| 191. | F | 412.20 | 2.49 |
| 192. | F | 430.21 | 3.05 |
| 193. | F | 415.20 | 3.17 |
| 194. | D | 369 | 4.70 |
| 195. | D | 369 | 4.73 |
| 196. | A | 403 | 5.08 |
| 197. | A | 413 | 5.00 |
| 198. | B | 392 | 1.14 |
| 199. | B | 458 | 1.28 |
| 200. | B | 396 | 1.15 |
| 201. | A | 426 | 1.13 |
| 202. | B | 396 | 1.15 |

The compounds of the invention form the subject of pharmacological trials which make it possible to determine their inhibitory effect on the enzyme FAAH (Fatty Acid Amide Hydrolase).

1/Radioenzymatic Test

The inhibitory activity was demonstrated in a radioenzymatic test based on the measurement of the product of hydrolysis of anandamide [ethanolamine 1-$^3$H] by FAAH (*Life Sciences* (1995), 56, 1999-2005 and *Journal of Biochemical and Biophysical Methods* (2004), 60(2), 171-177). Thus, mouse brains (minus the cerebellum) are removed and stored at −80° C. The membrane homogenates are prepared at the time of use by homogenization of the tissues using a Precellys® device in the reaction buffer (Tris-HCl 10 mM pH=8, NaCl 150 mM and ethylenediaminetetraacetic acid (EDTA) 1 mM). The enzymatic reaction is carried out in 96-well MultiScreen filtration plates in a final volume of 70 μl. Reaction buffer supplemented with bovine serum albumin free from fatty acids (BSA, 1 mg/ml) is used for the enzymatic reaction, the dilution of the compounds and the dilution of the anandamide [ethanolamine 1-$^3$H]. Reaction buffer comprising the BSA (43 μl/well), the diluted test compounds at different concentrations (7 μl/well comprising 1% of DMSO) and the membrane preparation (10 μl/well, i.e. 200 μg of tissue per trial) are successively added to the wells. After preincubating the compounds with the enzyme at 25° C. for 20 minutes, the reaction is initiated by the addition of anandamide [ethanolamine 1-$^3$H] (specific activity of 15-20 Ci/mmol) diluted with cold anandamide (10 μl/well, final concentration of 10 μM, 0.01 μCi, per trial). After incubating at 25° C. for 20 minutes, the enzymatic reaction is halted by addition of a 5M active charcoal solution prepared in a 1.5M NaCl and 0.5M HCl buffer (50 μl/well). The mixture is stirred for 10 minutes and then the aqueous phase comprising the [1-$^3$H]ethanolamine is recovered by filtration under vacuum and counted by liquid scintillation.

Under these conditions, the most active compounds of the invention exhibit $CI_{50}$ values (concentration which inhibits the control enzymatic activity of FAAH by 50%) of between 0.1 and 1000 nM, preferably between 0.1 and 500 nM, preferably between 0.2 and 100 nM, indeed even between 0.2 and 50 nM. For example, compounds No. 26, No. 38, No. 39, No. 49, No. 60, No. 90, No. 196, No. 199, No. 200 and No. 202 have respective $CI_{50}$ values of 86 nM, 14 nM, 13 nM, 19 nM, 95 nM, 92 nM, 252 nM, 350 nM, 122 nM and 8 nM.

It is thus apparent that the compounds according to the invention have an inhibitory activity on the enzyme FAAH.

The in vivo activity of the compounds of the invention can be evaluated in a test for analgesia.

2/Test for Analgesia

The intraperitoneal (i.p.) administration of PBQ (phenylbenzoquinone, 2 mg/kg in a 0.9% sodium chloride solution comprising 5% of ethanol) to male OF1 mice weighing to 30 g causes abdominal tractions, on average 30 twisting or contracting motions during the period from 5 to minutes after injection. The test compounds are administered, orally (p.o.) or intraperitoneally (i.p.) in suspension in 0.5% Tween 80, 60 minutes or 120 minutes before the administration of PBQ. Under these conditions, the most powerful compounds reduce by 30 to 80% the number of tractions induced by the PBQ, within a range of doses of between 1 and 30 mg/kg.

The enzyme FAAH (*Chemistry and Physics of Lipids*, (2000), 108, 107-121) catalyses the hydrolysis of endogenous derivatives of amides and esters of various fatty acids, such as N-arachidonoylethanolamine (anandamide), N-palmitoylethanolamine, N-oleoylethanolamine, oleamide or 2-arachidonoylglycerol. These derivatives exert various pharmacological activities by interacting, inter alia, with the cannabinoid and vanilloid receptors.

The compounds of the invention block this decomposition pathway and increase the tissue level of these endogenous substances. They can therefore be used in the prevention and treatment of pathologies in which endogenous cannabinoids and/or any other substrate metabolized by the enzyme FAAH are involved. Mention may be made, for example, of the following diseases and conditions:

pain, in particular acute or chronic pain of neurogenic type: migraine, neuropathic pain, including forms associated with the herpes virus and with diabetes and with chemotherapy; acute or chronic pain associated with inflammatory diseases: arthritis, rheumatoid arthritis, osteoarthritis, spondylitis, gout, vasculitis, Crohn's disease, irritable bowel syndrome; acute or chronic peripheral pain; dizziness, vomiting, nausea, in particular resulting from chemotherapy; eating disorders, in particular anorexia and cachexia of various natures; neurological and psychiatric pathologies: tremors, dyskinesias, dystonias, spasticity, obsessive-compulsive behaviour, Tourette's syndrome, all forms of depression and of anxiety of any nature and origin, mood disorders, psychoses; acute or chronic neurodegenerative diseases: Parkinson's disease, Alzheimer's disease, senile dementia, Huntington's chorea, lesions related to cerebral ischaemia and to cranial and medullary trauma; epilepsy; sleep disorders, including sleep apnoea; cardiovascular diseases, in particular hypertension, cardiac arrhythmias, arteriosclerosis, heart attack, cardiac ischaemia; renal ischaemia; cancers: benign skin tumours, brain tumours and papillomas, prostate tumours, cerebral tumours (glioblastomas, medulloepitheliomas, medulloblastomas, neuroblastomas, tumours of embryonic origin, astrocytomas, astroblastomas, ependymomas, oligodendrogliomas, plexus tumour, neuroepitheliomas, epiphyseal tumour, ependymoblastomas, malignant meningiomas, sarcomatosis, malignant melanomas, schwannomas); disorders of the immune system, in particular autoimmune diseases: psoriasis, lupus erythematosus, diseases of the connective tissue or collagen diseases, Sjögren's syndrome, ankylosing spondylitis, undifferentiated spondylitis, Behcet's disease, autoimmune haemolytic anaemia, multiple sclerosis, amyotrophic lateral sclerosis, amyloidosis, graft rejection, diseases affecting the plasmocytic line; allergic diseases: immediate or delayed hypersensitivity, allergic rhinitis or conjunctivitis, contact dermatitis; parasitic, viral or bacterial infectious diseases: AIDS, meningitis; inflammatory diseases, in particular joint diseases: arthritis, rheumatoid arthritis, osteoarthritis, spondylitis, gout, vasculitis, Crohn's disease, irritable bowel syndrome; osteoporosis; eye conditions: ocular hypertension, glaucoma; pulmonary conditions: diseases of the respiratory tract, bronchospasm, coughing, asthma, chronic bronchitis, chronic obstruction of the respiratory tract, emphysema; gastrointestinal diseases: irritable bowel syndrome, inflammatory intestinal disorders, ulcers, diarrhoea; urinary incontinence and bladder inflammation.

The use of the compounds according to the invention, in the form of the base, of an addition salt with an acid, of a hydrate or of a solvate which is pharmaceutically acceptable, in the preparation of a medicament intended to treat the abovementioned pathologies forms an integral part of the invention.

Compounds according to the invention, in the form of the base, of an addition salt with an acid, of a hydrate or of a solvate which is pharmaceutically acceptable, for their use in the preparation of a medicament intended to treat the abovementioned pathologies forms an integral part of the invention.

Another subject-matter of the invention is medicaments which comprise a compound of formula (I), (Ii) or (Iii), or an addition salt with an acid, or a hydrate or a solvate which is pharmaceutically acceptable of the compound of formula (I), (Ii) or (Iii). These medicaments are used therapeutically, in particular in the treatment of the abovementioned pathologies.

According to another of its aspects, the present invention relates to pharmaceutical compositions including, as active principle, at least one compound according to the invention. These pharmaceutical compositions comprise an effective dose of a compound according to the invention, or an addition salt with an acid, or a hydrate, or a solvate which is pharmaceutically acceptable of the said compound, and optionally one or more pharmaceutically acceptable excipients.

The said excipients are chosen, depending on the pharmaceutical form and the method of administration desired, from the usual excipients which are known to a person skilled in the art.

In the pharmaceutical compositions of the present invention for oral, sublingual, subcutaneous, intramuscular, intravenous, topical, local, intrathecal, intranasal, transdermal, pulmonary, ocular or rectal administration, the active principle of formula (I), (Ii) or (Iii) above or its optional addition salt with an acid, solvate or hydrate can be administered in a unit administration form, as a mixture with conventional pharmaceutical excipients, to animals and to man for the prophylaxis or the treatment of the above disorders or diseases.

Appropriate unit administration forms comprise oral forms, such as tablets, soft or hard gelatin capsules, powders, granules, chewing gums and oral solutions or suspensions, forms for sublingual, buccal, intratracheal, intraocular or intranasal administration or for administration by inhalation, forms for subcutaneous, intramuscular or intravenous administration and forms for rectal or vaginal administration. For topical application, the compounds according to the invention can be used in creams, ointments or lotions.

By way of example, a unit administration form of a compound according to the invention in the form of a tablet can comprise the following components:

| | |
|---|---|
| Compound according to the invention | 50.0 mg |
| Mannitol | 223.75 mg |
| Croscarmellose sodium | 6.0 mg |
| Maize starch | 15.0 mg |
| Hydroxypropylmethylcellulose | 2.25 mg |
| Magnesium stearate | 3.0 mg |

The said unit forms comprise a dose which makes possible a daily administration of 0.01 to 20 mg of active principle per kg of body weight, depending upon the pharmaceutical dosage form.

There may be specific cases where higher or lower dosages are appropriate; such dosages also come within the invention. According to the usual practice, the dosage appropriate to each patient is determined by the doctor according to the method of administration and the weight and the response of the said patient.

According to another of its aspects, the invention also relates to a method for the treatment of the pathologies indicated above which comprises the administration of an effective dose of a compound according to the invention, of one of its addition salts with a pharmaceutically acceptable acid or of a solvate or of a hydrate of the said compound.

The invention claimed is:

1. A compound according to the formula (I):

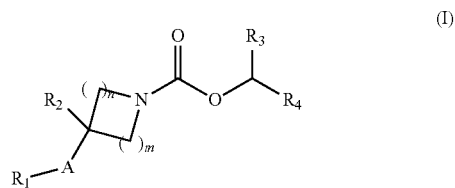

in which:
R$_2$ represents a hydrogen or fluorine atom or a hydroxyl, cyano, trifluoromethyl, C$_{1-6}$-alkyl, C$_{1-6}$-alkoxy or —NR$_8$R$_9$ group;
n and m represent an integer equal to 2;
A represents an —O—C$_{1-6}$-alkylene group in which the end represented by an oxygen atom is bonded to the R$_1$ group;
R$_1$ represents an R$_5$ group optionally substituted by one or more R$_6$ and/or R$_7$ groups;
R$_5$ representing a group chosen from a phenyl or benzothiazolyl;
R$_6$ representing a halogen atom or a cyano, —CH$_2$CN, nitro, hydroxyl, C$_{1-8}$-alkyl, C$_{1-6}$-alkoxy, C$_{1-6}$-haloalkyl, C$_{1-6}$-haloalkoxy, C$_{1-6}$-halothioalkyl, C$_{3-7}$-cycloalkyl, C$_{3-7}$-cycloalkyl-C$_{1-3}$-alkylene, C$_{3-7}$-cycloalkyl-C$_{1-3}$-alkylene-O—, —(CH$_2$)$_p$—NR$_8$R$_9$, —NR$_8$COR$_9$, —NR$_8$CO$_2$R$_9$, —NR$_8$SO$_2$R$_9$, —NR$_8$SO$_2$NR$_8$R$_9$, —COR$_8$, —CO$_2$R$_8$, —(CH$_2$)$_p$—CONR$_8$R$_9$, —SO$_2$R$_8$, —SO$_2$NR$_8$R$_9$ or —O—(C$_{1-3}$-alkylene)-O— group;

R₇ representing a group chosen from a phenyl, phenyl-$C_{1-4}$-alkylene-, phenyl-$(CH_2)_p$—O—, pyridinyl, pyridazinyl, pyrimidinyl, pyrazinyl, triazinyl, furanyl, thienyl, imidazolyl, oxazolyl, isoxazolyl, pyrrolyl, pyrazolyl, tetrazolyl, thiazolyl, isothiazolyl, oxadiazolyl, thiadiazolyl, imidazopyrimidinyl, thienopyrimidinyl, benzofuranyl, benzothienyl, benzimidazolyl, benzoxazolyl, benzisoxazolyl, benzothiazolyl, benzisothiazolyl, indolyl, isoindolyl, indazolyl, pyrrolopyridinyl, furopyridinyl, thienopyridinyl, imidazopyridinyl, pyrazolopyridinyl, oxazolopyridinyl, isoxazolopyridinyl or thiazolopyridinyl; it being possible for the R₇ group or groups to be substituted by one or more R₆ groups which are identical to or different from one another;

p representing a number which can have the value 0, 1, 2 or 3;

R₃ represents a hydrogen or fluorine atom, a $C_{1-6}$-alkyl group or a trifluoromethyl group;

R₄ represents a 5-membered heterocycle chosen from thiazolyl, or isoxazolyl;

this heterocycle optionally being substituted by one or more substituents chosen from a halogen atom or a $C_{1-6}$-alkyl, $C_{1-6}$-haloalkyl, $C_{3-7}$-cycloalkyl, $C_{3-7}$-cycloalkyl-$C_{1-3}$-alkylene, $C_{1-6}$-haloalkoxy, cyano, —NR₈R₉, —NR₈C(O)R₉, —NR₈CO₂R₉, —NR₈SO₂R₉, —NR₈SO₂NR₈R₉, —C(O)R₈, —CO₂R₈, —C(O)NR₈R₉, —C(O)N(R₈)($C_{1-3}$-alkylene-NR₁₀R₁₁), —SO₂R₈, —SO₂NR₈R₉ or —O—($C_{1-3}$-alkylene)-O— group;

R₈ and R₉ representing, independently of one another, a hydrogen atom or a $C_{1-6}$-alkyl group, R₁₀ and R₁₁ representing, independently of one another, a hydrogen atom or a $C_{1-6}$-alkyl group;

with the exclusion of the following compound:

5-methylisoxazol-3-ylmethyl 4-hydroxy-4-(4-chlorophenyl)piperidine-1-carboxylate, in the form of the base or of an addition salt with an acid.

2. The compound of formula (I) according to claim 1, wherein R₂ represents a hydrogen atom; in the form of the base or of an addition salt with an acid.

3. The compound of formula (I) according to claim 1, wherein R₃ represents a hydrogen atom;

in the form of the base or of an addition salt with an acid.

4. The compound of formula (I) according to claim 1, wherein R₄ represents a 5-membered heterocycle chosen from a thiazolyl or isoxazolyl;

this heterocycle optionally being substituted by one or more —C(O)NR₈R₉ substituents in which R₈ and R₉ each represent a hydrogen atom;

in the form of the base or of an addition salt with an acid.

5. The compound according to claim 1, wherein compound is of formula (Ii):

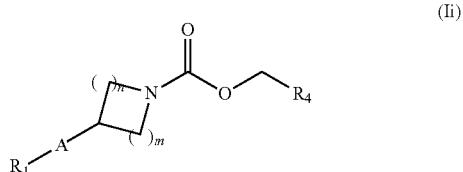

(Ii)

in which R₁, A, R₄, n and m are as defined in claim 1;

in the form of the base or of an addition salt with an acid.

6. The compound according to claim 1, wherein the compound is of formula (Iii):

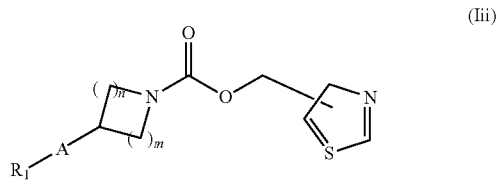

(Iii)

in which R₁, A, n and m are as defined in claim 1;

in the form of the base or of an addition salt with an acid.

7. A compound chosen from the group consisting of:

Thiazol-2-ylmethyl 4-[2-(4-chloronaphth-1-yloxy)ethyl]piperidine-1-carboxylate,

Thiazol-2-ylmethyl 4-[2-(4-fluorophenoxy)ethyl]piperidine-1-carboxylate,

Thiazol-4-ylmethyl 4-[2-(4-fluorophenoxy)ethyl]piperidine-1-carboxylate,

Thiazol-4-ylmethyl 4-[2-(4-{trifluoromethyl}phenoxy)ethyl]piperidine-1-carboxylate, Thiazol-4-ylmethyl 4-[2-(4-chlorophenoxy)ethyl]piperidine-1-carboxylate, Thiazol-5-ylmethyl 4-[2-(4-fluorophenoxy)ethyl]piperidine-1-carboxylate, Thiazol-5-ylmethyl 4-[2-(4-chlorophenoxy)ethyl]piperidine-1-carboxylate, Thiazol-5-ylmethyl 4-[2-(4-{trifluoromethyl}phenoxy)ethyl]piperidine-1-carboxylate, Thiazol-4-ylmethyl 4-[2-(7-methoxynaphth-2-yloxy)ethyl]piperidine-1-carboxylate, Thiazol-4-ylmethyl 4-[2-(4-cyanophenoxy)ethyl]piperidine-1-carboxylate, Thiazol-4-ylmethyl (+/−)-3-(6-methoxynaphth-2-yloxymethyl)pyrrolidine-1-carboxylate, Thiazol-4-ylmethyl (+/−)-3-(7-methoxynaphth-2-yloxymethyl)pyrrolidine-1-carboxylate, Thiazol-4-ylmethyl (+/−)-3-(3,4-dichlorophenoxymethyl)pyrrolidine-1-carboxylate, Thiazol-4-ylmethyl 4-[2-(6-methoxynaphth-2-yloxy)ethyl]piperidine-1-carboxylate, Thiazol-4-ylmethyl 4-[2-(naphth-2-yloxy)ethyl]piperidine-1-carboxylate, Thiazol-4-ylmethyl (+/−)-3-(4-chloronaphth-1-yloxymethyl)pyrrolidine-1-carboxylate, Thiazol-4-ylmethyl (+/−)-3-(naphth-2-yloxymethyl)pyrrolidine-1-carboxylate, Thiazol-4-ylmethyl 4-[2-(4'-fluorobiphenyl-4-yloxy)ethyl]piperidine-1-carboxylate, Thiazol-4-ylmethyl 4-[2-(quinolin-6-yloxy)ethyl]piperidine-1-carboxylate and its hydrochloride, Thiazol-4-ylmethyl 4-[2-(isoquinolin-6-yloxy)ethyl]piperidine-1-carboxylate and its hydrochloride, Thiazol-4-ylmethyl (+/−)-3-(3'-cyanobiphenyl-3-yloxymethyl)pyrrolidine-1-carboxylate, Thiazol-4-ylmethyl (+/−)-3-(4'-fluorobiphenyl-4-yloxymethyl)pyrrolidine-1-carboxylate, Thiazol-4-ylmethyl (+/−)-3-(5-chloronaphth-2-yloxymethyl)pyrrolidine-1-carboxylate, Thiazol-4-ylmethyl (+/−)-3-(3-{trifluoromethoxy}phenoxymethyl)pyrrolidine-1-carboxylate, Thiazol-4-ylmethyl (+/−)-3-[4-(1-methyl-1-phenylethyl)phenoxymethyl]pyrrolidine-1-carboxylate, Thiazol-4-ylmethyl (+/−)-3-(quinolin-3-yloxymethyl)pyrrolidine-1-carboxylate,
Thiazol-4-ylmethyl (+/−)-3-(isoquinolin-6-yloxymethyl)pyrrolidine-1-carboxylate,
Thiazol-4-ylmethyl (+/−)-3-(quinolin-7-yloxymethyl)pyrrolidine-1-carboxylate,
Thiazol-4-ylmethyl (+/−)-3-(isoquinolin-7-yloxymethyl)pyrrolidine-1-carboxylate,
Thiazol-4-ylmethyl (+/−)-3-(4-chloro-3-{trifluoromethyl}phenoxymethyl)pyrrolidine-1-carboxylate,
Thiazol-4-ylmethyl (+/−)-3-(5-fluoronaphth-2-yloxymethyl)pyrrolidine-1-carboxylate,
Thiazol-2-ylmethyl 4-[2-(2,4-dimethylphenoxy)ethyl]piperidine-1-carboxylate,
Thiazol-2-ylmethyl 4-[2-(2,3-dichlorophenoxy)ethyl]piperidine-1-carboxylate,
Thiazol-2-ylmethyl 4-[2-(2,4-dichlorophenoxy)ethyl]piperidine-1-carboxylate,
Thiazol-2-ylmethyl 4-[2-(2,5-dichlorophenoxy)ethyl]piperidine-1-carboxylate,
Thiazol-2-ylmethyl 4-[2-(3,4-dichlorophenoxy)ethyl]piperidine-1-carboxylate,
Thiazol-2-ylmethyl 4-[2-(3,5-dichlorophenoxy)ethyl]piperidine-1-carboxylate,
Thiazol-2-ylmethyl 4-[2-(4-cyclopentylphenoxy)ethyl]piperidine-1-carboxylate,
Thiazol-2-ylmethyl 4-[2-(2-{benzoxazol-2-yl}phenoxy)ethyl]piperidine-1-carboxylate,
Thiazol-2-ylmethyl 4-[2-(4-{benzyloxy}phenoxy)ethyl]piperidine-1-carboxylate,
Thiazol-2-ylmethyl 4-[2-(4-{carbamoylmethyl}phenoxy)ethyl]piperidine-1-carboxylate,
Thiazol-2-ylmethyl 4-[2-(quinolin-7-yloxy)ethyl]piperidine-1-carboxylate and its trifluoroacetate,
Thiazol-2-ylmethyl 4-[2-(quinolin-6-yloxy)ethyl]piperidine-1-carboxylate and its trifluoroacetate,
Thiazol-2-ylmethyl 4-[2-(4-cyano-3-fluorophenoxy)ethyl]piperidine-1-carboxylate,
Thiazol-2-ylmethyl 4-[2-(biphenyl-2-yloxy)ethyl]piperidine-1-carboxylate,
Thiazol-2-ylmethyl 4-[2-(2-isopropyl-5-methylphenoxy)ethyl]piperidine-1-carboxylate,
Thiazol-2-ylmethyl 4-[2-(3-{trifluoromethyl}phenoxy)ethyl]piperidine-1-carboxylate,
Thiazol-2-ylmethyl 4-{2-[4-(1,1,3,3-tetramethylbutyl)phenoxy]ethyl}piperidine-1-carboxylate,
Thiazol-2-ylmethyl 4-[2-(4-benzylphenoxy)ethyl]piperidine-1-carboxylate,
Thiazol-2-ylmethyl 4-[2-(4-{pyrrol-1-yl}phenoxy)ethyl]piperidine-1-carboxylate and its trifluoroacetate,
Thiazol-2-ylmethyl 4-[2-(4-carbamoylphenoxy)ethyl]piperidine-1-carboxylate,
Thiazol-2-ylmethyl 4-[2-(3-cyanophenoxy)ethyl]piperidine-1-carboxylate,
Thiazol-2-ylmethyl 4-[2-(3,5-di{tert-butyl}phenoxy)ethyl]piperidine-1-carboxylate,
Thiazol-2-ylmethyl 4-[2-(2-benzylphenoxy)ethyl]piperidine-1-carboxylate,
Thiazol-2-ylmethyl 4-[2-(8-{acetylamino}naphth-2-yloxy)ethyl]piperidine-1-carboxylate,
Thiazol-2-ylmethyl 4-[2-(3-{methoxycarbonyl}naphth-2-yloxy)ethyl]piperidine-1-carboxylate,
Thiazol-2-ylmethyl 4-[2-(3-phenoxyphenoxy)ethyl]piperidine-1-carboxylate,
Thiazol-2-ylmethyl 4-[2-(isoquinolin-7-yloxy)ethyl]piperidine-1-carboxylate and its trifluoroacetate,
Thiazol-2-ylmethyl 4-[2-(4-hexyloxyphenoxy)ethyl]piperidine-1-carboxylate,
Thiazol-2-ylmethyl 4-[2-(3-butoxyphenoxy)ethyl]piperidine-1-carboxylate,
Thiazol-2-ylmethyl 4-[2-(quinolin-5-yloxy)ethyl]piperidine-1-carboxylate and its trifluoroacetate,
Thiazol-2-ylmethyl 4-[2-(3-{pentafluoroethyl}phenoxy)ethyl]piperidine-1-carboxylate,
Thiazol-2-ylmethyl 4-[2-(5-{acetylamino}naphth-2-yloxy)ethyl]piperidine-1-carboxylate,
Thiazol-2-ylmethyl 4-[2-(5-bromo-2-chlorophenoxy)ethyl]piperidine-1-carboxylate,
Thiazol-2-ylmethyl 4-[2-(2-methylquinolin-6-yloxy)ethyl]piperidine-1-carboxylate and its trifluoroacetate,
Thiazol-2-ylmethyl 4-[2-(4'-cyanobiphenyl-3-yloxy)ethyl]piperidine-1-carboxylate,
Thiazol-2-ylmethyl 4-[2-(6-cyanonaphth-2-yloxy)ethyl]piperidine-1-carboxylate,
Thiazol-2-ylmethyl 4-[2-(4-{thiazol-2-yl}phenoxy)ethyl]piperidine-1-carboxylate,
Thiazol-2-ylmethyl 4-[2-(biphenyl-3-yloxy)ethyl]piperidine-1-carboxylate,
Thiazol-2-ylmethyl 4-[2-(biphenyl-4-yloxy)ethyl]piperidine-1-carboxylate,
Thiazol-2-ylmethyl 4-[2-(2-cyanoquinolin-8-yloxy)ethyl]piperidine-1-carboxylate and its trifluoroacetate,
Thiazol-2-ylmethyl 4-[2-(4-chloro-2-cyanophenoxy)ethyl]piperidine-1-carboxylate and its trifluoroacetate,
Thiazol-2-ylmethyl 4-[2-(2-methylbenzothiazol-5-yloxy)ethyl]piperidine-1-carboxylate,
Thiazol-2-ylmethyl 4-[2-(4'-cyanobiphenyl-4-yloxy)ethyl]piperidine-1-carboxylate,
Thiazol-2-ylmethyl 4-[2-(2-{morpholin-4-yl}phenoxy)ethyl]piperidine-1-carboxylate,
Thiazol-2-ylmethyl 4-[2-(4-chloro-2-{isoxazol-5-yl}phenoxy)ethyl]piperidine-1-carboxylate,
Thiazol-4-ylmethyl 4-[2-(2,4-dimethylphenoxy)ethyl]piperidine-1-carboxylate,
Thiazol-4-ylmethyl 4-[2-(2,3-dichlorophenoxy)ethyl]piperidine-1-carboxylate,
Thiazol-4-ylmethyl 4-[2-(naphth-1-yloxy)ethyl]piperidine-1-carboxylate,
Thiazol-4-ylmethyl 4-[2-(3-{dimethylamino}phenoxy)ethyl]piperidine-1-carboxylate and its trifluoroacetate,
Thiazol-4-ylmethyl 4-[2-(3-{trifluoromethyl}phenoxy)ethyl]piperidine-1-carboxylate,
Thiazol-4-ylmethyl 4-[2-(4-benzylphenoxy)ethyl]piperidine-1-carboxylate,
Thiazol-4-ylmethyl 4-[2-(2-ethoxyphenoxy)ethyl]piperidine-1-carboxylate,
Thiazol-4-ylmethyl 4-{2-[4-(1-methyl-1-phenylethyl)phenoxy]ethyl}piperidine-1-carboxylate,
Thiazol-4-ylmethyl 4-[2-(4-phenoxyphenoxy)ethyl]piperidine-1-carboxylate,
Thiazol-4-ylmethyl 4-[2-(2-bromo-4-fluorophenoxy)ethyl]piperidine-1-carboxylate,
Thiazol-4-ylmethyl 4-[2-(2-benzylphenoxy)ethyl]piperidine-1-carboxylate,
Thiazol-4-ylmethyl 4-[2-(3-phenoxyphenoxy)ethyl]piperidine-1-carboxylate,
Thiazol-4-ylmethyl 4-[2-(4-{hexyloxy}phenoxy)ethyl]piperidine-1-carboxylate,
Thiazol-4-ylmethyl 4-[2-(3-butoxyphenoxy)ethyl]piperidine-1-carboxylate,
Thiazol-4-ylmethyl 4-[2-(4-chloro-5-isopropyl-2-methylphenoxy)ethyl]piperidine-1-carboxylate, Thiazol-4-ylmethyl 4-[2-(3-{pentafluoroethyl}phenoxy)ethyl]piperidine-1-carboxylate,
Thiazol-4-ylmethyl 4-[2-(5-{acetylamino}naphth-2-yloxy)ethyl]piperidine-1-carboxylate,
Thiazol-4-ylmethyl 4-[2-(5-bromo-2-chlorophenoxy)ethyl]piperidine-1-carboxylate,
Thiazol-4-ylmethyl 4-[2-(4'-cyanobiphenyl-3-yloxy)ethyl]piperidine-1-carboxylate,
Thiazol-4-ylmethyl 4-[2-(6-cyanonaphth-2-yloxy)ethyl]piperidine-1-carboxylate,
Thiazol-4-ylmethyl 4-[2-(4-{thiazol-2-yl}phenoxy)ethyl]piperidine-1-carboxylate,
Thiazol-4-ylmethyl 4-[2-(biphenyl-3-yloxy)ethyl]piperidine-1-carboxylate,
Thiazol-4-ylmethyl 4-[2-(biphenyl-4-yloxy)ethyl]piperidine-1-carboxylate,
Thiazol-4-ylmethyl 4-[2-(4-chloro-2-cyanophenoxy)ethyl]piperidine-1-carboxylate,
Thiazol-4-ylmethyl 4-[2-(2-methylbenzothiazol-5-yloxy)ethyl]piperidine-1-carboxylate,
Thiazol-4-ylmethyl 4-[2-(4'-cyanobiphenyl-4-yloxy)ethyl]piperidine-1-carboxylate,
Thiazol-4-ylmethyl 4-[2-(2-{morpholin-4-yl}phenoxy)ethyl]piperidine-1-carboxylate and its trifluoroacetate,
Thiazol-4-ylmethyl 4-[2-(4-chloro-2-{isoxazol-5-yl}phenoxy)ethyl]piperidine-1-carboxylate,
Thiazol-2-ylmethyl 4-[2-(4-{dimethylaminomethyl}phenoxy)ethyl]piperidine-1-carboxylate and its trifluoroacetate,
Thiazol-2-ylmethyl 4-[2-(naphth-2-yloxy)ethyl]piperidine-1-carboxylate,
Thiazol-2-ylmethyl 4-[2-(naphth-1-yloxy)ethyl]piperidine-1-carboxylate,
Thiazol-2-ylmethyl 4-[2-(7-methoxynaphth-2-yloxy)ethyl]piperidine-1-carboxylate,
Thiazol-4-ylmethyl 4-[2-(2-cyclopentylphenoxy)ethyl]piperidine-1-carboxylate,
Thiazol-4-ylmethyl 4-[2-(2-benzyloxyphenoxy)ethyl]piperidine-1-carboxylate,
Thiazol-4-ylmethyl 4-[2-(isoquinolin-7-yloxy)ethyl]piperidine-1-carboxylate and its trifluoroacetate,
Thiazol-4-ylmethyl 4-[2-(quinolin-5-yloxy)ethyl]piperidine-1-carboxylate and its trifluoroacetate,
Thiazol-4-ylmethyl 4-[2-(2-methylquinolin-6-yloxy)ethyl]piperidine-1-carboxylate and its trifluoroacetate,
Thiazol-4-ylmethyl 4-[2-(2-cyanoquinolin-8-yloxy)ethyl]piperidine-1-carboxylate and its trifluoroacetate,
Thiazol-4-ylmethyl 4-[2-(2,4-dichlorophenoxy)ethyl]piperidine-1-carboxylate,
Thiazol-4-ylmethyl 4-[2-(4-cyclopentylphenoxy)ethyl]piperidine-1-carboxylate,
Thiazol-4-ylmethyl 4-[2-(2-{benzoxazol-2-yl}phenoxy)ethyl]piperidine-1-carboxylate,
Thiazol-4-ylmethyl 4-[2-(4-cyano-3-fluorophenoxy)ethyl]piperidine-1-carboxylate,
Thiazol-4-ylmethyl 4-{2-[4-(1,1,3,3-tetramethylbutyl)phenoxy]ethyl}piperidine-1-carboxylate,
Thiazol-4-ylmethyl 4-[2-(4-{pyrrol-1-yl}phenoxy)ethyl]piperidine-1-carboxylate and its trifluoroacetate,
Thiazol-4-ylmethyl 4-[2-(3,5-di{tert-butyl}-phenoxy)ethyl]piperidine-1-carboxylate,
Thiazol-4-ylmethyl 4-[2-(4-{dimethylaminomethyl}phenoxy)ethyl]piperidine-1-carboxylate and its trifluoroacetate,
Thiazol-4-ylmethyl 4-[2-(2-methylquinolin-8-yloxy)ethyl]piperidine-1-carboxylate and its trifluoroacetate,
Thiazol-4-ylmethyl 4-[2-(3-cyanophenoxy)ethyl]piperidine-1-carboxylate,
Thiazol-5-ylmethyl 4-(2-phenoxyethyl)piperidine-1-carboxylate,
Thiazol-5-ylmethyl 4-[2-(biphenyl-4-yloxy)ethyl]piperidine-1-carboxylate,
Thiazol-5-ylmethyl 4-[2-(4-carbamoylphenoxy)ethyl]piperidine-1-carboxylate,
Thiazol-5-ylmethyl 4-[2-(4-fluorophenoxy)ethyl]piperidine-1-carboxylate,
Thiazol-5-ylmethyl 4-[2-(2,4-dimethylphenoxy)ethyl]piperidine-1-carboxylate,
Thiazol-5-ylmethyl 4-[2-(4-{dimethylaminomethyl}phenoxy)ethyl]piperidine-1-carboxylate and its trifluoroacetate,
Thiazol-5-ylmethyl 4-[2-(2,3-dichlorophenoxy)ethyl]piperidine-1-carboxylate,
Thiazol-5-ylmethyl 4-[2-(2,4-dichlorophenoxy)ethyl]piperidine-1-carboxylate,
Thiazol-5-ylmethyl 4-[2-(2,5-dichlorophenoxy)ethyl]piperidine-1-carboxylate,
Thiazol-5-ylmethyl 4-[2-(3,5-dichlorophenoxy)ethyl]piperidine-1-carboxylate,
Thiazol-5-ylmethyl 4-[2-(4-cyclopentylphenoxy)ethyl]piperidine-1-carboxylate,
Thiazol-5-ylmethyl 4-[2-(naphth-2-yloxy)ethyl]piperidine-1-carboxylate,
Thiazol-5-ylmethyl 4-[2-(naphth-1-yloxy)ethyl]piperidine-1-carboxylate,
Thiazol-5-ylmethyl 4-[2-(2-methylquinolin-8-yloxy)ethyl]piperidine-1-carboxylate,
Thiazol-5-ylmethyl 4-[2-(2-{benzoxazol-2-yl}phenoxy)ethyl]piperidine-1-carboxylate,
Thiazol-5-ylmethyl 4-[2-(4-{benzyloxy}phenoxy)ethyl]piperidine-1-carboxylate,
Thiazol-5-ylmethyl 4-[2-(4-sulphamoylphenoxy)ethyl]piperidine-1-carboxylate,
Thiazol-5-ylmethyl 4-[2-(isoquinolin-5-yloxy)ethyl]piperidine-1-carboxylate,
Thiazol-5-ylmethyl 4-[2-(4-{carbamoylmethyl}phenoxy)ethyl]piperidine-1-carboxylate,
Thiazol-5-ylmethyl 4-[2-(quinolin-7-yloxy)ethyl]piperidine-1-carboxylate,
Thiazol-5-ylmethyl 4-[2-(quinolin-6-yloxy)ethyl]piperidine-1-carboxylate,
Thiazol-5-ylmethyl 4-[2-(quinolin-8-yloxy)ethyl]piperidine-1-carboxylate,
Thiazol-5-ylmethyl 4-[2-(3-{dimethylamino}phenoxy)ethyl]piperidine-1-carboxylate and its trifluoroacetate,
Thiazol-5-ylmethyl 4-[2-(4-cyano-3-fluorophenoxy)ethyl]piperidine-1-carboxylate,
Thiazol-5-ylmethyl 4-[2-(biphenyl-2-yloxy)ethyl]piperidine-1-carboxylate,
Thiazol-5-ylmethyl 4-[2-(biphenyl-3-yloxy)ethyl]piperidine-1-carboxylate,
Thiazol-5-ylmethyl 4-[2-(3-{trifluoromethyl}phenoxy)ethyl]piperidine-1-carboxylate,
Thiazol-5-ylmethyl 4-[2-(4-benzylphenoxy)ethyl]piperidine-1-carboxylate,
Thiazol-5-ylmethyl 4-[2-(2-ethoxyphenoxy)ethyl]piperidine-1-carboxylate,
Thiazol-5-ylmethyl 4-[2-(2-cyclopentylphenoxy)ethyl]piperidine-1-carboxylate,
Thiazol-5-ylmethyl 4-{2-[4-(1-methyl-1-phenylethyl)phenoxy]ethyl}piperidine-1-carboxylate,
Thiazol-5-ylmethyl 4-[2-(4-phenoxyphenoxy)ethyl]piperidine-1-carboxylate, Thiazol-5-ylmethyl 4-[2-(2-bromo-4-fluorophenoxy)ethyl]piperidine-1-carboxylate,
Thiazol-5-ylmethyl 4-[2-(4-{pyrrol-1-yl}phenoxy)ethyl]piperidine-1-carboxylate,
Thiazol-5-ylmethyl 4-[2-(3-cyanophenoxy)ethyl]piperidine-1-carboxylate,
Thiazol-5-ylmethyl 4-[2-(3,5-di{tert-butyl}phenoxy)ethyl]piperidine-1-carboxylate,
Thiazol-5-ylmethyl 4-[2-(2-benzylphenoxy)ethyl]piperidine-1-carboxylate,
Thiazol-5-ylmethyl 4-[2-(2-{benzyloxy}phenoxy)ethyl]piperidine-1-carboxylate,
Thiazol-5-ylmethyl 4-[2-(2-cyanoquinolin-8-yloxy)ethyl]piperidine-1-carboxylate,
Thiazol-5-ylmethyl 4-[2-(3-{methoxycarbonyl}naphth-2-yloxy)ethyl]piperidine-1-carboxylate,
Thiazol-5-ylmethyl 4-[2-(3-phenoxyphenoxy)ethyl]piperidine-1-carboxylate,
Thiazol-5-ylmethyl 4-[2-(4-chloro-2-cyanophenoxy)ethyl]piperidine-1-carboxylate,
Thiazol-5-ylmethyl 4-[2-(isoquinolin-7-yloxy)ethyl]piperidine-1-carboxylate,
Thiazol-5-ylmethyl 4-[2-(4-{hexyloxy}phenoxy)ethyl]piperidine-1-carboxylate,
Thiazol-5-ylmethyl 4-[2-(3-butoxyphenoxy)ethyl]piperidine-1-carboxylate,
Thiazol-5-ylmethyl 4-[2-(4-chloro-5-isopropyl-2-methylphenoxy)ethyl]piperidine-1-carboxylate,
Thiazol-5-ylmethyl 4-[2-(2-methylbenzothiazol-5-yloxy)ethyl]piperidine-1-carboxylate,
Thiazol-5-ylmethyl 4-[2-(quinolin-5-yloxy)ethyl]piperidine-1-carboxylate,
Thiazol-5-ylmethyl 4-[2-(3-{pentafluoroethyl}phenoxy)ethyl]piperidine-1-carboxylate,
Thiazol-5-ylmethyl 4-[2-(5-bromo-2-chlorophenoxy)ethyl]piperidine-1-carboxylate,
Thiazol-5-ylmethyl 4-[2-(4-{difluoromethoxy}phenoxy)ethyl]piperidine-1-carboxylate,
Thiazol-5-ylmethyl 4-[2-(4'-cyanobiphenyl-3-yloxy)ethyl]piperidine-1-carboxylate,
Thiazol-5-ylmethyl 4-[2-(6-cyanonaphth-2-yloxy)ethyl]piperidine-1-carboxylate,
Thiazol-5-ylmethyl 4-[2-(4-{thiazol-2-yl}phenoxy)ethyl]piperidine-1-carboxylate,
Thiazol-5-ylmethyl 4-[2-(7-methoxynaphth-2-yloxy)ethyl]piperidine-1-carboxylate,
Thiazol-5-ylmethyl 4-[2-(4-chloro-2-{isoxazol-5-yl}phenoxy)ethyl]piperidine-1-carboxylate,
Thiazol-5-ylmethyl 4-[2-(2-carbamoyl-4-chlorophenoxy)ethyl]piperidine-1-carboxylate,
Thiazol-5-ylmethyl 4-[2-(5-{acetylamino}naphth-2-yloxy)ethyl]piperidine-1-carboxylate,
Thiazol-5-ylmethyl 4-[2-(4'-cyanobiphenyl-4-yloxy)ethyl]piperidine-1-carboxylate,
Thiazol-5-ylmethyl 4-[2-(4-{methanesulphonyl}phenoxy)ethyl]piperidine-1-carboxylate,
Thiazol-5-ylmethyl 4-[2-(5-acetylamino-2-propylphenoxy)ethyl]piperidine-1-carboxylate,
Thiazol-5-ylmethyl 4-[2-(1H-indol-6-yloxy)ethyl]piperidine-1-carboxylate,
Thiazol-5-ylmethyl 4-{2-[4-fluoro-2-(1H-pyrazol-3-yl)phenoxy]ethyl}piperidine-1-carboxylate,
Thiazol-5-ylmethyl 4-[2-(4-cyano-2-fluorophenoxy)ethyl]piperidine-1-carboxylate,
Thiazol-5-ylmethyl 4-[2-(2-isopropyl-5-methylphenoxy)ethyl]piperidine-1-carboxylate,
Thiazol-5-ylmethyl 4-[2-(2-{morpholin-4-yl}phenoxy)ethyl]piperidine-1-carboxylate and its trifluoroacetate,
Thiazol-5-ylmethyl 4-[2-(2-methylquinolin-6-yloxy)ethyl]piperidine-1-carboxylate,
Thiazol-5-ylmethyl 4-{2-[4-(2-oxopyrrolidin-1-yl)phenoxy]ethyl}piperidine-1-carboxylate,
Thiazol-5-ylmethyl 4-[2-(3-{tetrazol-1-yl}phenoxy)ethyl]piperidine-1-carboxylate,
Thiazol-2-ylmethyl (R)-3-(naphth-2-yloxymethyl)pyrrolidine-1-carboxylate (enantiomer I),
Thiazol-2-ylmethyl (S)-3-(naphth-2-yloxymethyl)pyrrolidine-1-carboxylate (enantiomer II),
Thiazol-2-ylmethyl (+/−)-3-(5-chloronaphth-2-yloxymethyl)pyrrolidine-1-carboxylate,
Thiazol-2-ylmethyl (+/−)-3-(4'-fluorobiphenyl-4-yloxymethyl)pyrrolidine-1-carboxylate,
3-Carbamoylisoxazol-5-ylmethyl 4-[2-(4-fluorophenoxy)ethyl]piperidine-1-carboxylate,
3-Carbamoylisoxazol-5-ylmethyl 4-[2-(4-{trifluoromethoxy}phenoxy)ethyl]piperidine-1-carboxylate,
3-Carbamoylisoxazol-5-ylmethyl (−)-(R)-3-(naphth-2-yloxymethyl)pyrrolidine-1-carboxylate (enantiomer I),
3-Carbamoylisoxazol-5-ylmethyl (+/−)-3-(6-methoxynaphth-2-yloxymethyl)pyrrolidine-1-carboxylate and
3-Carbamoylisoxazol-5-ylmethyl (+)-(S)-3-(naphth-2-yloxymethyl)pyrrolidine-1-carboxylate (enantiomer II).

8. A pharmaceutical composition comprising the compound of claim 1 in the form of a base or of an addition salt with a pharmaceutically acceptable acid, and one or more pharmaceutical excipients.

9. A method of treating acute or chronic pain in a patient in need thereof comprising administering to said patient a therapeutically effective amount of the pharmaceutical composition of claim 8.

10. The process for the preparation of a compound according to claim 1, comprising reacting an amine derivative, a compound of following general formula (II):

in which $R_1$, $R_2$, A, n and m are as defined in claim 1, with a carbonate of following general formula (III):

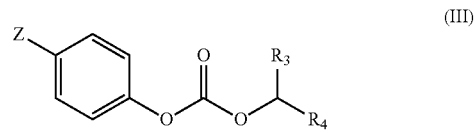

in which Z represents a hydrogen atom or a nitro group and $R_3$ and $R_4$ are as defined in claim 1, in the presence of a base, in an organic solvent, at a temperature between ambient temperature and the reflux temperature of the solvent.

11. The process according to claim 10, wherein the base is triethylamine, pyridine, N,N-dimethylaminopyridine or N,N-diisopropylethylamine.

12. The process according to claim 10, wherein the organic solvent is toluene, acetonitrile or dichloroethane.

* * * * *

UNITED STATES PATENT AND TRADEMARK OFFICE
CERTIFICATE OF CORRECTION

PATENT NO. : 9,000,010 B2
APPLICATION NO. : 13/574188
DATED : April 7, 2015
INVENTOR(S) : Ahmed Abouabdellah et al.

It is certified that error appears in the above-identified patent and that said Letters Patent is hereby corrected as shown below:

In the Abstract:

Lines 14-15, please replace "5-methylisoxazol-3-ylm-ethyl" with --5-methylisoxazol-3-ylmethyl--.

In the Claims:

At column 88, claim 1, line numbers 60-61, please replace "$C_{1-6}$-alkoxy, $C_{1-6}$-haloalkyl," with --$C_{1-6}$-alkoxy, $C_{1-6}$-thioalkyl, $C_{1-6}$-haloalkyl,--;

At column 89, claim 5, line number 53, please replace "wherein compound" with --wherein the compound--;

At column 96, claim 8, line number 31, please replace "acid, and" with --acid and--;

At column 96, claim 8, line number 32, please replace "pharmaceutical excipients." with --pharmaceutically acceptable excipients.--.

Signed and Sealed this
Fourth Day of August, 2015

Michelle K. Lee
*Director of the United States Patent and Trademark Office*